(12) United States Patent
Johnson et al.

(10) Patent No.: US 12,357,493 B2
(45) Date of Patent: *Jul. 15, 2025

(54) DEVICES, SYSTEMS, AND METHODS FOR MANIPULATING NASAL TISSUES

(71) Applicant: Spirair, Inc., South San Francisco, CA (US)

(72) Inventors: Eric Johnson, Woodside, CA (US); James R. Kintzing, Concord, CA (US); Brandon McCutcheon, Walnut Creek, CA (US); John Bower, Olympia, WA (US)

(73) Assignee: Spirair, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/798,512

(22) Filed: Aug. 8, 2024

(65) Prior Publication Data
US 2024/0398604 A1    Dec. 5, 2024

Related U.S. Application Data

(63) Continuation of application No. 18/536,115, filed on Dec. 11, 2023, now Pat. No. 12,083,034.

(60) Provisional application No. 63/386,874, filed on Dec. 9, 2022.

(51) Int. Cl.
*A61F 5/08*    (2006.01)
*A61L 27/14*    (2006.01)

(52) U.S. Cl.
CPC ............... *A61F 5/08* (2013.01); *A61L 27/14* (2013.01)

(58) Field of Classification Search
CPC .................................. A61F 5/08; A61L 27/14
See application file for complete search history.

(56) References Cited

U.S. PATENT DOCUMENTS

| | | | |
|---|---|---|---|
| 5,558,674 A | 9/1996 | Heggeness et al. | |
| 5,747,637 A * | 5/1998 | Shinoda | A61L 17/12 |
| | | | 525/413 |
| 6,626,172 B1 | 9/2003 | Karow et al. | |
| 7,438,208 B2 | 10/2008 | Larson | |
| 7,641,688 B2 | 1/2010 | Lesh | |
| 7,780,730 B2 | 8/2010 | Saidi | |
| 7,934,506 B2 | 5/2011 | Woodson et al. | |
| 7,972,379 B2 | 7/2011 | Jung et al. | |

(Continued)

FOREIGN PATENT DOCUMENTS

| | | |
|---|---|---|
| CA | 2811967 A1 | 4/2012 |
| WO | WO-0189366 A2 | 11/2001 |

(Continued)

OTHER PUBLICATIONS

Extended European Search Report for European Application No. EP21822179.4, mailed May 22, 2024, 7 pages.

(Continued)

*Primary Examiner* — Richard G Louis
(74) *Attorney, Agent, or Firm* — Cooley LLP

(57) ABSTRACT

Described herein are devices, systems, and methods for applying a tension force to various tissues. The devices may be delivered in a minimally invasive fashion and used to manipulate tissues in the nose, ear, and throat. Force may be maintained by the devices for a time period that allows shaping, compression, or approximation of tissues.

29 Claims, 89 Drawing Sheets

(56) References Cited

U.S. PATENT DOCUMENTS

| | | |
|---|---|---|
| 8,216,311 B2 | 7/2012 | Kang et al. |
| 8,241,356 B2 | 8/2012 | Vassallo et al. |
| 8,267,962 B2 | 9/2012 | Stupak |
| 8,349,013 B2 | 1/2013 | Zucherman et al. |
| 8,413,662 B2 | 4/2013 | Metzger et al. |
| 8,715,347 B2 | 5/2014 | Servell et al. |
| 8,784,488 B2 | 7/2014 | Saidi |
| 8,821,575 B2 | 9/2014 | Van Der Burg et al. |
| 9,877,862 B2 | 1/2018 | Weadock et al. |
| 9,895,252 B2 | 2/2018 | Awengen et al. |
| 9,949,823 B2 | 4/2018 | Hristov et al. |
| 10,456,230 B2 | 10/2019 | Schuchardt et al. |
| 10,835,412 B2 | 11/2020 | Krespi et al. |
| 10,980,631 B2 | 4/2021 | Rosenthal et al. |
| 11,135,083 B2 | 10/2021 | Dillard |
| 11,806,230 B2 | 11/2023 | Kintzing et al. |
| 2002/0077598 A1 | 6/2002 | Yap et al. |
| 2002/0173848 A1 | 11/2002 | Sachs |
| 2003/0149447 A1* | 8/2003 | Morency .......... A61B 17/06166 606/228 |
| 2004/0088003 A1 | 5/2004 | Leung et al. |
| 2006/0276817 A1 | 12/2006 | Vassallo et al. |
| 2007/0219575 A1 | 9/2007 | Mejia |
| 2008/0027480 A1 | 1/2008 | van der Burg et al. |
| 2008/0077075 A1 | 3/2008 | Moreira et al. |
| 2008/0077240 A1 | 3/2008 | Saidi |
| 2008/0102122 A1* | 5/2008 | Mahadevan ............ A61L 27/14 424/618 |
| 2008/0109036 A1* | 5/2008 | Stopek .................... A61L 17/12 606/228 |
| 2008/0188947 A1 | 8/2008 | Sanders |
| 2008/0208265 A1 | 8/2008 | Frazier et al. |
| 2009/0177272 A1 | 7/2009 | Abbate et al. |
| 2011/0093004 A1 | 4/2011 | Ierulli |
| 2011/0118779 A1 | 5/2011 | Olien et al. |
| 2011/0251634 A1 | 10/2011 | Gonzales et al. |
| 2012/0078244 A1 | 3/2012 | Worrell et al. |
| 2012/0310280 A1 | 12/2012 | Harrington |
| 2013/0006293 A1 | 1/2013 | Smith |
| 2013/0317540 A1 | 11/2013 | Hristov et al. |
| 2013/0331839 A1 | 12/2013 | Hester et al. |
| 2013/0338700 A1 | 12/2013 | Matheny |
| 2014/0048348 A1 | 2/2014 | Pellenc et al. |
| 2014/0074238 A1 | 3/2014 | Abbate et al. |
| 2014/0228971 A1 | 8/2014 | Kim |
| 2016/0058556 A1 | 3/2016 | Rosenthal et al. |
| 2016/0157846 A1 | 6/2016 | Poucher et al. |
| 2017/0056036 A1* | 3/2017 | Jenkins .............. A61B 17/0401 |
| 2018/0116648 A1 | 5/2018 | Kim |
| 2020/0197171 A1 | 6/2020 | Saidi et al. |
| 2020/0253726 A1 | 8/2020 | Saidi |
| 2020/0315839 A1 | 10/2020 | Sanders |
| 2021/0212813 A1 | 7/2021 | Baron et al. |
| 2021/0315689 A1 | 10/2021 | Rosenthal et al. |
| 2022/0000609 A1 | 1/2022 | Kintzing et al. |
| 2022/0395367 A1 | 12/2022 | Johnson et al. |
| 2024/0081979 A1 | 3/2024 | Kintzing et al. |
| 2024/0189132 A1 | 6/2024 | Johnson et al. |

FOREIGN PATENT DOCUMENTS

| | | |
|---|---|---|
| WO | WO-2006112678 A1 | 10/2006 |
| WO | WO-2010059586 A1 | 5/2010 |
| WO | WO-2014134185 A1 | 9/2014 |
| WO | WO-2018183561 A1 | 10/2018 |
| WO | WO-2021252806 A1 | 12/2021 |
| WO | WO-2022261474 A1 | 12/2022 |
| WO | WO-2024124253 A1 | 6/2024 |

OTHER PUBLICATIONS

International Preliminary Report on Patentability for International Application No. PCT/US2022/033070, mailed Dec. 21, 2023, 11 pages.

International Search Report and Written Opinion for Application No. PCT/US2021/036881, mailed Oct. 1, 2021, 14 pages.

International Search Report and Written Opinion for International Application No. PCT/US2022/033070, mailed Oct. 12, 2022, 15 pages.

International Search Report and Written Opinion for International Application No. PCT/US2023/083451, mailed Feb. 29, 2024, 11 pages.

Invitation to Pay for International Application No. PCT/US2022/033070, mailed Aug. 12, 2022, 2 pages.

Partial Supplementary European Search Report for European Application No. 22821138.9 mailed Feb. 27, 2025, 13 pages.

* cited by examiner

FIG. 62A  FIG. 62B

Implant cut from Multilayer Laminate

Cutting Profile

Tapered Profile

DEVICES, SYSTEMS, AND METHODS FOR MANIPULATING NASAL TISSUES

CROSS-REFERENCE TO RELATED APPLICATIONS

This application is a continuation of U.S. patent application Ser. No. 18/536,115, filed Dec. 11, 2023, now U.S. Pat. No. 12,083,034, which claims priority to U.S. Provisional Application No. 63/386,874, filed on Dec. 9, 2022, each of which is hereby incorporated by reference in its entirety.

FIELD

This application generally relates to devices, systems, and methods for applying a tension force to various tissues. The devices may be delivered in a minimally invasive manner and used to manipulate tissues in the nose, ear, and throat. Force may be maintained for a time period that allows shaping, compression, or approximation of tissues.

BACKGROUND

Nasal septal deviations occur in up to 75% of the population, with far fewer being symptomatic. When symptomatic, a deviated septum may cause nasal airway obstruction which impairs the patient's ability to breath. When symptoms are sufficiently severe the patient may require a septoplasty or septorhinoplasty surgery. Approximately 300,000-600,000 patients require this surgery in the United States every year. While many ENT surgeries have been transitioned to an office-based setting with minimally invasive approaches, septal surgery has fundamentally lagged behind; leaving patients and physicians looking for minimally invasive approaches.

Septal surgery is non-trivial. For the patient, it requires a trip to the operating room and general anesthesia. The recovery can also be significant, especially in the case of septorhinoplasty. For the surgeon, operating room (OR) based surgeries can present increased risks and costs while also introducing inefficiencies in the delivery of care. Therefore, both surgeons and patients may be interested in less invasive procedures that can be performed in a lower resource setting.

There are currently no minimally-invasive septal correction devices in clinical practice today. Thus, there is a need for new and useful devices and methods for manipulating and reshaping the nasal septal cartilage. New devices and methods for manipulating and reshaping other nasal tissues, as well as tissues of the ear and throat may also be useful.

SUMMARY

Described herein are devices, systems, and methods for applying a tension force to various tissues. The devices may be delivered in a minimally invasive fashion and used to manipulate tissues in the nose, ear, and throat, as well as other tissues as described elsewhere herein. Force may be maintained for a time period that allows shaping, compression, or approximation of tissues. The devices may include a tension element having a distal anchor that may be inserted in an insertion configuration into or through tissue in one direction, and upon application of force in the opposite direction, may swivel, flex, flare, rotate, expand or pivot about a pivot point of the distal anchor to a deployed configuration to prevent passage of the distal anchor back through the tissue. In some instances, the longitudinal axis of the distal anchor in its deployed configuration is orthogonal to the longitudinal axis of the tension element. Tension may continue to be applied to the tension element and adjusted to the amount desired for the intended application. For example, tension may be adjusted to an amount that alters the shape of nasal tissues (e.g., a nasal septum, a nasal valve). As used herein, the terms "tension element" and "shaping element" are used interchangeably throughout.

Other devices for manipulating a tissue in a subject may include a tension element, where the tension element includes an elongate body having a proximal end and a distal end, and a distal anchor at the tension element distal end having a radially expanded configuration after deployment. The distal anchor may include an anchor body having a surface area, an insertion configuration, and a deployed configuration, where the distal anchor in the deployed configuration has a larger surface area for opposing tissue than the distal anchor in the insertion configuration.

The tension element may be made from biodegradable or non-biodegradable materials. When the tension element is biodegradable, it may be made from a biodegradable polymer. Exemplary biodegradable polymers include without limitation, LPLA (Poly(L-lactide)), DLPLA (Poly(DL-lactide)), LDLPLA (Poly(DL-lactide-co-L-lactide)), LPLA-HA (Poly(L-lactide) with hydroxylapatite), PGA (Poly(glycolide)), PGA-TMC (Poly(glycolide-co-trimethylene carbonate) or polyglyconate), PDO (Poly(dioxanone)), LPLG (Poly(L-lactide-co-glycolide)), DLPLG (Poly(DL-lactide-co-glycolide), or copolymers or blends thereof. In some variations, the biodegradable polymer comprises a polylactide, a poly(orthoester), a poly(phosphoester), a polyphosphazene, a polyanhydride, a polycaprolactone, a polyurethane, a polycarbonate, chitosan, cyclodextrin, dextran, hyaluronic acid, chondroitin sulfate, dermatan sulfate, heparin, heparin sulfate, keratan sulfate, or a copolymer or blend thereof. In one variation, the tension element or a portion of the tension element may be made from PDO (Poly(dioxanone)). In another variation, the tension element may be made from a metal, for example, magnesium or a magnesium alloy. Other metals may also be used. When the tension element is non-biodegradable, it may be made from a non-biodegradable polymer. Exemplary non-biodegradable polymers include without limitation, polypropylene, polyvinyl chloride, polyethylene, polythene terephthalate, and polystyrene. Other materials that may be used to make the tension elements include textiles and non-woven materials (e.g., materials made by electrospinning).

When the tension element is formed from a biodegradable material, it may degrade over a period of about one month, two months, three months, about four months, about five months, about six months, about seven months, about eight months, about nine months, about ten months, about eleven months, or about twelve months. In one variation, the tension element may degrade over a period ranging from about four months to about nine months. In another variation, the tension element may degrade over a period of about six months.

When the tension element is non-biodegradable, it may be made from a non-biodegradable polymer or a metal. Exemplary non-biodegradable polymers include without limitation, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly (vinyl imidazole), chorosulphonated polyolefins, polyethylene oxide, silk, Nylon, polyamide, polypropylene, polyester, polybutester, polytetrafluoroethylene (PTFE), expanded PTFE (ePTFE), aromatic polyamides (aramids), and copolymers and blends thereof. Exemplary metals include, but are not limited to, silver, platinum, stainless steel, nickel, titanium, and alloys thereof.

The tension element may be configured to hold or maintain a force on a target tissue. The force may be a tension force ranging from about 4.0 Newtons to about 70 Newtons, including all values and sub-ranges therein, which may be generated by pulling on at least a portion of the tension element (e.g., the free proximal end of the tension element) after the distal anchor has been fixed to the target tissue. Tensile strength of the tension element may range from about 100 MPa to about 800 MPa, including all values and sub-ranges therein. In some instances, the tensile strength may be at least about 150 MPa. In other instances, the tensile strength may be at least about 300 MPa.

The length of the tension element prior to delivery may vary depending on the target tissue of deployment, type of procedure being performed, and/or the anatomy of the subject. Tension element length prior to delivery may range from about 10 cm to about 30 cm. In one variation, the tension element may have a length of about 15 cm prior to delivery. Once delivered to the target tissue, the tension element may be trimmed to a length that applies an appropriate amount of force, reshaping, etc., to the target tissue. The longer length may help facilitate handling of the tension element while the target tissue is being manipulated.

The distal anchor may be variously sized and shaped. In general, the distal anchor in its deployed configuration prevents passage of the distal end of the tension element back though tissue. The anchor body may include a plurality of arms, where the arms may be configured to swivel at the pivot point upon the application of force to the elongate body. Each arm of the plurality of arms may include a distal end that is sloped or bevel cut to help swivel the distal anchor at the pivot point and facilitate its engagement against tissue. Alternatively, the anchor body may be rectangular, square, triangular, circular, or ovular in shape. The anchor body may also be diamond-shaped, or shaped like an arrow or a dog bone. In some variations, the anchor body includes a heel and a toe retainer. In other variations, the anchor body may be expandable from a collapsed configuration to an expanded configuration. Here the collapsed configuration may allow insertion of the distal anchor through tissue in a first direction, and the expanded configuration prevent passage of the distal anchor back through the tissue in a second direction, e.g., in a direction opposite to the first direction. Non-limiting examples of expandable distal anchors include expandable knots or molly bolt type anchors. In addition to molly bolt type anchors, the distal anchor may include multiple components, where one component at the distal end of the tension element may be configured to interlock with a complementary component after insertion and passage of the tension element through tissue. The complementary component or combined structure of the interlocking components may prevent passage of the tension element back through the tissue.

A plurality of proximal anchors (migration prevention elements) may further be disposed between the distal anchor and the proximal end of the tension element. The distal anchor and the plurality of proximal anchors may be the same type of anchor or different types of anchors. An enlarged tip may also be provided at the distal end of the tension element distal to the distal anchor to further facilitate anchoring of the tension element to tissue and/or coupling to an anchor delivery element, as further described below. The distal anchor and plurality of proximal anchors may be made from the same material as the tension element, or from different materials. In some variations, the distal anchor may be made from a non-biodegradable material, and the plurality of proximal anchors made from a biodegradable material.

The devices described herein may further include a proximal needle removably attached to the proximal end of the elongate body of the tension element. The proximal needle may be used to place or manipulate the proximal end of the elongate body through or around tissue, and may be removably attached in various ways to the tension element. For example, the proximal needle may be removable attached to the tension element by swaging or crimping, or by threading the tension element through a corresponding structure in the proximal needle.

At the distal end of the tension element, an anchor delivery element may be coupled to the distal anchor. The anchor delivery element may include an anchor support and a cutting tip configured to pass the distal anchor through the tissue in its insertion configuration. The anchor delivery element may also include a keyhole shaped to removably couple the distal anchor to the anchor delivery element. For example, the keyhole may be dimensioned to keep the distal anchor coupled to the anchor delivery element during tissue insertion but allow disengagement of distal anchor during withdrawal of the anchor delivery element back through the tissue. Some variations of the anchor delivery element include an anchor support having a seating region configured to removably secure the anchor to the anchor delivery element. The seating region may be shaped to correspond to the shape of the distal anchor. Furthermore, the seating region may generally have a height that is level with a height of the distal anchor when the distal anchor is seated on the anchor delivery element. Leveling of the seating region and distal anchor heights may present a flush surface to tissue that may prevent the anchor delivery element from catching on tissue during insertion. In some instances, disengagement of the distal anchor from the seating region may be accomplished using a release tab. The distal anchor may also be disengaged using mechanisms or actuators that may include one or more of a releasable wire, a sliding wedge, a spring (e.g., a remote actuated compression spring), an expandable member (e.g., an inflatable/collapsible balloon), a leaf spring, a Nitinol shape set, or a cotter pin. In other instances, the seating region may have a size and shape that allows the distal anchor to couple to the seating region via an interference fit. For example, the distal anchor and seating region may have the same shape, but the distal anchor may be sized slightly larger than the seating region such that it may be press fit therein.

The tissues that may be manipulated with the devices describe herein include without limitation, nasal tissues, throat tissues, and car tissues. Non-limiting examples of nasal tissue include nasal septal cartilage, lateral nasal cartilage, major alar cartilage, minor alar cartilage, alar fibrofatty tissue, nasal bone, or a nasal turbinate. Exemplary throat tissues include without limitation, the uvula, soft palate, laryngeal cartilage, thyroid cartilage, cricoid cartilage, epiglottis, and tonsils. Non-limiting examples of car tissues include cartilage of the helix, anti-helix, tragus, anti-tragus, superior crus, fossa triangularis, concha, and connective tissue of the earlobe. The devices may also be used to manipulate or shape cartilage, bone, or other tissues in orthopedic applications, or to manipulate or shape vascular, heart, or other tissues in cardiovascular applications. The devices may further be used in cosmetic applications to reshape or support tissue. The devices may also be used in urologic or gynecologic applications to reshape or support tissue. For example, the devices may be used to alter the shape of penile curvature. The device may also be used to support pelvic floor muscles. In some instances, the devices described herein may be used to splint, hold, or support a tissue.

In another variation, the device for manipulating a tissue in a subject includes a tension element, where the tension element comprises an elongate body having a proximal end and a distal end; a distal anchor at the tension element distal end that includes an anchor body and a pivot point, and an insertion configuration and a deployed configuration; a plurality of proximal anchors disposed between the distal anchor and the proximal end of the tension element; and a catch between the distal anchor and the plurality of proximal anchors. The catch may be configured to decouple (e.g., release or detach) the distal anchor from a delivery device. Additionally, the distal anchor may be configured to swivel at the pivot point from the insertion configuration to the deployed configuration upon the application of force to the elongate body.

Methods for manipulating a tissue in a subject are also described herein. The methods may generally include securing a tension element to the tissue, where the tension element comprises an elongate body having a proximal end and a distal end, and a distal anchor at the tension element distal end. In some variations, the distal end of the tension element may be directed through the tissue with an anchor delivery element. The distal anchor may include an anchor body and a pivot point, and an insertion configuration and a deployed configuration. After securing the tension element to tissue, a force may be applied to the elongate body to swivel the distal anchor at the pivot point from the insertion configuration to the deployed configuration. The force appropriate to manipulate the tissue may then be adjusted by adjusting the tension of the tension element. In some variations, the tension element may also include a plurality of proximal anchors disposed between the distal anchor and the proximal end of the tension element, and a catch between the distal anchor and the plurality of proximal anchors.

Some variations of the method may include providing a mechanical advantage to anchor delivery element/tension element deployment from a delivery device. Stated differently, some methods may produce more force when deploying the anchor delivery element/tension element than the force applied by a user (e.g., surgeon) to a delivery device or any component thereof, and this ratio of the produced force to the applied force may be referred to as mechanical advantage. The delivery devices described herein may be configured to provide a mechanical advantage that ranges from about 2:1 to about 4:1, including all values and sub-ranges therein.

In one variation, the methods for reshaping one or more nasal tissues in a subject may include advancing a delivery device through the one or more nasal tissues, where the delivery device may comprise an elongate tension element preloaded therein, an anchor delivery element configured to couple with at least a portion of the elongate tension element, and an actuator, and advancing the anchor delivery element from the delivery device through the one or more nasal tissues with a deployed force that is greater than an applied force by a user. After reaching a target area of the one or more nasal tissues, the tension element may be deployed from the anchor delivery element and into the target area. The ratio of the deployed force to the applied force may range from about 2:1 to about 4:1, as previously mentioned.

The delivery device may be advanced by inserting a cannula of the delivery device through an access site in submucosal tissue on a first side of the nasal septum and through the nasal septum to a second side of the nasal septum. A distal anchor of the preloaded tension element may then be secured into nasal cartilage on the second side of the nasal septum, where the distal anchor comprises a pivot point and has an insertion configuration and a deployed configuration. The method may include securing the distal anchor by applying a force to the elongate tension element to swivel the distal anchor at the pivot point from the insertion configuration to the deployed configuration. In some variations, the method may further include passing a proximal end of the elongate tension element back through the access site in submucosal tissue to the second side of the nasal septum, tensioning the elongate tension element to a tensioned state, and securing the proximal end of the elongate tension element in its tensioned state to tissue on the second side of the nasal septum. In further variations, the proximal end of the elongate tension element may be passed back through the access site in submucosal tissue multiple times similar to a running suture technique to increase the retention force and/or provide appropriate correction to a deviation. The tension element in its tensioned state may apply a force ranging from about 1.0 Newton to about 70 Newtons (including all values and sub-ranges therein) to the one or more nasal tissues.

The proximal and distal ends of the elongate body of the tension element may be secured to the same tissue. Alternatively, the proximal and distal ends of the elongate body may be secured to different tissues. The tissue may be a nasal tissue, a throat tissue, or an ear tissue. Exemplary nasal tissues include without limitation, nasal septal cartilage, lateral nasal cartilage, major alar cartilage, minor alar cartilage, alar fibrofatty tissue, nasal bone, or a nasal turbinate. Exemplary throat tissues include without limitation, the uvula, soft palate, laryngeal cartilage, thyroid cartilage, cricoid cartilage, epiglottis, and tonsils. Non-limiting examples of ear tissues include cartilage of the helix, antihelix, tragus, anti-tragus, superior crus, fossa triangularis, concha, and connective tissue of the earlobe.

The methods described herein may be used to treat various conditions and manipulate various tissues. For example, the manipulation of tissue by the tension elements may be used to treat nasal septal deviation, lateral nasal valve collapse, and other causes of nasal airway obstruction. Additionally, the manipulation of tissue may be used to medialize a middle turbinate, compresses or lateralize the inferior turbinate, or reapproximate nasal mucosa. Furthermore, the manipulation of tissue by the tension elements may alter the shape of various tissues. For example, the shape of a nasal tissue, a throat tissue, or an car tissue may be altered.

The force applied to manipulate or shape a tissue may range from about 4.0 Newtons to about 70 Newtons. The applied force may decrease over time as the tension element biodegrades. In general, the tension element biodegrades over a period of about three months to about twelve months. For example, the tension element may biodegrade over a period of at least about four months, over a period of at least about six months, or over a period of at least about nine months.

Delivery of the devices are also described herein. In general, the delivery devices may include a cannula comprising a proximal end, a distal end, and an atraumatic tip. The cannula may include a curved distal end, and may further include a lumen extending from the proximal end through the atraumatic tip, in which a tension element may be housed. The tension element may include a distal anchor configured to swivel, flex, flare, expand, rotate, or pivot about a pivot point from an insertion configuration to a deployed configuration upon the application of force to the tension element. The tension element and anchor delivery element may be preloaded in the delivery device or loaded into the delivery device right before the procedure. A handle may be coupled to the cannula proximal end and configured for single-handed use or use by both a right hand or a left hand (e.g., configured for universal use). In some variations, an actuator may be concentrically disposed about the handle. The actuator may be coupled to the anchor delivery element to advance the anchor delivery element and tension element coupled thereto from the lumen of the cannula.

Some variations of the delivery device may include a cannula comprising a proximal end, a distal end, and a lumen extending from the proximal end through the distal end and configured to house a tension element; a handle coupled to the cannula proximal end; and an actuator configured to translate rotational motion into linear motion, where the tension element may include a distal anchor configured to swivel at a pivot point from an insertion configuration to a deployed configuration upon the application of force to the tension element. In these variations, the actuator may be configured to advance the anchor delivery element into tissue with a deployed force that is greater than an applied force by a user. The ratio of the deployed force to the applied force may range from about 2:1 to about 4:1, including all values and sub-ranges therein. Exemplary actuators may comprise a linear gear and a fixed sector gear, or a linear gear and an eccentric sector gear, as further described below.

In some variations, the cannula of the delivery device may be made from a polymer. Exemplary polymers include, but are not limited to, acrylic, polycarbonate, polyethylene terephthalate, polyvinyl chloride, polyethylene, polypropylene, and polystyrene. Transparent forms of the aforementioned polymers may be used to make a transparent cannula. In other variations, the cannula may be made from stainless steel or other suitable metals. The cannula may include markings thereon to help facilitate tension element placement. When made from a metal, the markings may be laser markings.

The cannula may also have various cross-sectional shapes. For example, the cross-sectional shape of the cannula may be circular, non-circular, semi-circular, or ovular. In some variations where the cannula cross-section is non-circular, the shape may facilitate orientation of the cannula. One or more ports in fluid communication with the lumen may be provided in the cannula for delivery of the tensioning element from the lumen into tissue. The one or more ports may be provided in any suitable location on the cannula, for example, at the distal tip of the cannula or distal side wall of the cannula. The one or more ports may also have any suitable shape. For example, the one or more ports may be circular, semi-circular, or ovular. When a port is provided at the distal tip of the cannula, the port may have a length and a depth. The side profile of the port may also include a curved portion and a flat portion.

The delivery devices may also include a handle comprising a grip. The grip may include a plurality of ridges for enhancing the hold of a user on the handle. A directional indicator for orienting the port with respect to the location of anchoring in the target tissue may also be provided on the handle.

Systems for reshaping tissues are also described herein. In general, the systems may include a tension element preloaded within a delivery device. The delivery device may further include an anchor delivery element configured to couple with at least a portion of the tension element, and an actuator configured to advance the anchor delivery element into tissue with a deployed force that is greater than an applied force by a user. The ratio of the deployed force to the applied force (i.e., the mechanical advantage) ranges from about 2:1 to about 4:1, including all values and sub-ranges therein. The actuator may be configured to translate rotational motion into linear motion. For example, the actuator may comprise a linear gear and a fixed sector gear, or a linear gear and an eccentric sector gear.

In some instances, the devices for shaping a tissue structure of a subject may include an elongate member comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

In other instances, the devices for shaping a tissue structure of a subject may include an elongate member comprising a proximal end, a distal end sized for introduction into the subject's body, and a lumen extending between the proximal end and a port at the distal end, and a needle removably coupled to the elongate member. A shaping element may further be included that comprises a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

Other variations of the devices for shaping a tissue structure of a subject may include an elongate member comprising a proximal end, a distal end sized for introduction into the subject's body, and a lumen extending between the proximal end and a port at the distal end, a needle removably coupled to the elongate member, and a shaping element. The shaping element may include a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

In some variations, the devices for shaping a tissue structure of a subject may include an elongate member comprising a proximal end, a distal end sized for introduction into the subject's body, a lumen extending between the proximal end and the distal end, a first port at the distal end, and a second port located proximal to the first port, and a shaping element. The shaping element may comprise a first end deployable from the first port to engage tissue at a first location adjacent the tissue structure, and a second end deployable from the second port to engage tissue at a second location adjacent the tissue structure, and one or more elements to maintain tension on the engaged tissue to alter the shape of the tissue structure.

Additional methods for altering the shape of tissue structures of a subject are also described herein. In accordance with an exemplary variation, the method may employ a device that includes an elongate member comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

Methods are also provided for altering the shape of nasal tissue of a subject that include inserting a distal end of a delivery device into a nasal airway of the subject, deploying a first end of a shaping element from the distal end into the nasal airway; securing the first end of the shaping element to tissue adjacent the nasal airway, manipulating the shaping element to alter a shape of the tissue, and removing the delivery device such that the shaping element at least temporarily maintains the altered shape of the tissue.

Furthermore, methods are provided for altering the shape of nasal tissue of a subject that include deploying a first end of a shaping element into a nasal airway of the subject, securing the first end of the shaping element to tissue at a first location adjacent the nasal airway, manipulating the shaping element to alter a shape of the tissue, and securing the shaping element relative to tissue at a second location to maintain the altered shape of the tissue.

Yet further described herein are methods for altering the shape of a target tissue structure of a subject that include securing a first end of a shaping element to tissue adjacent the structure; manipulating the tissue to alter a shape of the structure, and applying a force to the shaping element to maintain the altered shape of the structure.

In accordance with some variations, methods are described that provide for altering the shape of nasal tissue of a subject including the steps of introducing an anchor into a nasal airway of the subject, securing the anchor at a first location to a nasal septum of the subject, introducing a first end of a shaping element into a nasal airway of the subject, securing the first end of the shaping element to the anchor, manipulating the shaping element to alter a shape of the tissue, and securing the shaping element relative to tissue at a second location to maintain the altered shape of the tissue.

The methods for altering the shape of nasal tissue of a subject described herein may also include inserting a distal end of a delivery device into a nasal airway of the subject, deploying a first end of a shaping element from the distal end into the nasal airway, securing the first end of the shaping element to tissue at a first location adjacent the nasal airway, removing the delivery device such that the shaping element extends from nasal airway, inserting a needle coupled to a second end of the shaping element into the nasal airway, manipulating the shaping element to alter a shape of the tissue, and securing the second end at a second location adjacent the nasal airway to at least temporarily maintain the altered shape of the tissue.

BRIEF DESCRIPTION OF THE DRAWINGS

Illustrative aspects of the present disclosure are described in detail below with reference to the following drawings. It will be appreciated that the exemplary devices shown in the drawings are not necessarily drawn to scale, with emphasis instead being placed on illustrating the various features of the illustrated variations.

In FIG. 12, the delivery device includes a tip for housing a tension element. The delivery device shown in FIG. 13 includes a pistol grip.

In FIG. 27, the tension element includes an enlarged distal end that interfaces with a securing element; and in FIG. 28, the securing element includes a tissue interaction feature designed to catch on tissue.

FIGS. 62A-62C depict an exemplary method of elevating the uvula and soft palate to treat obstructive sleep apnea.

FIG. 78A shows an actuated spring; FIG. 78B shows an inflatable/collapsible balloon; and FIG. 78C shows a leaf spring.

DETAILED DESCRIPTION

Figure 1:
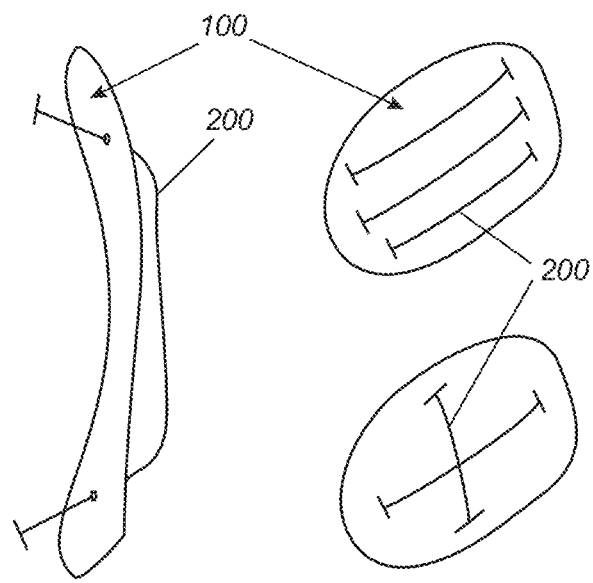
FIG. 1 depicts an exemplary tension element for use in altering the shape of a nasal tissue.

Described herein are devices, systems, and methods for applying a tension force to various tissues. The devices may be delivered in a minimally invasive fashion and used to manipulate tissues in the nose, ear, and throat. The tension force may be maintained for a time period that allows shaping, compression, or approximation of tissues. The devices may include a tension element having a distal anchor that may be inserted in an insertion configuration into or through tissue in one direction, and upon application of force in the opposite direction, may swivel, flex, pivot, expand, rotate, or flare to a deployed configuration to prevent passage of the distal anchor back through the tissue. Once the distal anchor has transitioned to the deployed configuration, additional force may be applied to the tension element and adjusted to the amount desired for the intended application. For example, the tension element may be placed in one or more nasal tissues and the tension adjusted to an amount that alters the shape of nasal tissues. Conditions such as nasal septal deviation, lateral nasal valve collapse, and other causes of nasal airway obstruction may be treated in this manner. For example, as described below in Example 1, nasal airway obstruction may be treated an improved with placement of the tension elements.

Accessory devices that help to limit the amount of tension force applied to the tension element, are also described herein. Devices for delivering one or more tension elements are further described herein. In some variations, the delivery devices may include an actuator configured to advance the tension element into tissue with a deployed force that is greater than an applied force by a user.

Devices

Tension Elements

The devices for manipulating a tissue in a subject generally include a tension element, where the tension element includes an elongate body having a proximal end and a distal end. A distal anchor having an insertion configuration and a deployed configuration may be provided at the tension element distal end and include an anchor body and a pivot point. Upon application of force to the elongate body, the distal anchor may be configured to swivel, flex, expand, rotate, flare, or pivot about the pivot point to transform from the insertion configuration to the deployed configuration, as stated above. In the deployed configuration, the distal anchor generally fixes or anchors the distal end of the tension element within tissue, or flattens against tissue (e.g., nasal cartilage), to prevent removal of the tension element therefrom. This applied force is generally in the direction opposite to the direction of insertion. In some instances, the longitudinal axis of the distal anchor in its deployed configuration is orthogonal to the longitudinal axis of the tension element. The tension element may also include a plurality of proximal anchors between the distal anchor and the proximal end of the elongate body. A needle may further be provided at the proximal end of the elongate body to facilitate advancement or placement of the tension element through tissue after the distal anchor is deployed.

Figure 84A:
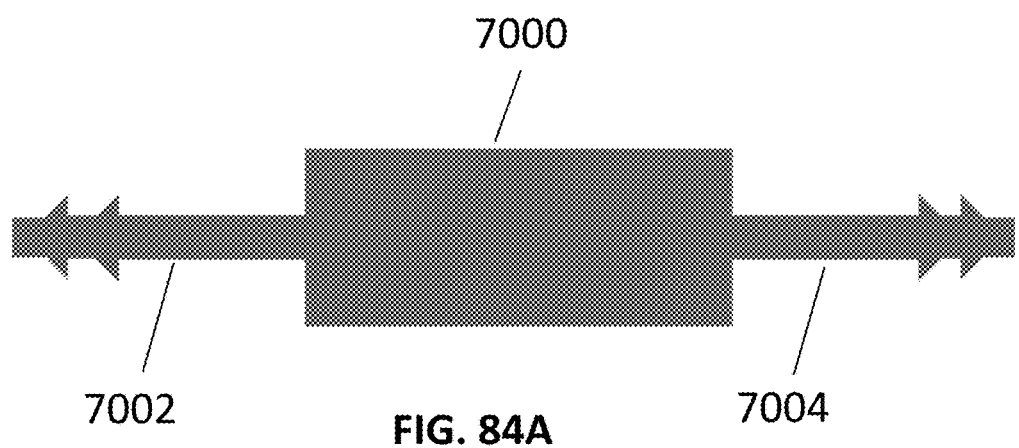
FIGS. 84A and 84B depict exemplary common core or central elements for attaching multiple tension elements.
Figure 84B:
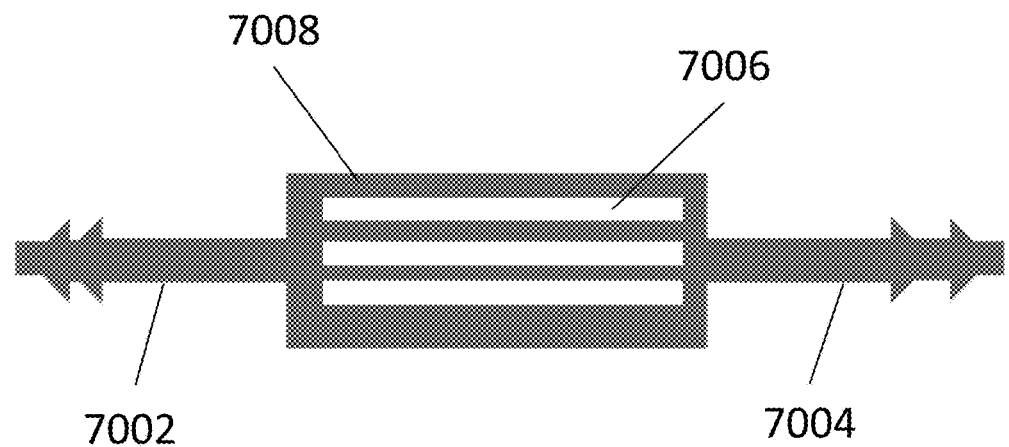
Figure 85:
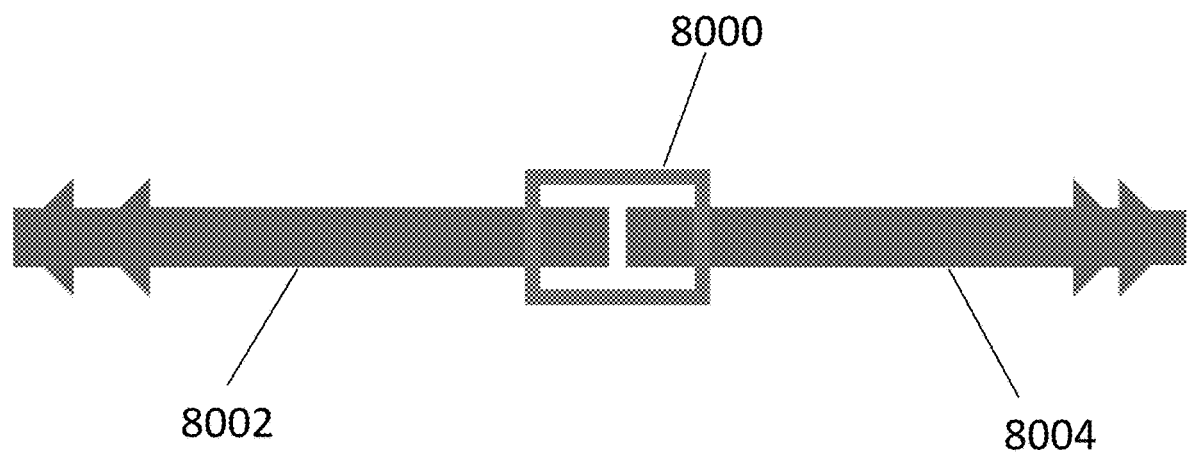
FIG. 85 shows an exemplary connector for attaching multiple tension elements.

One or more tension elements may be delivered to manipulate or shape a tissue. When multiple tension elements are used, they may be deployed separately and anchored at multiple locations within tissue, preformed to be attached together, or preformed to include a common core or central element. For example, multiple tension elements may be preformed together to create a "Y" or other configuration to achieve multiple tensioning vectors. The common core or central element may have any size and shape, e.g., square, rectangular, circular, ovular, or triangular. For example, referring to FIG. 84A, the common core/central element (7000) that attaches a first tension element (7002) to a second tension element (7004) may be rectangular in shape in order to cover a larger area of tissue (e.g., a deviated nasal septum). For nasal applications, e.g., when used to reshape nasal tissues, the rectangular common core/central element (7000) may have a width ranging from about 2.0 mm to about 10 mm, including all values and sub-ranges therein, and a length ranging from about 5.0 mm to about 15 mm, including all values and sub-ranges therein. For example, the width of the common core/central element may be about 2.0 mm, about 3.0 mm, about 4.0 mm, about 5.0 mm, about 6.0 mm, about 7.0 mm, about 8.0 mm, about 9.0 mm, or about 10 mm. The length of the common core/central region may be about 5.0 mm, about 6.0 mm, about 7.0 mm, about 8.0 mm, about 9.0 mm, about 10 mm, about 11 mm, about 12 mm, about 13 mm, about 14 mm, or about 15 mm. The width and length of the rectangular common core/central element may vary, for example, be wider and/or longer when used with non-nasal tissues. In some instances, the rectangle may include cutouts (7006) to form a banded common core/central element (7008) having increased flexibility than common core/central element (7000), as shown in FIG. 84B. In some instances, the multiple tension elements may be attached via a connector. The connector may be configured in various ways. For example, as shown in FIG. 85, the connector may be a clasp (8000) (e.g., a fold-over clasp) that couples a first tension element (8002) to a second tension element (8004). In other variations, the clasp may be configured to include a rectangular slot with biased teeth that engage and prevent slippage of the first and second tension elements, or configured as a crimp that compresses ends of the first and second tension elements together. In a further variation, the crimp may configured like a zip tie and looped around the ends of the first and second tension elements to secure them together as the loop is pulled tighter around the ends.

The tension element may be made from biodegradable or non-biodegradable materials. When the tension element is biodegradable, it may be made from a biodegradable polymer. Exemplary biodegradable polymers include without limitation, LPLA (Poly(L-lactide)), DLPLA (Poly(DL-lactide)), LDLPLA (Poly(DL-lactide-co-L-lactide)), LPLA-HA (Poly(L-lactide) with hydroxylapatite), PGA (Poly(glycolide)), PGA-TMC (Poly(glycolide-co-trimethylene carbonate) or polyglyconate), PDO (Poly(dioxanone)), LPLG (Poly(L-lactide-co-glycolide)), DLPLG (Poly(DL-lactide-co-glycolide), or copolymers or blends thereof. In some variations, the biodegradable polymer comprises a polylactide, a poly(orthoester), a poly(phosphoester), a polyphosphazene, a polyanhydride, a polycaprolactone, a polyurethane, a polycarbonate, chitosan, cyclodextrin, dextran, hyaluronic acid, chondroitin sulfate, dermatan sulfate, heparin, heparin sulfate, keratan sulfate, or a copolymer or blend thereof. In one variation, the tension element may be made from PDO (Poly(dioxanone)). In another variation, the tension element may be made from a metal, for example, magnesium or a magnesium alloy. Other metals may also be used.

Figures 71A, 71B, 71C:
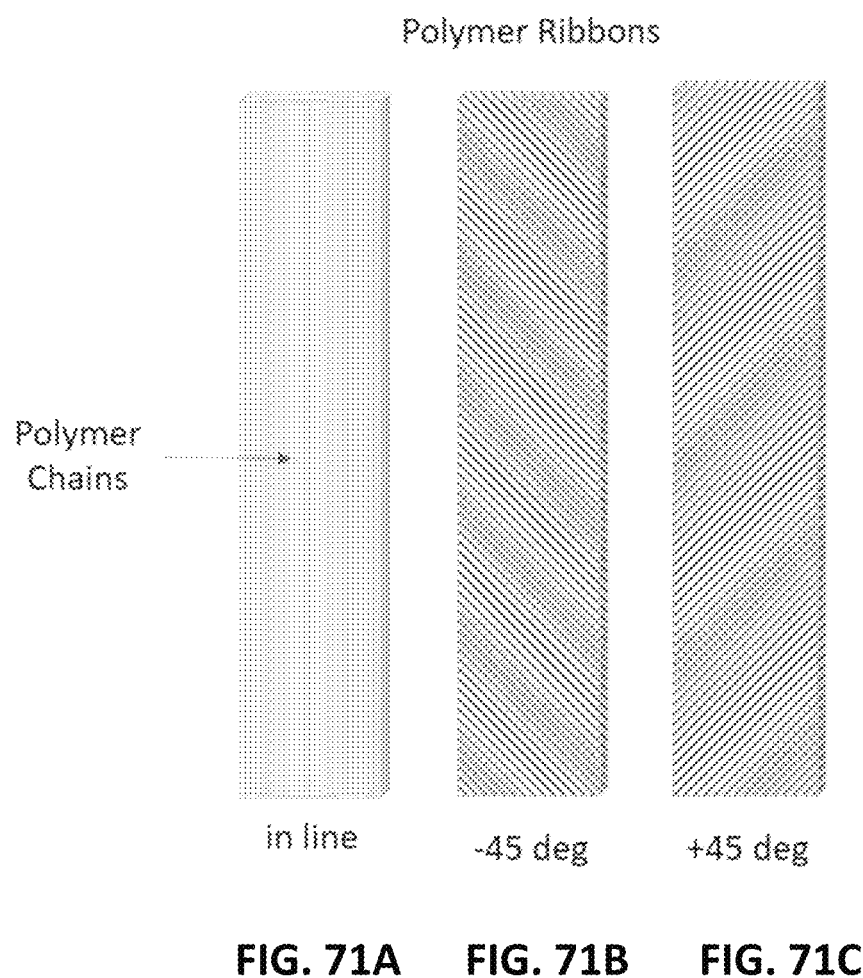
FIGS. 71A-71C depict exemplary polymer chain orientations that may be included in the polymer materials used to make the tension elements.

When the tension element is made from a biodegradable polymer, the polymer chains may have various orientations. For example, the orientation of the polymer chains may be in-line, as shown in FIG. 71A. In other variations, the polymer chains may be oriented at −30 degrees, at −45 degrees, at −60 degrees, at +30 degrees, at +45 degrees, or at +60 degrees. In one variation, as shown in FIG. 71B, the polymer chains may have a −45 degree orientation. In another variation, as shown in FIG. 71C, the polymer chains may have +45 degree orientation.

Figure 71D:
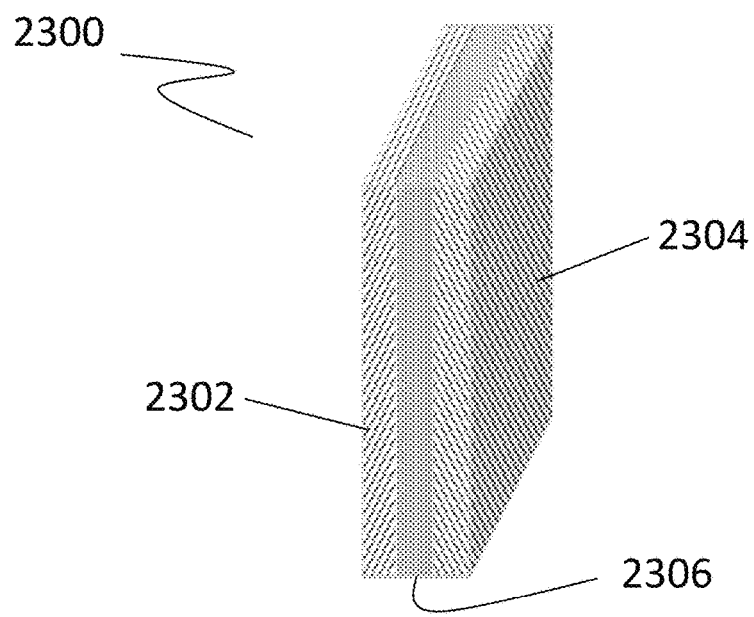
FIG. 71D depicts an exemplary multilayer polymer laminate made from layers having different polymer chain orientations.

Some variations of the tension element (and other components of the device, e.g., the anchor delivery element) may be made from a laminate including multiple polymer layers. This multi-layered polymer material may be more robust and less prone to tearing and/or shearing. The multilayer laminate may include any number of layers, e.g., one, two, three, four, etc. Each layer of the multilayer laminate may include a polymer having the same polymer chain orientation or a different orientation from another layer. For example, referring to FIG. 71D, the multilayer laminate (2300) may include a first polymer layer (2302) with polymer chains having a −45 degree orientation, a second polymer layer (2304) with polymer chains having a +45 degree orientation, and a middle layer (2306) in which the polymer chains are in-line.

Alternatively, each layer of the multilayer laminate may include a polymer having the same ultimate tensile strength, or the layers may have different ultimate tensile strengths. The ultimate tensile strength of the polymer layers may range from about 25 MPa (megapascal) to about 400 MPa, including all values and sub-ranges therein. For example, the ultimate tensile strength of the layers may be about 25 MPa, about 50 MPa, about 75 MPa, about 100 MPa, about 125 MPa, about 150 MPa, about 175 MPa, about 200 MPa, about 225 MPa, about 250 MPa, about 275 MPa, about 300 MPa, about 325 MPa, about 350 MPa, about 375 MPa, or about 400 MPa. In one variation, the ultimate tensile strength may be greater than 150 MPa. In other variations, the layers may include the same biodegradable polymer. In further variations, the layers may include different biodegradable polymers. In yet further variations, the multilayer laminate may include a combination of one or more biodegradable polymer layers and one or more non-biodegradable polymer layers.

Figure 71E:
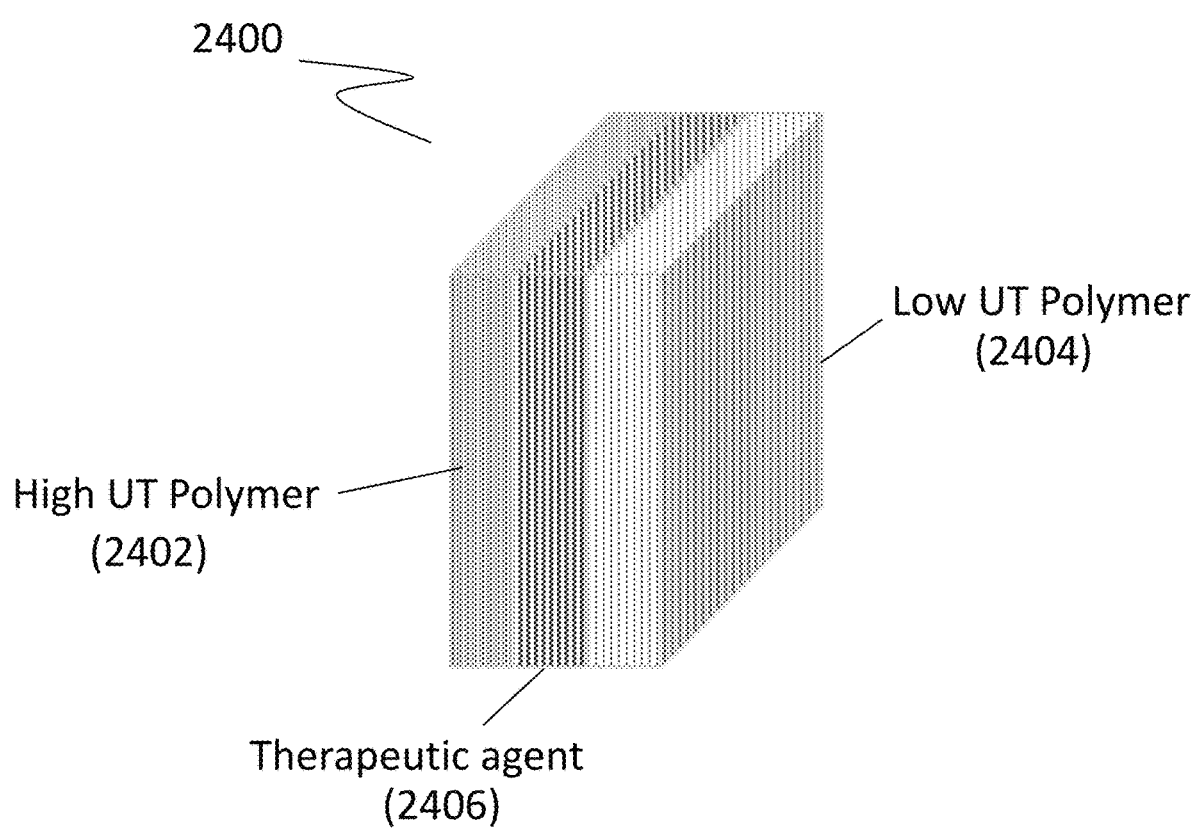
FIG. 71E depicts an exemplary multilayer polymer laminate made from layers having different ultimate tensile strengths and a layer containing a therapeutic agent.

One or more layers of the multilayer polymer laminate may include a therapeutic agent. For example, referring to FIG. 71E, the multilayer laminate (2400) may include a first polymer layer (2402) having a high ultimate tensile strength, a second polymer layer (2404) having a low ultimate tensile strength, and a middle layer (2406) including a therapeutic agent. The ultimate tensile strength of polymer layers having a high ultimate tensile strength may be greater than about 150 MPa. In some variations, high ultimate tensile strengths may range from about 175 MPa to about 400 MPa, including all values and sub-ranges therein. For example, high ultimate tensile strengths may be 175 MPa, about 200 MPa, about 225 MPa, about 250 MPa, about 275 MPa, about 300 MPa, about 325 MPa, about 350 MPa, about 375 MPa, or about 400 MPa. Exemplary therapeutic agents that may be contained in a polymer layer include without limitation, an antibacterial agent, an anti-inflammatory agent, a growth promoting agent, a hemostatic agent, a clot prevention agent, an analgesic, and combinations thereof. Exemplary antibacterial agents include without limitation, aminoglycosides, amphenicols, ansamycins, bacitracin, betalactams, β-lactams such as penicillins, lincosamides, macrolides, nitrofurans, quinolones, sulfonamides, sulfones, tetracyclines, vancomycin, and any of their derivatives, and combinations thereof. Examples of penicillins that can be suitable for use with the described devices and methods include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, cefazolin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin, and combinations thereof. Cephalosporins such as cefazolin or cephalexin may also be used. The anti-inflammatory agents that may be used with the described devices and methods include without limitation, steroids such as dexamethasone and hydrocortisone. Exemplary growth factors include without limitation, TGF-β (transforming growth factor-β), BMP-2 (bone morphogenetic protein-2), BMP-7 (bone morphogenetic protein-7), BMP-12 (bone morphogenetic protein-12), BMP-13 (bone morphogenetic protein-13), IGF-I (insulin growth factor-I), FGF-2 (fibroblast growth factor-2), FGF-4 (fibroblast growth factor-14), FGF-8 (fibroblast growth factor-8), FGF-18 (fibroblast growth factor-18), and PDGF (platelet-derived growth factor), VEGF (vascular endothelial growth factor), Wnt3a, Wnt7a, and combinations thereof.

When the tension element is formed from a biodegradable material, it may degrade over a period ranging from about three months to about twelve months. For example, the tension element may degrade over a period of about one month, about two months, three months, about four months, about five months, about six months, about seven months, about eight months, about nine months, about ten months, about eleven months, or about twelve months. In one variation, the tension element may degrade over a period ranging from about four months to about nine months. Depending on the material the tension element is made from, the loss of tensile strength may occur before complete degradation of the tensile element. In these variations, the tension element may be made from a material providing a sufficient amount of tensile strength over the desired time period.

When the tension element is non-biodegradable, it may be made from a non-biodegradable polymer or a metal. Exemplary non-biodegradable polymers include without limitation, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly (vinyl imidazole), chorosulphonated polyolefins, polyethylene oxide, silk, Nylon, polyamide, polypropylene, polyester, polybutester, and copolymers and blends thereof. Exemplary metals include, but are not limited to, platinum, silver, stainless steel, nickel, titanium, and alloys thereof.

The tension element may be formed to have any suitable cross-sectional shape. For example, the cross-sectional shape (without any anchors included) may be circular, semi-circular, ovular, rectangular, square, or triangular. When rectangular in cross-section, the width and thickness of the tension element may range from about 0.25 mm to about 1.5 mm, including all values and sub-ranges therein. For example, the width may be about 0.25 mm, about 0.5 mm, about 0.75 mm, about 1.0 mm, about 1.25 mm, or about 1.5 mm. In one variation, the width of the tension element may be about 0.65 mm. Similarly, the thickness of the tension element may be about 0.25 mm, about 0.5 mm, about 0.75 mm, about 1.0 mm, about 1.25 mm, or about 1.5 mm. In one variation, the thickness of the tension element may be about 0.7 mm.

The tension element including, for example, the distal anchor, proximal anchors, catch, distal toe, and/or any other tension element component may be die cut from one or more polymer materials, as described above. In other variations, the tension element or any component thereof, may be formed by injection molding, three-dimensional (3D) printing, or other additive manufacturing techniques (e.g., other techniques that use computer-aided design software or 3D object scanners).

The tension element may be configured to hold or maintain a force on a target tissue. The force may be a tension force ranging from about 4.0 Newtons to about 70 Newtons, including all values and sub-ranges therein, which may be generated by pulling on the free proximal end of the tension element after the distal anchor has been fixed to the target tissue. For example, the tension force may be about 4.0 Newtons, about 5.0 Newtons, about 10 Newtons, about 15 Newtons, about 20 Newtons, about 25 Newtons, about 30 Newtons, about 35 Newtons, about 40 Newtons, about 45 Newtons, about 50 Newtons, about 55 Newtons, about 60 Newtons, about 65 Newtons, or about 70 Newtons. Tensile strength of the tension element may range from about 100 MPa to about 800 Mpa, including all values and sub-ranges therein. For example, the tensile strength may be about 100 Mpa, about 110 Mpa, about 120 Mpa, about 130 Mpa, about 140 Mpa, about 150 Mpa, about 155 Mpa, about 160 Mpa, about 165 Mpa, about 170 Mpa, about 175 Mpa, about 180 Mpa, about 185 Mpa, about 190 Mpa, about 195 Mpa, about 200 Mpa, about 210 Mpa, about 220 Mpa, about 230 Mpa, about 240 Mpa, about 250 Mpa, about 260 Mpa, about 270 Mpa, about 280 Mpa, about 290 Mpa, about 300 Mpa, about 350 Mpa, about 400 Mpa, about 450 Mpa, about 500 Mpa, about 550 Mpa, about 600 Mpa, about 650 Mpa, about 700 mPa, about 750 Mpa, or about 800 Mpa. In some instances, the tensile strength of the tension element may be at least about 150 Mpa. In other instances, the tensile strength of the tension element may be at least about 300 Mpa.

The total length of the tension element prior to delivery may vary depending on the target tissue of deployment, type of procedure being performed, and/or the anatomy of the subject. Total tension element length prior to delivery may range from about 10 cm to about 30 cm, including all values and sub-ranges therein. For example, the total length may be about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm, or about 30 cm. In one variation, the tension element may have a total length of about 15 cm prior to delivery. Once delivered to the target tissue, the tension element may be trimmed to a length that applies an appropriate amount of force, reshaping, etc., to the target tissue. The longer length may help facilitate handling of the tension element while the target tissue is being manipulated.

The length of the tension element between the distal anchor and a most distally positioned proximal anchor ranges from about 10 mm to about 25 mm, including all values and sub-ranges therein. For example, this length may be about 10 mm, about 15 mm, about 20 mm, or about 25 mm. The length may be adjusted to be longer or shorter depending on the tissue to be manipulated. Lengths between about 10 mm to about 25 mm may be useful when the nasal septal cartilage is to be manipulated.

The length of the tension element between the needle at the proximal end of elongate body and the most proximally positioned proximal anchor ranges from about 50 mm to about 70 mm, including all values and sub-ranges therein. For example, this length may be about 50 mm, about 55 mm, about 60 mm, about 65 mm, or about 70 mm. The tension element may or may not include any proximal anchors along this length. Additionally, the tension element may be trimmed to a final length along this length.

Anchors

The devices described herein may include a distal anchor at the distal end of the tension element. The distal anchor may have an insertion configuration and a deployed configuration. Additionally, the distal anchor may include an anchor body and a pivot point. Upon application of force to the elongate body of the tension element, the distal anchor may be configured to swivel, flex, expand, rotate, flare, or pivot about a pivot point to transform from the insertion configuration to the deployed configuration. This applied force is generally in the direction opposite to the direction of insertion. In some instances, the longitudinal axis of the distal anchor in its deployed configuration may be orthogonal to the longitudinal axis of the tension element. However, the distal anchor may swivel about the pivot point in any suitable amount to achieve a deployed configuration. The distal anchor may swivel about the pivot point at a swivel angle ranging from about 30 degrees to about 90 degrees with respect to the longitudinal axis of the tension element, including all values and sub-ranges therein. For example, the swivel angle may be about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees.

The distal anchor may be variously sized and shaped. In general, the distal anchor in its deployed configuration prevents passage of the distal end of the tension element back though tissue. The distal anchor may have a rounded cone shape, and a length ranging from about 0.5 mm to about 15 mm, including all values and sub-ranges therein, and a width ranging from about 0.5 mm to about 5.0 mm, including all values and sub-ranges therein. For example, the distal anchor length may be about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, about 10 mm, about 10.5 mm, about 11.0 mm, about 11.5 mm, about 12.0 mm, about 12.5 mm, about 13.0 mm, about 13.5 mm, about 14.0 mm, about 14.5 mm, or about 15 mm. The width of the distal anchor may be about 0.5 mm, about 1.0 mm, about 1.5 mm, about 2.0 mm, about 2.5 mm, about 3.0 mm, about 3.5 mm, about 4.0 mm, about 4.5 mm, or about 5.0 mm.

Figure 83A:
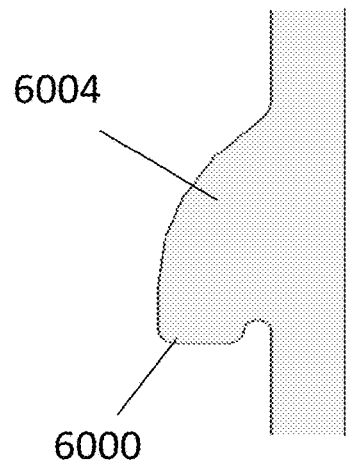
FIGS. 83A-83D depict other exemplary distal anchor configurations.
Figure 83B:
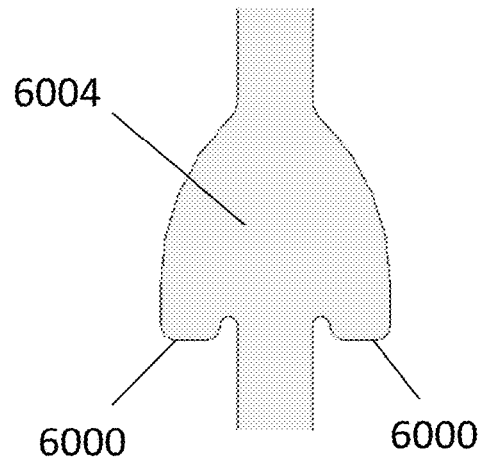
Figure 83C:
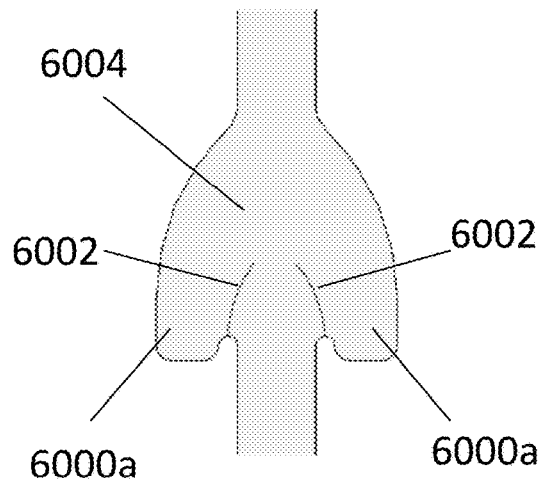
Figure 83D:
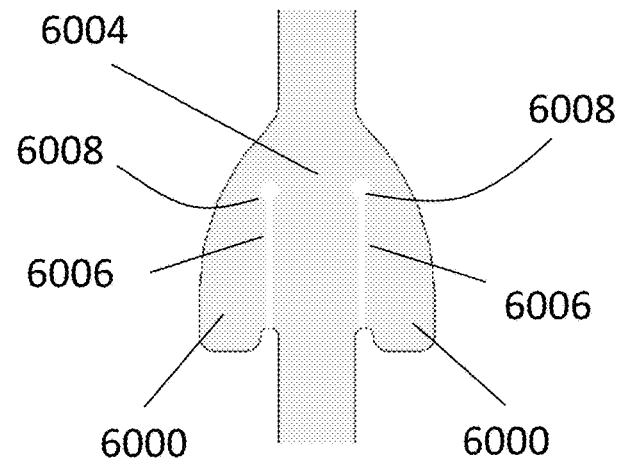

The anchor body may include a single arm or a plurality of arms. The arm(s) may have varying shapes and geometries. In some variations, the single arm or the plurality of arms may be configured to swivel (e.g., flex, rotate, pivot) about a pivot point upon the application of force to the elongate body. Any suitable number of arms may be employed. For example, two, three, or four arms may be included. For example, referring to FIGS. 83A to 83D, the anchor body (6004) may include one arm (6000) (FIG. 83A) or two arms (6000) (FIG. 83B). When the anchor body (6004) is configured with longer arms, curved cuts (6002) may be made within the body (6004) to form curved arms (6000*a*) (FIG. 83C), or the arms (6000) may be formed by linear cuts (6006) terminating in a distal hole (6008) (83D).

When the anchor body includes two arms and is configured to swivel about a pivot point, the distal anchor (e.g., anchor 1208 in FIGS. 43 and 44) may be referred to as a "Z-Flex anchor". The body of the Z-Flex anchor may have a width ranging from about 0.5 mm to about 5.0 mm, including all values and sub-ranges therein. For example, the Z-Flex anchor body may have a width of about 0.5 mm, about 1.0 mm, about 1.5 mm, about 2.0 mm, about 2.5 mm, about 3.0 mm, about 3.5 mm, about 4.0 mm, about 4.5 mm, or about 5.0 mm. In one variation, the Z-Flex anchor body has a width of about 2.5 mm. Furthermore, the Z-Flex anchor body may have a length ranging from about 0.5 mm to about 15 mm, including all values and sub-ranges therein. For example, the length of the Z-Flex anchor body may be about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, or about 15 mm. In one variation, the Z-Flex anchor body has a length of about 2.75 mm. The arms of the Z-Flex anchor body may also have a length and width. In one variation, the arm length may be about 1.5 mm and the width about 0.5 mm. The arm length may range from about 0.5 mm to about 3.0 mm, including all values and sub-ranges therein. For example, the arm length may be about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, ab out 2.2 mm, about 2.3 mm, about 2.4 mm, about 2.5 mm, about 2.6 mm, about 2.7 mm, about 2.8 mm, about 2.9 mm, or about 3.0 mm. The arm width may range from about 0.5 mm to about 2.0 mm, including all values and sub-ranges therein. For example, the arm width may be about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm. In some variations, it may be useful for the arm width to be about one third of the width of the Z-Flex anchor body. In other variations, it may be useful for the arm width to be about 70% to about 80% of the width of the tension element, including all values and sub-ranges therein, so that the distal anchor may have a holding force of greater than about 1 Newton (N). For example, it may be useful for the arm width to be about 70%, about 71%, about 72%, about 73%, about 74% about 75%, about 76%, about 77%, about 78%, about 79%, or about 80% of the width of the tension element. In one variation, the arm width may be about 0.5 mm when the tension element has a width of about 0.65 mm. In some variations, the distal anchor may provide a holding force of at least about 13 N to provide an overall tension element holding force ranging between about 5 N to about 30 N, including all values and sub-ranges therein. For example, the holding force of the distal anchor may be such that the overall force (holding force of the distal anchor and proximal anchors) of the tension element is about 5 N, about 6 N, about 7 N, about 8 N, about 9 N, about 10 N, about 11 N, about 12 N, about 13 N, about 14 N, about 15 N, about 16 N, about 17 N, about 18 N, about 19 N, about 20 N, about 21 N, about 22 N, about 23 N, about 24 N, about 25 N, about 26 N, about 27 N, about 28 N, about 29 N, or about 30 N.

Figure 67:
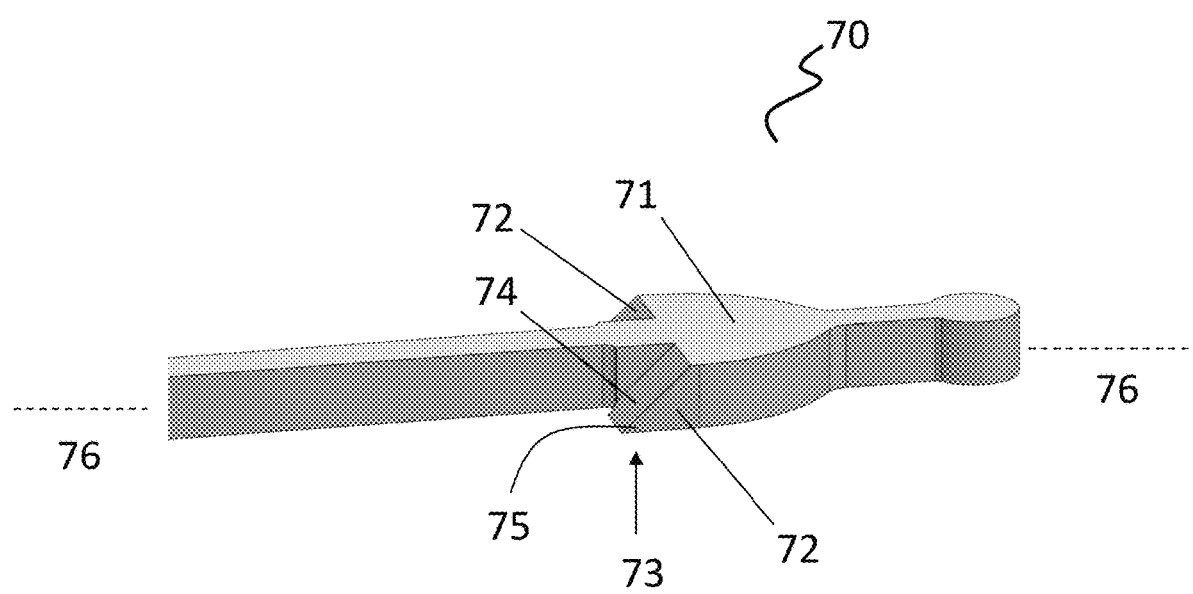
FIG. 67 depicts an exemplary distal anchor having arms with beveled distal ends.

One or more arms of the plurality of arms of the anchor body may include a distal end that is bevel cut to form a slope that may help swivel the distal anchor at the pivot point and facilitate its engagement against tissue. The bevel may be cut through the entire thickness of each arm. The angle of the bevel may range from about 15 degrees to about 75 degrees, including all values and sub-ranges therein. For example, the bevel angle may be about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, or about 75 degrees. In one variation, the bevel angle is about 45 degrees. Referring to FIG. 67, an exemplary distal anchor (70) is shown including an anchor body (71) and a plurality of arms (72). A distal end (73) of each of the arms (72) is bevel cut to form a sloping surface (74). A bevel angle (75) may be formed at the point where the sloping surface (74) intersects the longitudinal axis (76) of the distal anchor (70). In some variations, the distal anchor may be a Z-Flex anchor comprising two arms, where each of the two arms includes a distal end having a bevel angle of about 45 degrees.

Alternatively, the anchor body may be rectangular, square, triangular, circular, or ovular in shape. The anchor body may also be diamond-shaped, or shaped like an arrow or a dog bone. In some variations, the anchor body may include a heel and a toe retainer. In other variations, the anchor body may be expandable from a collapsed configuration to an expanded configuration. Here the collapsed configuration may allow insertion of the distal anchor through tissue in a first direction, and the expanded configuration prevent passage of the distal anchor back through the tissue in a second direction, e.g., in a direction opposite to the first direction.

A plurality of proximal anchors (e.g., migration prevention elements) may further be disposed between the distal anchor and the proximal end of the tension element. The distal anchor and the plurality of proximal anchors may be the same type of anchor or different types of anchors. In general, the proximal anchors are sized to be smaller than the distal anchor, but may be the same size if desired. Any suitable number of proximal anchors may be employed. The number of proximal anchors provided between the distal anchor and the proximal end of the elongate body may range from 2 to 40. For example, the plurality of proximal anchors may include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 anchors. The length of the tension element including the proximal anchors may be about 75 mm. Spacing between the plurality of proximal anchors may be the same or different. When the spacing is uniform between the plurality of proximal anchors, the length of the space may be between about 0.5 mm to about 5.0 mm, including all values and sub-ranges therein. For example, the length of the space may be about 0.5 mm, about 1.0 mm, about 1.5 mm, about 2.0 mm, about 2.5 mm, about 3.0 mm, about 3.5 mm, about 4.0 mm, about 4.5 mm, or about 5.0 mm. In some variations, the length of the space may be about 2.0 mm. In some variations, the length of the space may be about 3.0 mm. Spacing between the distal anchor and most distal proximal anchor may be about 10 mm. In one variation, the plurality of proximal anchors comprise Z-Flex anchors. Here the arms of the Z-Flex anchor may have a length ranging from about 0.25 mm to about 1.25 mm. For example, the arms may have a length of about 0.25 mm, about 0.50 mm, about 0.75 mm, about 1.0 mm, or about 1.25 mm. The arms of the Z-Flex anchor may have a width of about 0.6 mm. In some variations, the plurality of proximal anchors may provide a holding force of at least about 6 N to provide an overall tension element holding force ranging between about 5 N to about 30 N, including all values and sub-ranges therein. For example, the holding force of the proximal anchors may be such that the overall force (holding force of distal anchor and proximal anchors) of the tension element is about 5 N, about 6 N, about 7 N, about 8 N, about 9 N, about 10 N, about 11 N, about 12 N, about 13 N, about 14 N, about 15 N, about 16 N, about 17 N, about 18 N, about 19 N, about 20 N, about 21 N, about 22 N, about 23 N, about 24 N, about 25 N, about 26 N, about 27 N, about 28 N, about 29 N, or about 30 N.

Figure 69:
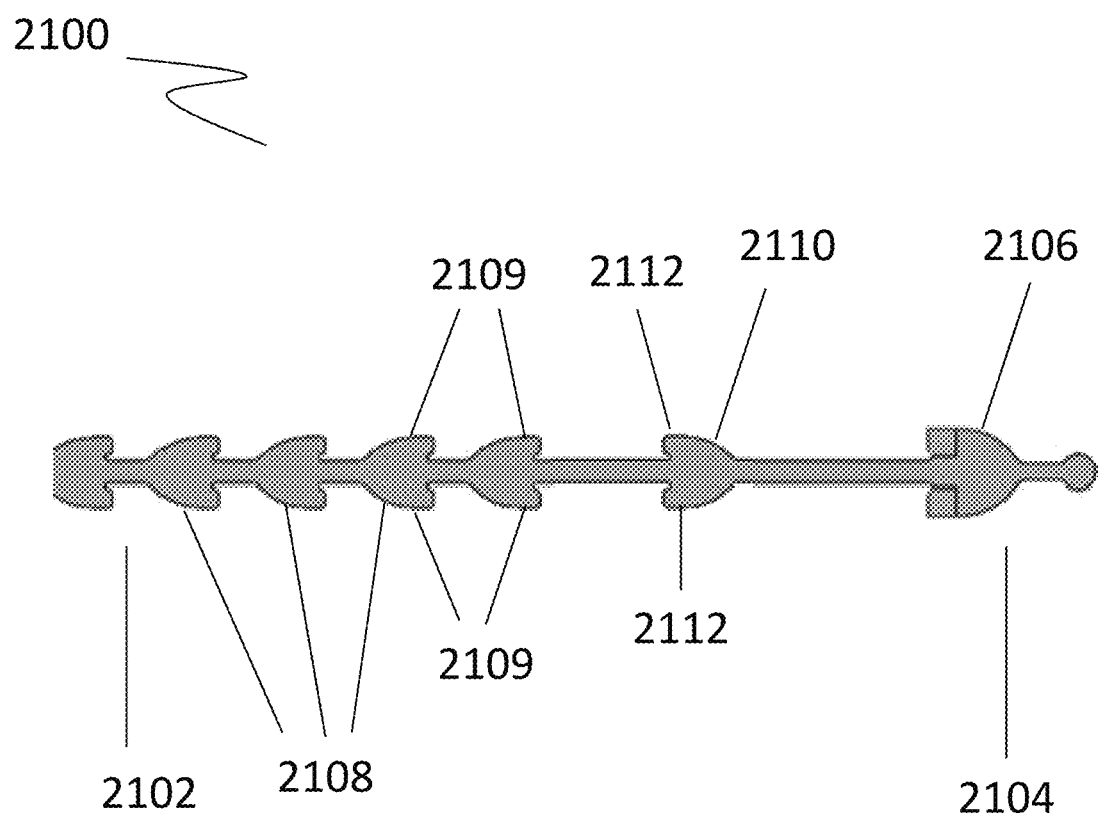
FIG. 69 depicts another exemplary tension element including a catch configured to assist with decoupling the distal anchor from the delivery device.

A catch may be provided between the distal anchor and the plurality of proximal anchors that may be configured to assist with decoupling (e.g., releasing or detaching) the distal anchor from a delivery device. In one variation, the catch may have a body and a plurality of arms like the proximal anchors described above, but the plurality of arms may be configured to face in a direction opposite to that of the arms of the proximal anchors. In other words, if the plurality of arms of the proximal anchors face the distal end of the tension element, the plurality of arms of the catch may face the proximal end of the tension element. For example, referring to FIG. 69, the tension element (2100) has a proximal end (2102) and a distal end (2104). A distal anchor (2106) may be disposed at the distal end (2104), and a plurality of proximal anchors (2108) may be disposed along the proximal end (2104) of the tension element (2100). Each proximal anchor (2108) includes a plurality of arms (2109) that face the distal end (2104) of the tension element (2100). A catch (2110) provided between the distal anchor (2106) and the plurality of proximal anchors (2108) may include a plurality of arms (2112) that face the proximal end (2102) of the tension element (2100).

Figure 70:
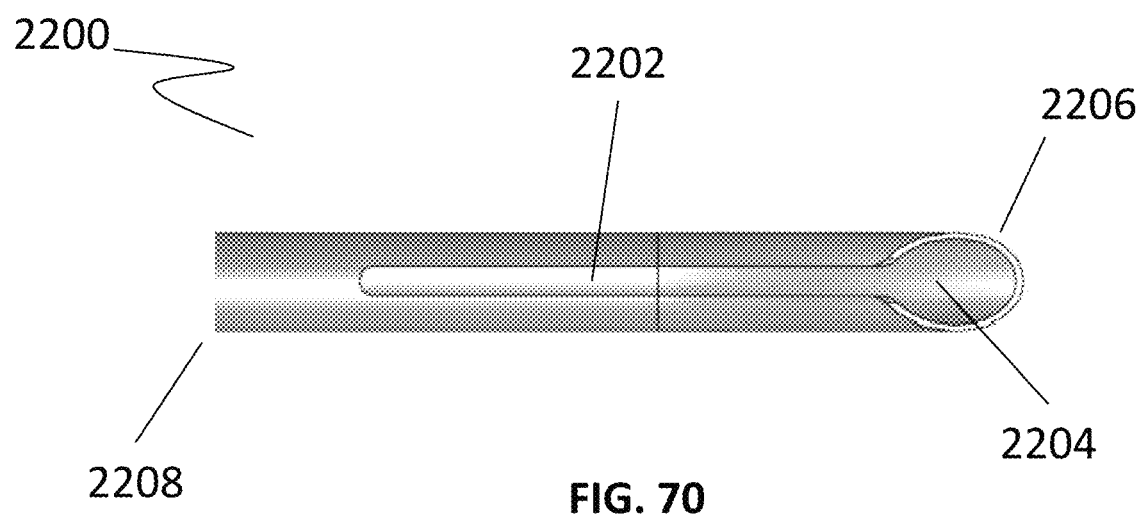
FIG. 70 depicts an exemplary delivery device cannula including a channel to assist with decoupling the distal anchor from the delivery device.

The catch may help to decouple (e.g., release or detach) the distal anchor of the tension element from the delivery device, as previously stated. For example, when the cannula of a delivery device includes a channel at least partially extending between an opening in the cannula tip and a proximal end of the cannula, the channel may be used to at least partially engage the catch during withdrawal of the cannula from tissue and provide an amount of slack in the tension element that facilitates release of the distal anchor. The channel may also help to facilitate release of the proximal needle or help a straight proximal needle pass through a curved portion of the cannula. The length of the channel may range from about 5.0 mm to about 25 mm, including all values and sub-ranges therein. For example, the channel length may be about 5.0 mm, about 6.0 mm, about 7.0 mm, about 8.0 mm, about 9.0 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. In some variations, it may be useful for the channel length to be about 13 mm, about 14 mm, or about 15 mm. The width of the channel may range from about 0.5 mm to about 2.0 mm, including all values and sub-ranges therein. For example, the channel width may be about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm. In some variations, it may be useful for the channel width to be about 1.25 mm. An exemplary cannula (2200) including a channel (2202) at least partially extending between an opening (2204) in the cannula tip (2206) and a proximal end (2208) of the cannula (2200) is shown in FIG. 70.

An enlarged tip (toe) may also be provided at the distal end of the tension element distal to the distal anchor to further facilitate anchoring of the tension element to tissue and/or coupling to an anchor delivery element, as further described below. The distal anchor, enlarged tip, catch, and plurality of proximal anchors may be made from the same material as the tension element, or from different materials. In some variations, the distal anchor may be made from a non-biodegradable material, and the plurality of proximal anchors made from a biodegradable material, for example, a biodegradable polymer. Exemplary biodegradable polymers include without limitation, LPLA (Poly(L-lactide)), DLPLA (Poly(DL-lactide)), LDLPLA (Poly(DL-lactide-co-L-lactide)), LPLA-HA (Poly(L-lactide) with hydroxylapatite), PGA (Poly(glycolide)), PGA-TMC (Poly(glycolide-co-trimethylene carbonate) or polyglyconate), PDO (Poly(dioxanone)), LPLG (Poly(L-lactide-co-glycolide)), DLPLG (Poly(DL-lactide-co-glycolide), or copolymers or blends thereof. Additional exemplary biodegradable polymers include polylactides, poly(orthoesters), poly(phosphoester)s, polyphosphazenes, polyanhydrides, polycaprolactones, polyurethanes, polycarbonates, chitosan, cyclodextrin, dextran, hyaluronic acid, chondroitin sulfate, dermatan sulfate, heparin, heparin sulfate, keratan sulfate, or copolymers or blends thereof. In some variations, the distal anchor, enlarged tip, and plurality of proximal anchors may be made from PDO (Poly(dioxanone)). Non-biodegradable materials may include a non-biodegradable polymer or a metal. Exemplary non-biodegradable polymers include without limitation, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof. Exemplary metals include, but are not limited to, stainless steel, nickel, titanium, magnesium, and alloys thereof. Instead of using a distal anchor, in some variations, the distal end of the tension element is configured to be rotated or screwed into tissue and/or bone to anchor it in place within a target tissue.

The tension element, distal anchor, enlarged tip, and plurality of proximal anchors may be provided with a coating. In some variations, the coating may include an antibacterial agent. Exemplary antibacterial agents include without limitation, aminoglycosides, amphenicols, ansamycins, betalactams, β-lactams such as penicillins, lincosamides, macrolides, nitrofurans, quinolones, sulfonamides, sulfones, tetracyclines, vancomycin, and any of their derivatives, or combinations thereof. Examples of penicillins that can be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, 35 longate35 in, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

In other variations, the coating may include growth factors that promote cartilage remodeling. Exemplary growth factors include without limitation, TGF-β1 (transforming growth factor-β), BMP-2 (bone morphogenetic protein-2), BMP-7 (bone morphogenetic protein-7), IGF-I (insulin growth factor-I), FGF-2 (fibroblast growth factor-2), FGF-18 (fibroblast growth factor-18), and PDGF (platelet-derived growth factor).

In further variations, the coating may include a hydrophobic polymer to slow the degradation of the tension element. Examples of hydrophobic polymers that may be used to form the coating include, but are not limited to, fluoropolymers such as polytetrafluoroethylene (PTFE) and expanded polytetrafluoroethylene (ePTFE), polyvinyl chloride (PVC), polyvinylacetate, poly(ethylene terephthalate), silicone, polyesters, polyamides, polyureas, styrene-block copolymers, polymethyl methacrylate, acrylic-butadiene-styrene copolymers, polyethylene, polystyrene, polypropylene, natural and synthetic rubbers, acrylonitrile rubber, and mixtures and copolymers of any of the foregoing.

In yet further variations, the coating may include a vasoconstrictive agent. Examples of vasoconstrictive agents include without limitation, epinephrine, levonordefrin, and adrenaline. In some variations, the coating may include a decongestant. Exemplary decongestants include, but are not limited to, epinephrine, pseudoephedrine, oxymetazoline, phenylephrine, tetrahydrozolidine, and xylometazoline. The coating may also include an anti-inflammatory agent. Exemplary anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Needles and Anchor Delivery Elements

The devices described herein may further include a proximal needle removably attached to the proximal end of the elongate body of the tension element. The proximal needle may be a cutting needle having a length ranging from about 5.0 mm to about 25 mm, including all values and sub-ranges therein. For example, the proximal needle may have a length of about 5.0 mm, about 10 mm, about 15 mm, about 20 mm, or about 25 mm. In one variation, the proximal needle has a length of about 13 mm. Proximal needle diameters may range from about 0.4 mm to about 2.0 mm, including all values and sub-ranges therein. For example, the proximal needle diameter may be about 0.4 mm, about 0.5 mm, about 1.0 mm, about 1.5 mm, or about 2.0 mm. In one variation, the proximal needle diameter is about 1.0 mm. In another variation, the proximal needle diameter is about 1.5 mm.

The proximal needle may be used to place or manipulate the proximal end of the elongate body through or around tissue, and may be removably attached in various ways to the tension element. For example, the proximal needle may be removable attached to the tension element by swaging or crimping, or by threading the tension element through a portion of the proximal needle. In some variations, the proximal needle is a quick-thread needle. In other variations, the proximal needle may be swaged to a loop of material, e.g., PDO (Poly(dioxanone)), which may then be coupled to the tension element.

At the distal end of the tension element, an anchor delivery element may be coupled to the distal anchor. The anchor delivery element may include a cutting tip configured to pass the distal anchor through the tissue in its insertion configuration. The anchor delivery element may be made from various metals, including but not limited to, stainless steel, spring steel, and nitinol. In some variations, the anchor delivery element may include a keyhole shaped to removably couple the distal anchor to the anchor delivery element. For example, the keyhole may be dimensioned to keep the distal anchor coupled to the anchor delivery element during tissue insertion but allow disengagement of distal anchor during withdrawal of the anchor delivery element back through the tissue.

In other variations, the anchor delivery element may include a tip component configured to cut and/or pierce tissue and an anchor support. The tip component may include a cutting tip, a cockpit or pocket shaped to removably secure the enlarged distal end of the tension element (toe), a clip region that removably secures the region of the tension element between the toe and distal anchor to the anchor delivery element, and a seating region upon which the distal anchor may be positioned prior to deployment. In one variation, the tip component and the anchor support may comprise different components that are joined to form the anchor delivery element. In other variations, the tip component and anchor support may be integrally formed as a single piece. Materials that may be used to make the tip component and the anchor support include without limitation, stainless steel, spring steel, and nitinol. The tip component and anchor support may comprise the same metal material or different metal materials. For example, in some variations, the tip component may be made from stainless steel, and the anchor support made from nitinol.

Figure 87A:
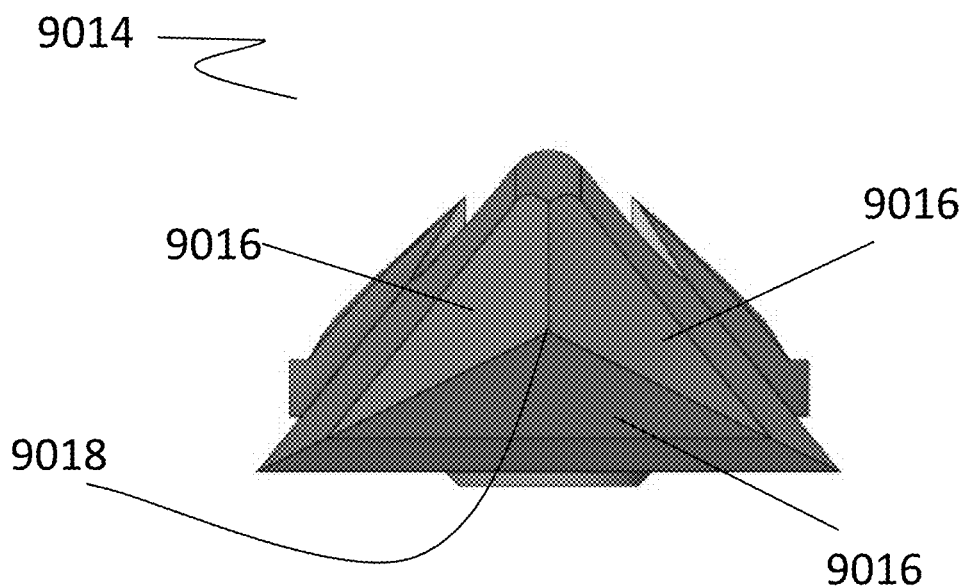
FIGS. 87A and 87B depict exemplary variations of cutting tip geometries.
Figure 87B:
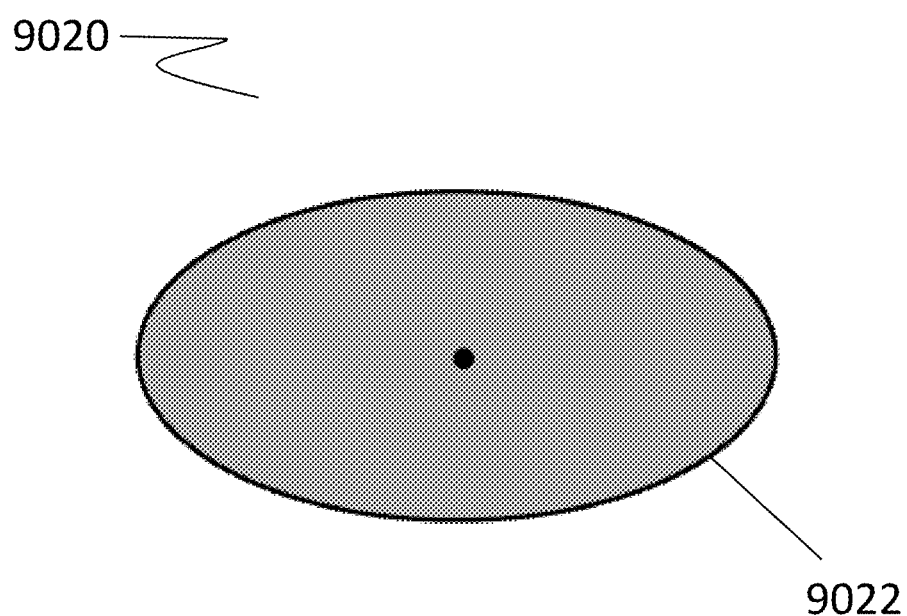

When the tip component and anchor support are separate components, they may be joined to form the anchor delivery element via one or more rivets. Alternatively, the tip component and anchor support may be joined by crimping, welding, or riveting. The tip component may be made by processes such as laser sintering, injection molding, or machining. In some variations, as shown by the end view provided in FIG. 87A, the tip component (9014) may be formed to include three sharp edges (9016) that taper to a point. In other variations, as shown by the cross-sectional end view provided in FIG. 87B, the tip component (9020) may have an ovular cross-sectional shape (9022), which may be useful for piercing instead of cutting tissue.

Furthermore, the tip component may be formed such that it or the distal anchor does not have any leading edges that may catch on tissue during delivery to a target tissue. For example, the anchor delivery element and distal anchor of the tension element may form a level surface that may prevent the distal anchor from catching on tissue during insertion. In some instances, disengagement of the distal anchor from the seating region may be accomplished using a release tab. For example, referring to FIG. 55, a distal anchor (5000) including a release tab (5006) is shown seated in a seating region of the anchor delivery element.

Figure 43:
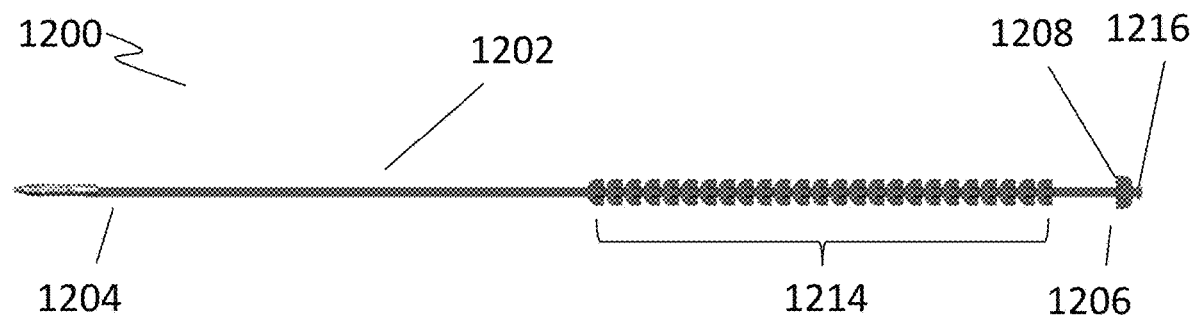
FIG. 43 depicts a top view of another exemplary tension element including a distal anchor having arms that swivel from an insertion configuration to a deployed configuration.
Figure 44:
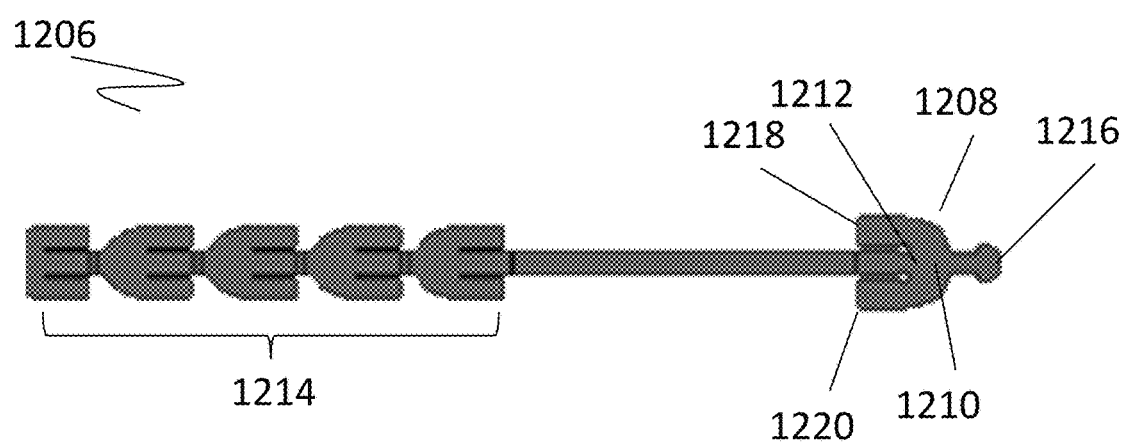
FIG. 44 depicts an enlarged view of the distal end of the tension element shown in FIG. 43.
Figure 56:
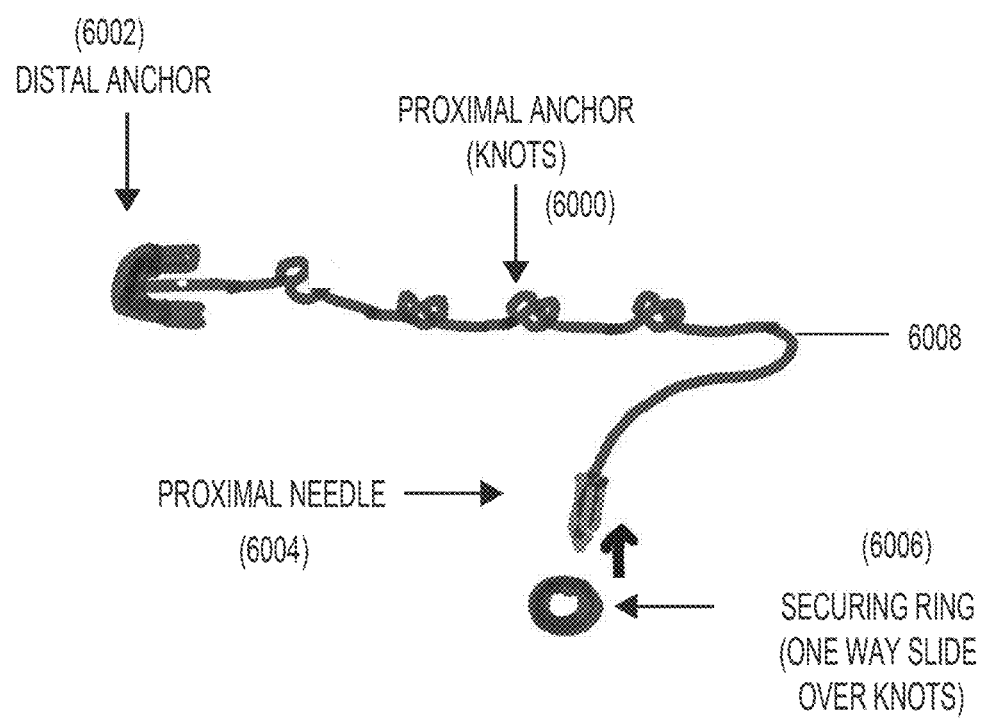
FIG. 56 depicts another exemplary tension element including a plurality of knots as the proximal anchors.

The tension elements described herein may have various configurations. Referring to FIG. 43, an exemplary tension element is shown. Tension element (1200) may include an elongate body (1202) having a proximal end (1204) and a distal end (1206). A distal anchor, such as Z-Flex anchor (1208), may be disposed at the distal end (1206) of the elongate member (1202). As shown in the enlarged view of the distal end (1206) in FIG. 44, Z-Flex anchor (1208) includes an anchor body (1210), a pivot point (1212), and a first arm (1218) and a second arm (1220). A plurality of proximal anchors (1214) may also be disposed between the distal Z-Flex anchor (1208) and the proximal end (1204) of the tension element (1202) to help prevent migration of the tension element (1200) once deployed in a tissue. The plurality of proximal anchors (1214) may also be Z-Flex anchors that are facing in a direction opposite to that of the distal Z-Flex anchor (1208). An enlarged distal end (toe) (1216) may also be provided distal to the Z-Flex anchor (1208) to couple the Z-Flex anchor to an anchor delivery element (not shown) for deployment into tissue. At the proximal end (1204), a needle (1201) may be removably attached to the elongate body (1202). After deployment of the Z-Flex anchor into tissue, the needle (1201) may be used to place or manipulate the proximal end (1204) of the elongate body (1202) through or around tissue. In another variation, as shown in FIG. 56, the plurality of proximal anchors may be a plurality of knots (6000). In this variation, the distal anchor may be a Z-Flex anchor (6002). To apply a tension force to the tension element (6008), the proximal needle (6004) may thread through a securing feature such as a ring (6006) placed on a tissue surface, which is configured to slide in a single direction over the plurality of knots (6000).

Figures 45A, 45B:
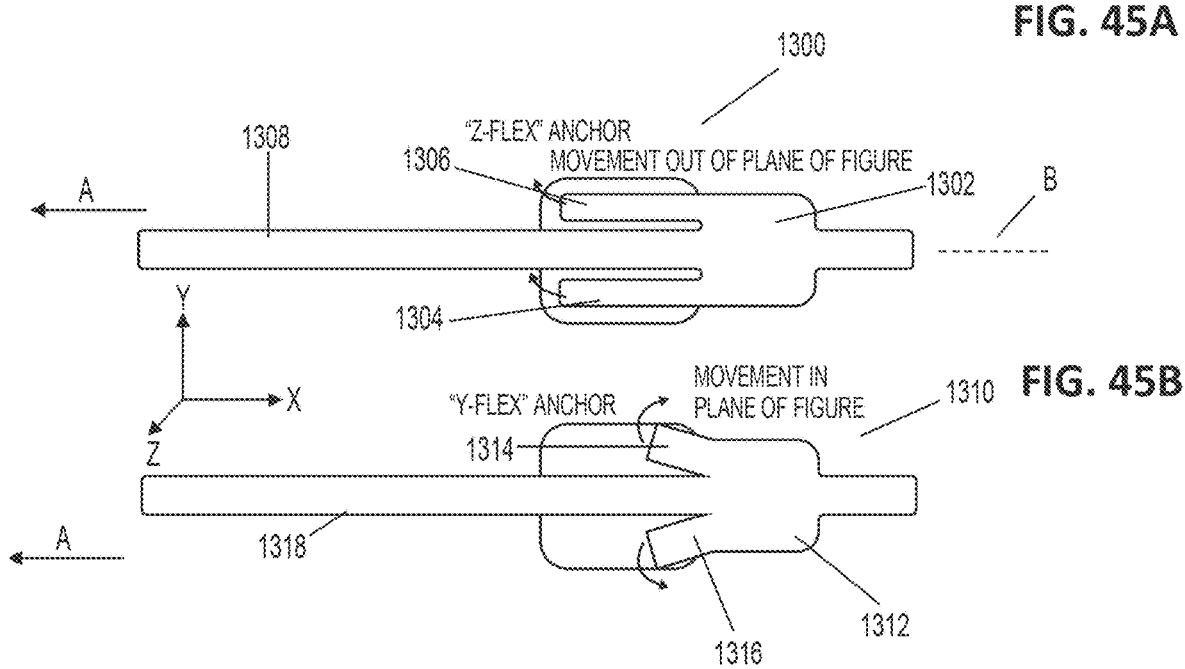
FIG. 45A depicts a top view of exemplary Z-Flex anchor.
FIG. 45B depicts a top view of an exemplary Y-Flex anchor.

Once inserted into tissue, the application of a force to the elongate body of the tension element may swivel or flex the arms of the Z-Flex anchor to transform the anchor from the insertion configuration to the deployed configuration. As shown in FIG. 45A, Z-Flex anchor (1300) includes an anchor body (1302) and a first arm (1304) and a second arm (1306). Upon the application of force to the tension element (1308) in the direction of arrow A, which is in a direction opposite to the direction of device insertion, the first and second arms (1304, 1306) swivel out of plane along the z-axis and orthogonal to the axis (B) of the tension element. In the deployed configuration, passage of the Z-Flex anchor (1300) back through tissue is prevented. In some variations, each arm of the plurality of arms of the anchor body may include a distal end that is bevel cut to form a slope that may help swivel the distal anchor at the pivot point and facilitate its engagement against tissue. In other variations, one arm of the plurality of arms may be bevel cut.

In another variation, as shown in FIG. 45B, the distal anchor, Y-Flex anchor (1310) includes an anchor body (1312) having a first arm (1314) and a second arm (1316). However, instead of swiveling out of plane upon the application of force to the tension element (1318) in the direction of arrow (A), the first and second arms (1314, 1316) swivel or flex in plane to prevent passage of the Y-Flex anchor (1310) back through tissue.

Figure 46:
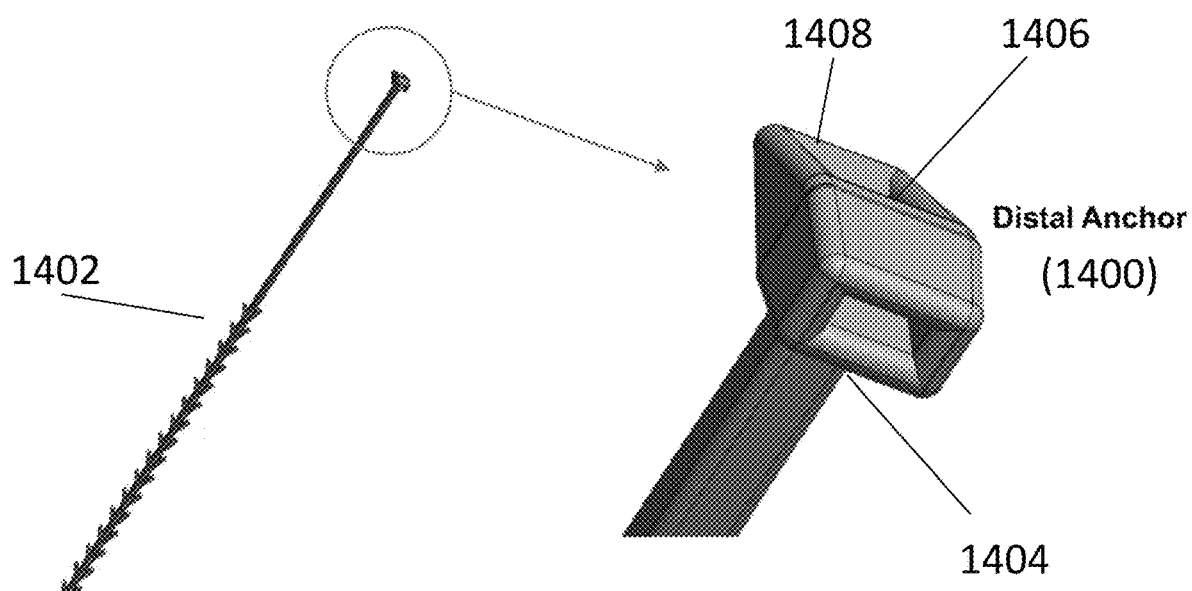
FIG. 46 depicts another exemplary distal anchor that swivels from an insertion configuration to a deployed configuration.
Figure 47A:
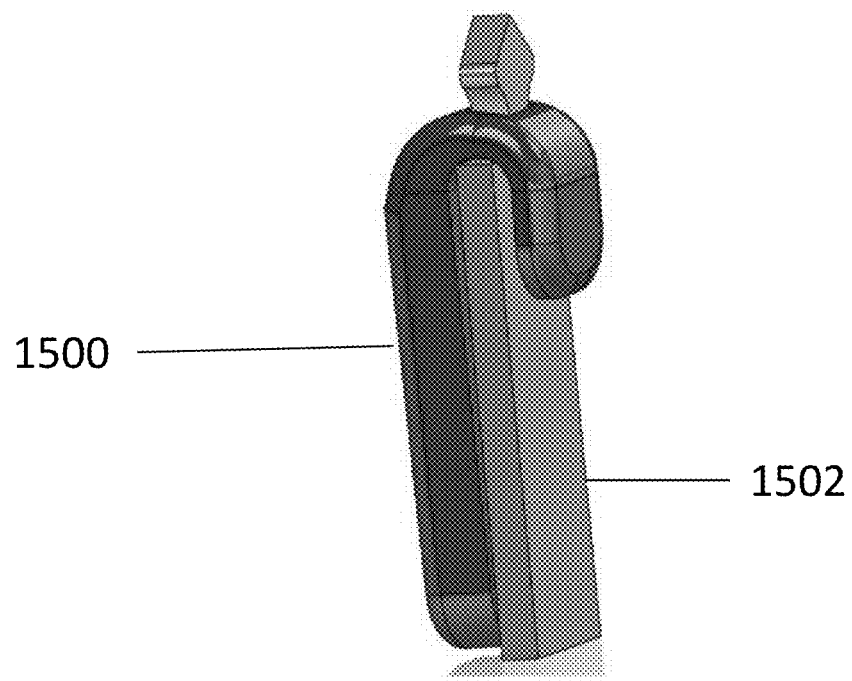
FIGS. 47A and 47B depict a further variation of a distal anchor.
Figure 47B:
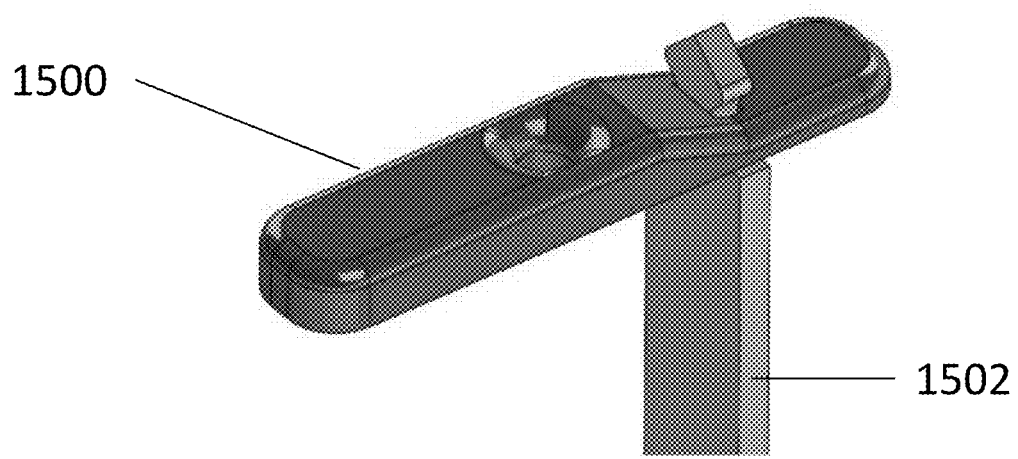

Further variations of distal anchors configured to swivel in order to transform from an insertion configuration to a deployed configuration are shown in FIGS. 46, FIGS. 47A and 47B, FIGS. 48A-48E, and FIGS. 49A-49D. Referring to FIG. 46, the distal anchor (1400) may be disposed at the distal end of tension element (1402) at pivot point (1404). Distal anchor (1400) may comprise a component (1406) designed to interface with or received an anchor delivery element (not shown). The component (1406) may have a tapered portion (1408) to facilitate insertion through tissue. In FIGS. 47A and 47B, the distal anchor includes a flexible body (1500) folded upon an anchor delivery element (1502) and coupled thereto by manual insertion of an engagement feature. The anchor is released by interaction with the tissue providing sufficient force to dislodge the distal anchor.

Figure 48A:
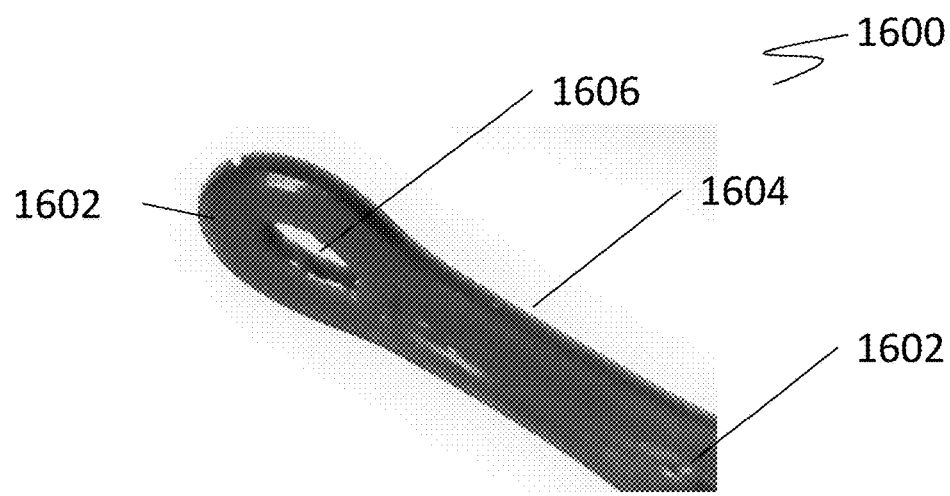
FIGS. 48A-48E depict another exemplary distal anchor shaped like a dog bone and its deployment through tissue.

In FIGS. 48A-48E, a distal anchor shaped like a dog bone is shown. Referring to FIG. 48A, the dog bone (1600) may include two enlarged lobed ends (1602) connected by a thinner midsection (1604). The enlarged lobed ends (1602) each include an opening (1606). Although the opening is shown as circular in shape, it may have any suitable shape.

Figure 48B:
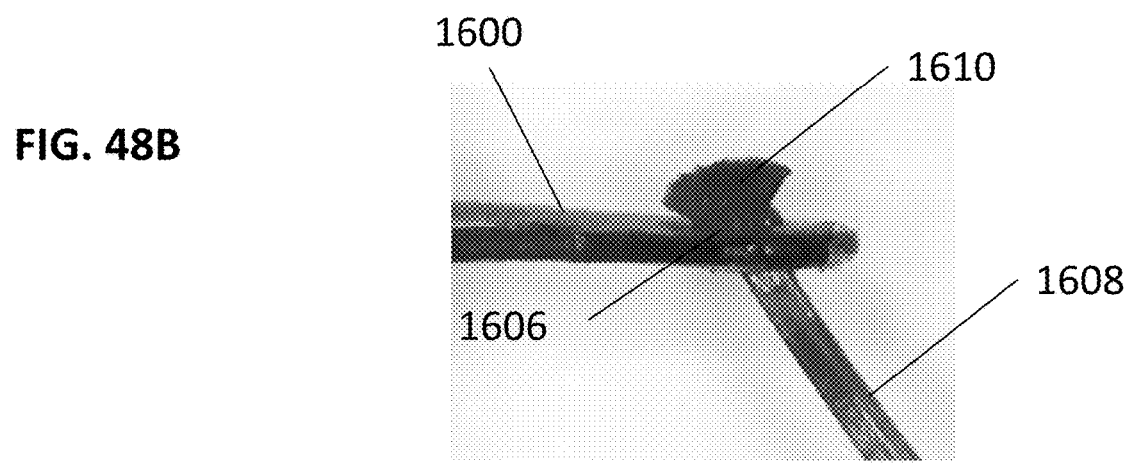
Figure 48C:
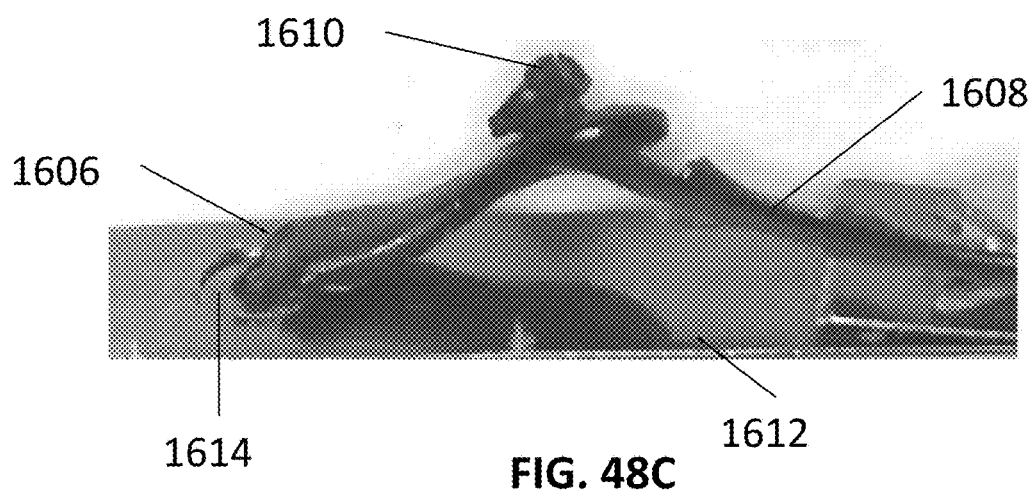
Figure 48D:
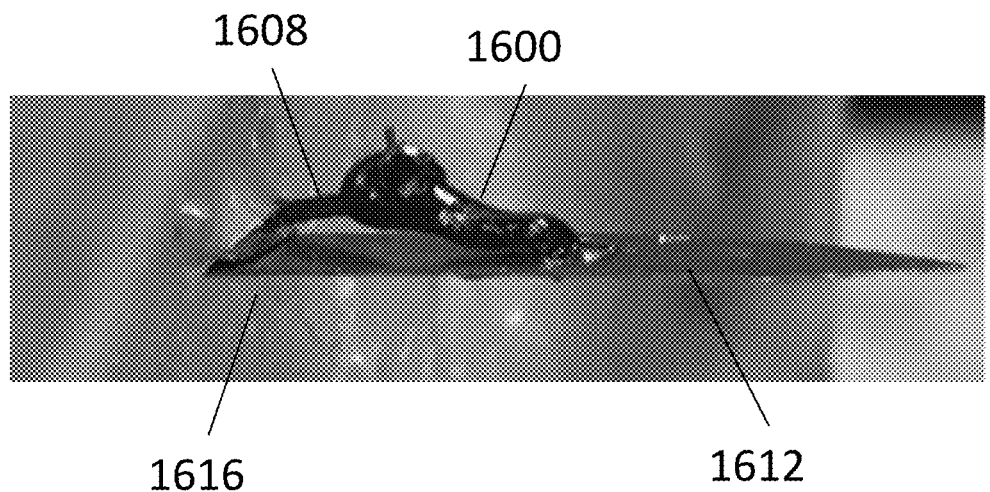
Figure 48E:
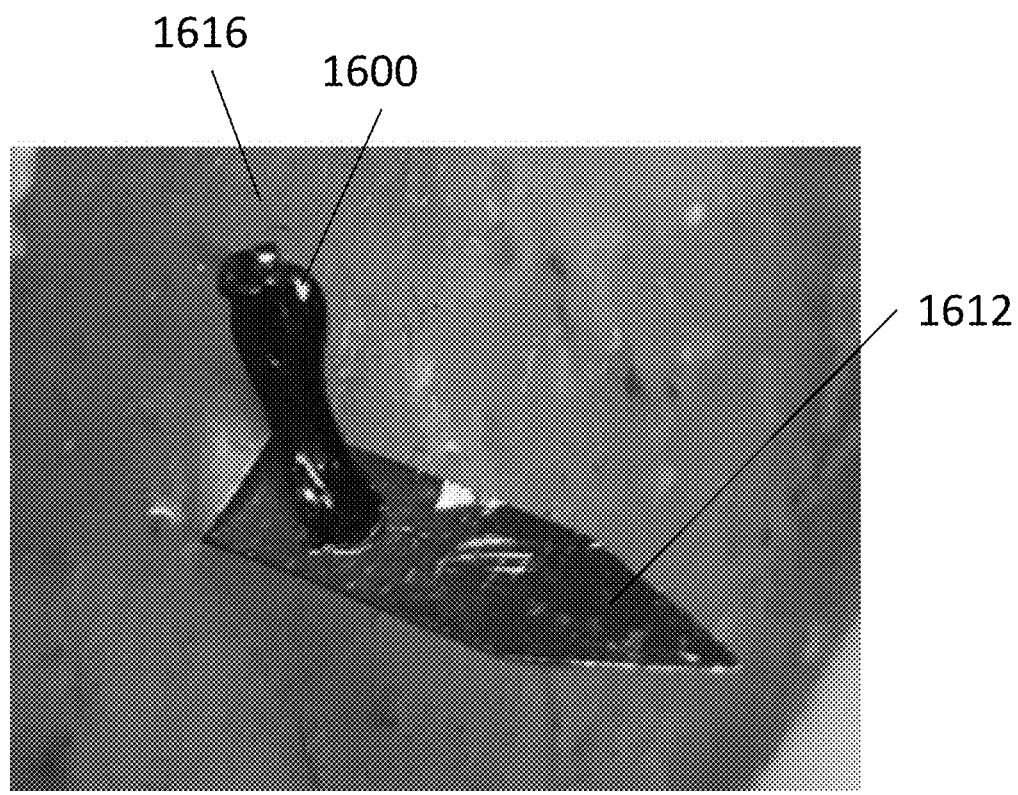

Coupling of a tension element to the dog bone is shown in FIG. 48B. Referring to the figure, tension element (1608) may be coupled to the dog bone (1600) by threading the tension element (108) through one opening (1606). An enlarged distal end (toe) (1610) may prevent the tension element from passing back through the opening (1606). Coupling of the dog bone to an anchor delivery element is depicted in FIG. 48C. Referring to FIG. 48C, the lobed end not coupled to the tension element may be coupled to an anchor delivery element (1612) by threading the enlarged lobed end (1602) through an opening (1614) in the anchor delivery element (1612) until the thinner midsection (1604) is reached. Opening (1614) is sized and/or shaped to prevent the enlarged lobed end (1602) from passing back through the opening (1606). Delivery and deployment of the dog bone through tissue is shown in FIGS. 48D and 48E. Referring to the figures, anchor delivery element (1612) with a dog bone anchor (1600) in its insertion configuration and tension element (1608) coupled thereto are inserted through tissue (1616). The dog bone anchor (1600) may then swivel to transition to a deployed configuration by withdrawing the anchor delivery element (1612) and applying a force to the tension element (1608). Further force applied to the tension element (1608) may then decouple the lobed end (1602) from the opening (1614) in the anchor delivery element (1612).

Figure 49A:
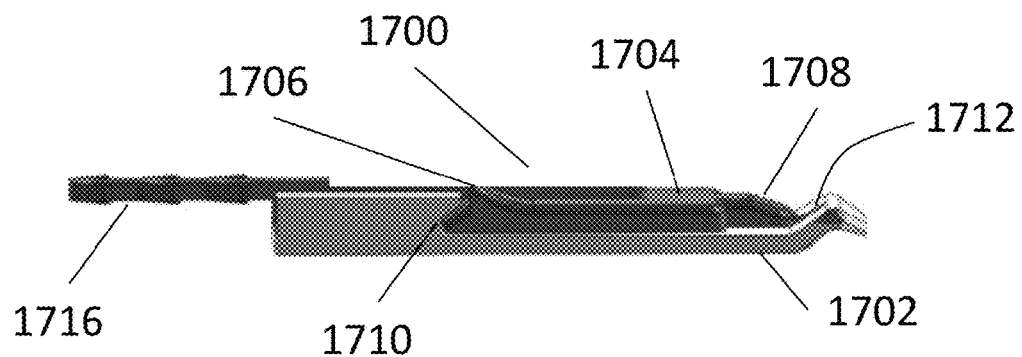
FIGS. 49A-49D depict yet another exemplary distal anchor including a heel and toe retainer, and its deployment through tissue.
Figures 49B, 49C, 49D:
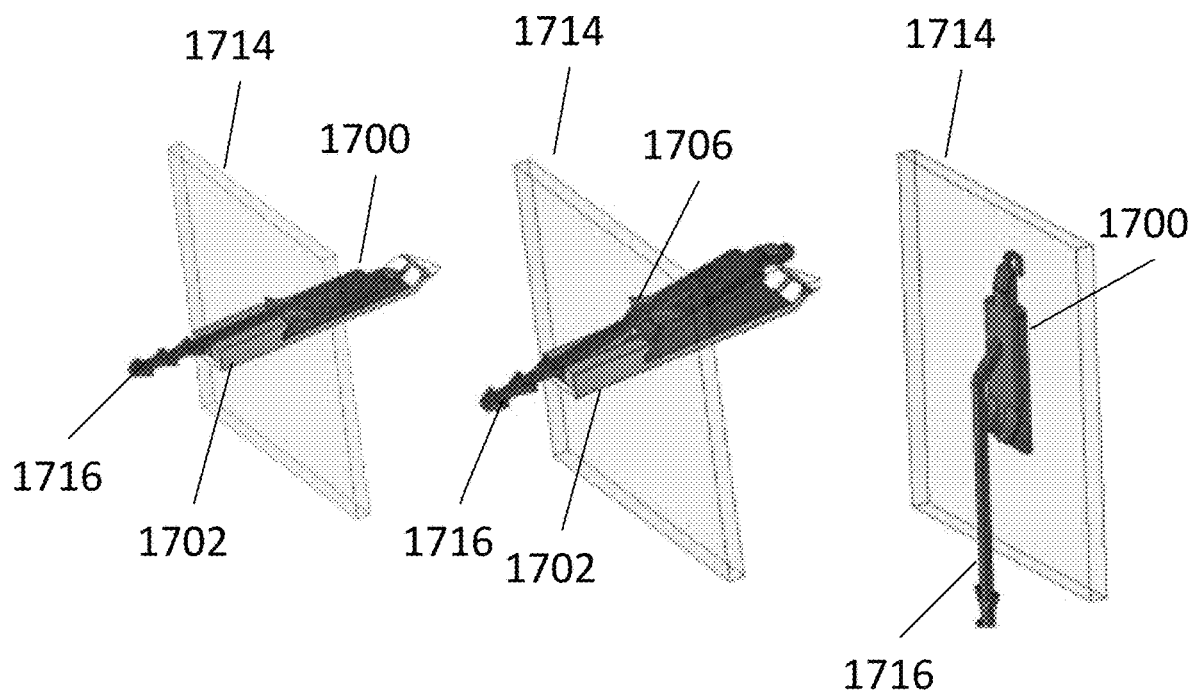
Figure 55:
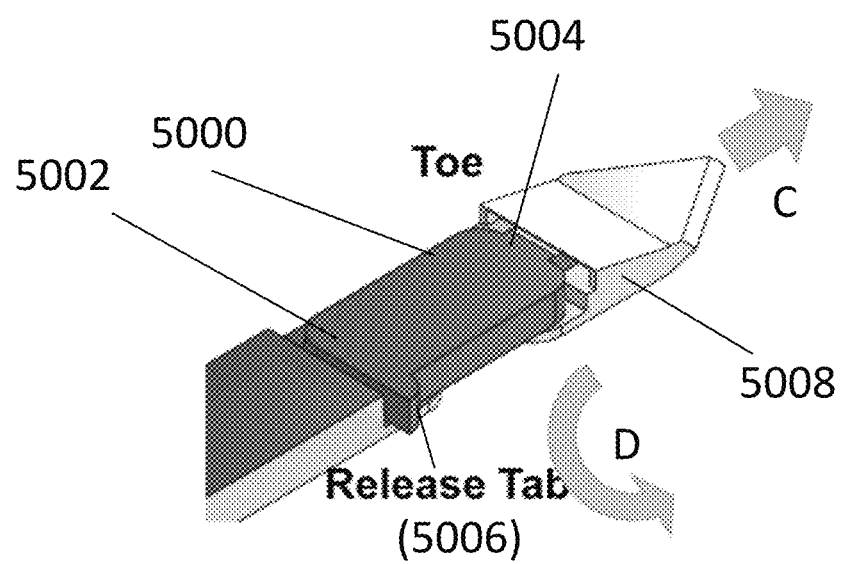
FIG. 55 depicts another distal anchor according to a further variation, and its mechanism of release from an anchor delivery element.

Similarly, in FIGS. 49A-49D another distal anchor is shown including a raised heel that facilitates swiveling of the anchor to its deployed configuration. Referring to FIG. 49A, a distal anchor (1700) is shown coupled to an anchor delivery element (1702). The distal anchor (1700) may include a body (1704) having a raised heel (1706) and a toe (1708), which fit into corresponding structures in the anchor delivery element (1702), heel indent (1710) and toe retainer (1712), respectively. In FIGS. 49B to 49D, passage of the distal anchor (1700) by anchor delivery element (1702) through tissue (1714) is illustrated. More specifically, FIG. 49B shows the distal anchor (1700) in its insertion configuration being passed through tissue (1714). After passage through the tissue (1714), the tension element (1716) may be pulled to apply a force on the raised heel (1706), which in turn swivels the body of the distal anchor (1700) to its deployed configuration. In a further variation, as shown in FIG. 55, disengagement of the distal anchor from the seating region may be accomplished using a release tab. Referring to the figure, distal anchor (5000) may include a heel (5002) and a toe (5004). A release tab (5006) may be provided on one side of the heel (5002). After passage of the distal anchor (5000) through tissue in the direction of arrow C, a force applied to the release tab (5006) may disengage the heel (5002) and toe (5004) from the anchor delivery element (5008) in the direction of arrow D, similar to how a boot is released from a ski binding.

Figure 77A:
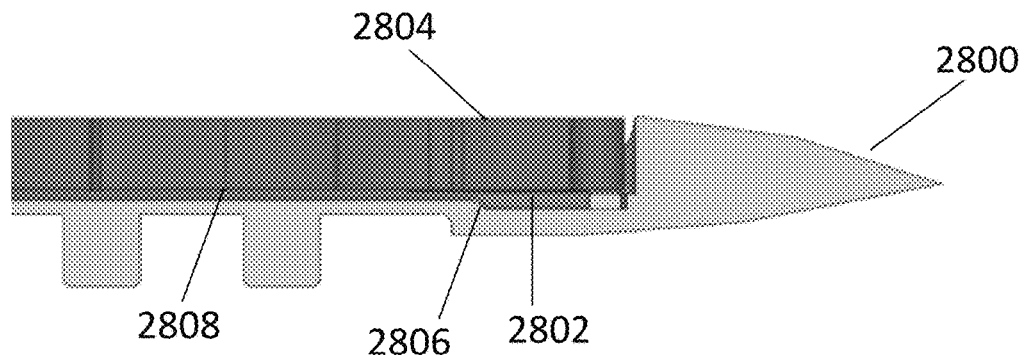
FIGS. 77A-77C depict an exemplary mechanism including a sliding wedge and a corresponding tip wedge for disengaging a distal anchor from the tip component.
Figure 77B:
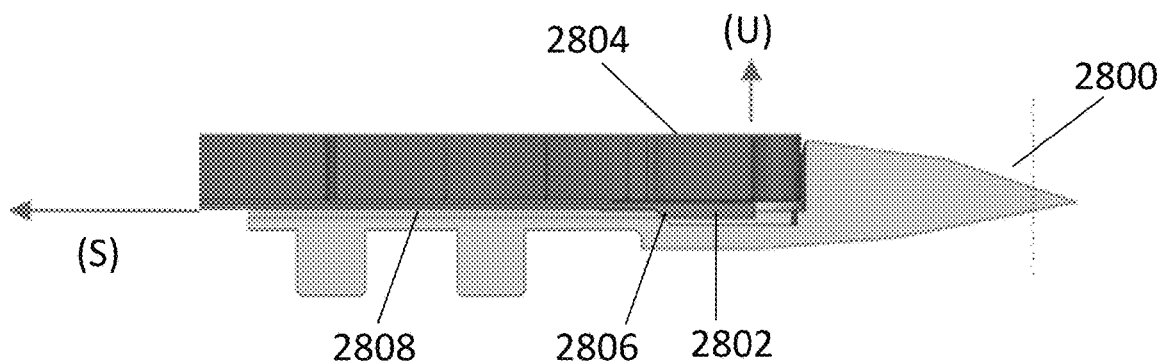
Figure 77C:
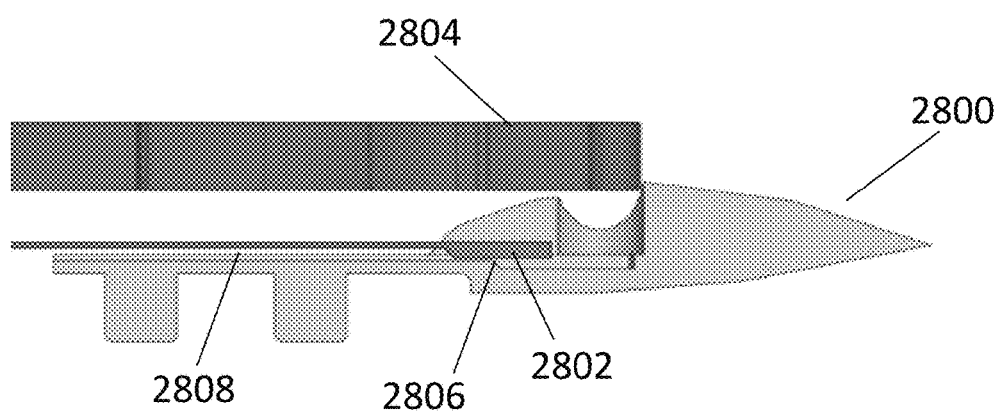
Figure 78A:
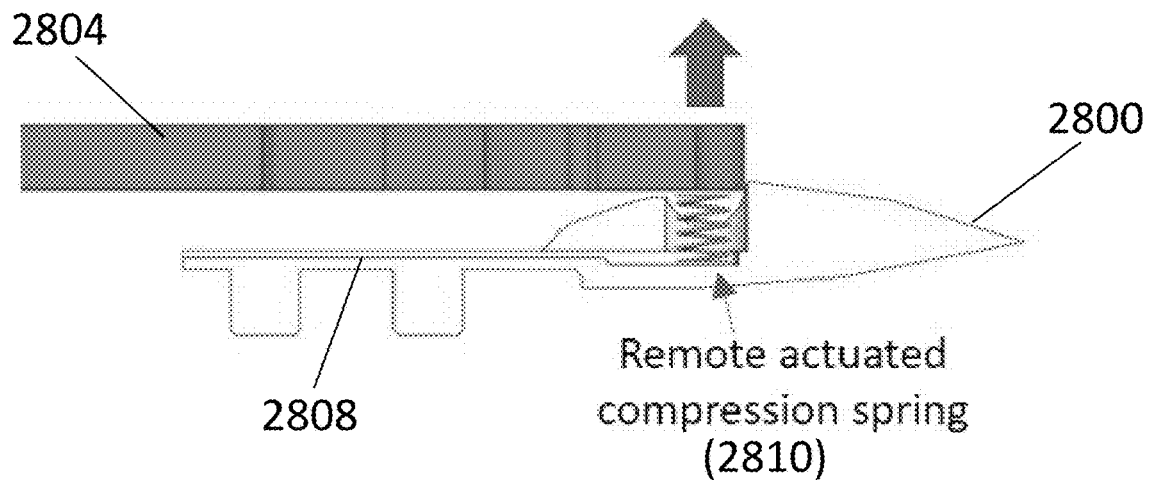
FIGS. 78A-78C depict side views of other exemplary mechanisms for disengaging a distal anchor from the tip component.
Figure 78B:
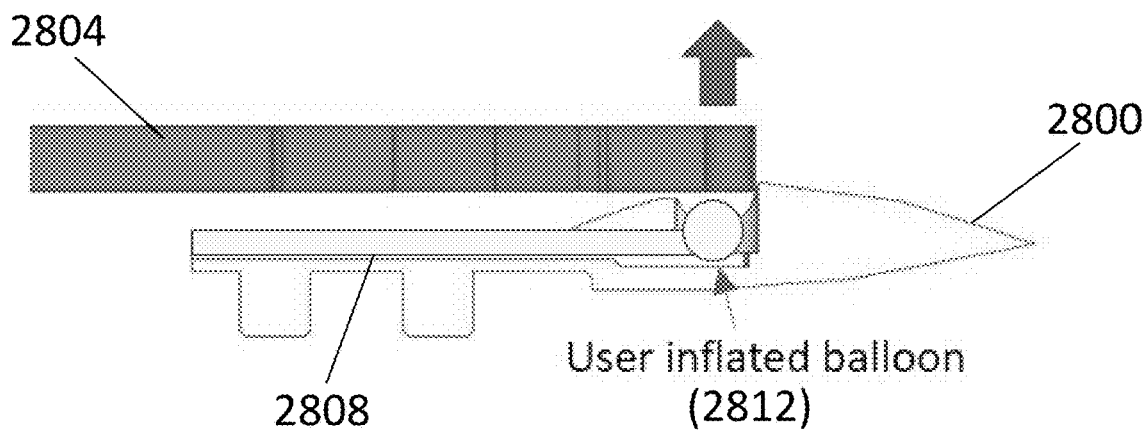
Figure 78C:
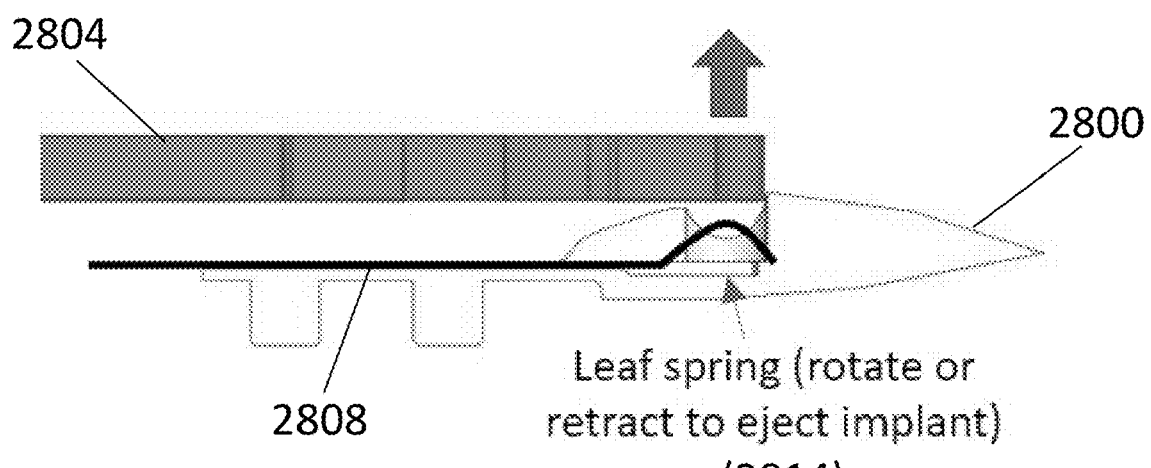

Other mechanisms or actuators for disengaging the distal anchor may include a sliding wedge, a spring or coil (e.g., a remote actuated compression spring or electrolytic detachable coil, e.g., a GDC coil), an expandable member (e.g., an inflatable/collapsible balloon), or a leaf spring. For example, referring to FIGS. 77A-77C, the tip component (2800) may include a sliding wedge (2802) under the distal anchor (2804) (see FIG. 77A). Upon withdrawing the sliding wedge (2802) in the direction of arrow(S), the sliding wedge (2802) may engage an opposing tip wedge (2806), which may raise the distal anchor (2804) out of the seating area (2808) of the tip component (2800) in the direction of arrow (U) (see FIG. 77B) to disengage the distal anchor (2804) from the tip component (2800) (see FIG. 77C). In other variations, the distal anchor (2804) may be raised out of the seating area (2808) of the tip component (2800) using a remote actuated compression spring (2810) (see FIG. 78A) or a balloon that may be collapsed/deflated upon advancement of the distal anchor (2804) to a target tissue, and then expanded/inflated when disengagement from the tip component (2800) is desired. Further variations may include a leaf spring (2814), as shown in FIG. 78C, which may be rotated or retracted to eject the distal anchor (2804) from the tip component (2800).

Figure 79A:
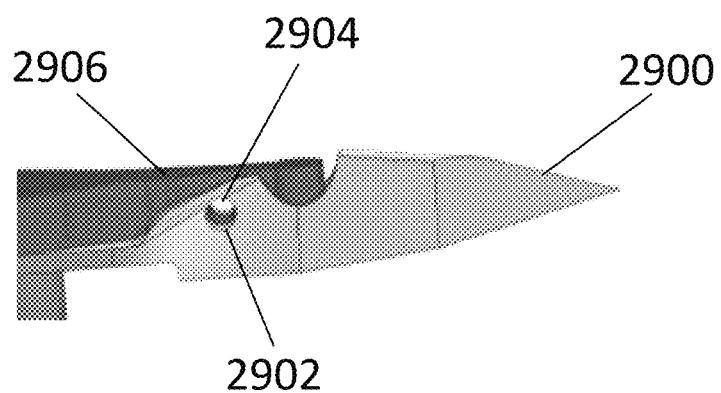
FIGS. 79A-79C depict another exemplary mechanism for disengaging a distal anchor from a tip component including a retractable tether.
Figure 79B:
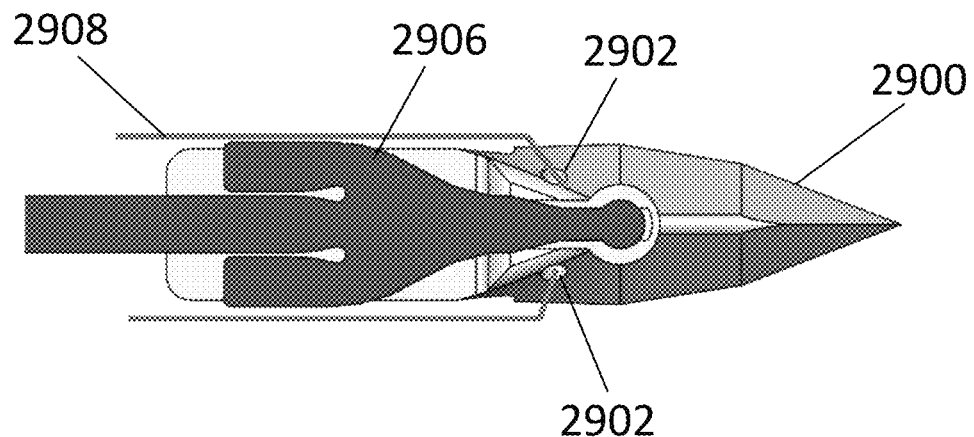
Figure 79C:
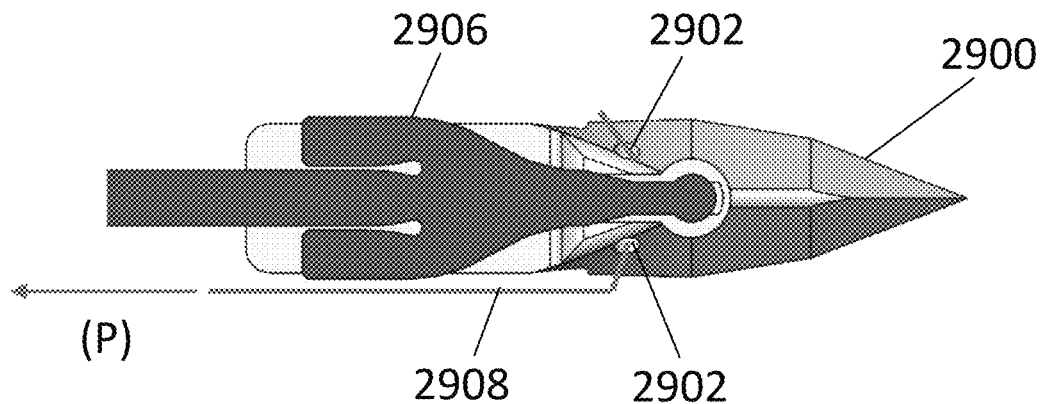

In further variations, the mechanism for disengaging the distal anchor may also include a tether (e.g., a wire or string), as shown in FIGS. 79A-79C. Referring to FIG. 79A, tip component (2900) may include openings (2902) that align with a passage (2904) in the distal anchor (2906) when the distal anchor (2906) is disposed within the tip component (2900). Before deployment, as illustrated in FIG. 79B, a tether (2908) may be threaded through the tip component openings (292) and distal anchor passage (2904) to retain the distal anchor (2906) on the tip component (2900). When disengagement from the tip component (2900) is desired, the tether (2908) may be pulled in the direction of arrow (P) to remove the tether (2902) and thus release the distal anchor (2906) from the tip component (2900).

Figure 86A:
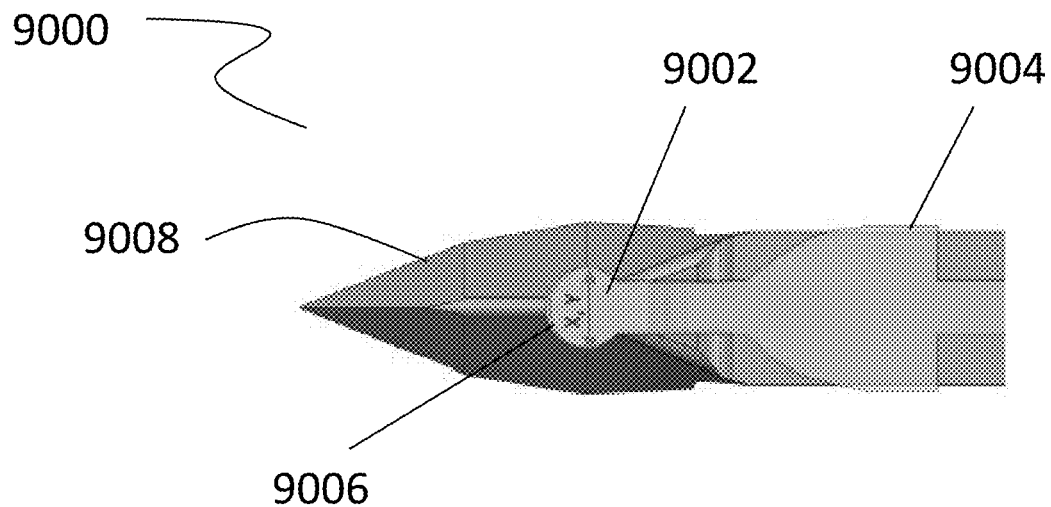
FIGS. 86A-86E illustrate exemplary mechanisms for facilitating release of the enlarged tip of a distal anchor from the cutting tip of an anchor delivery element.
Figure 86B:
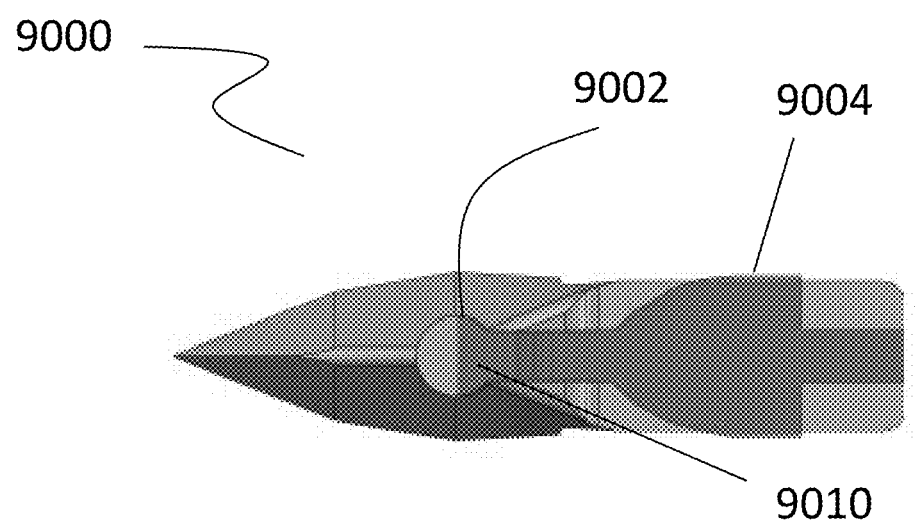
Figure 86C:
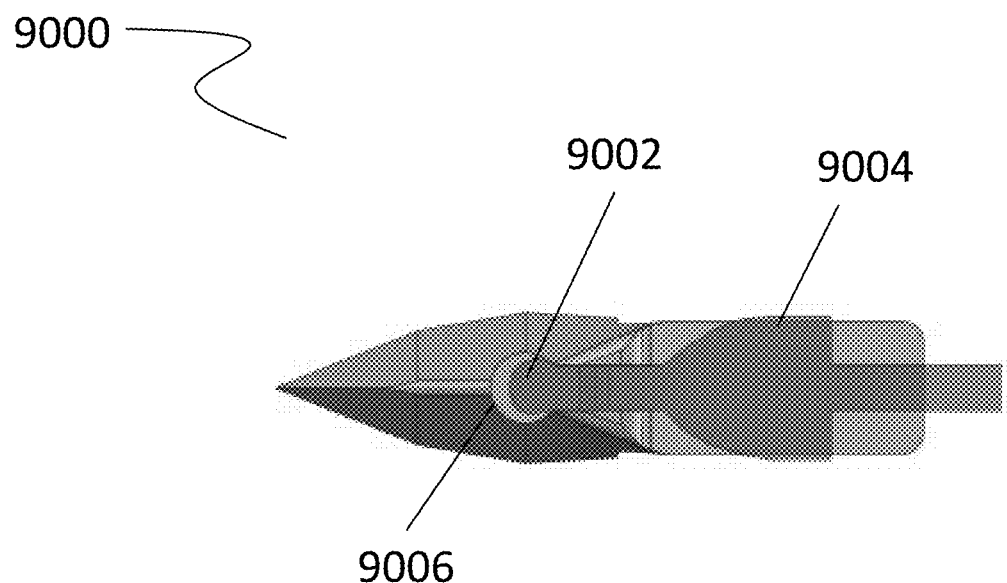
Figure 86D:
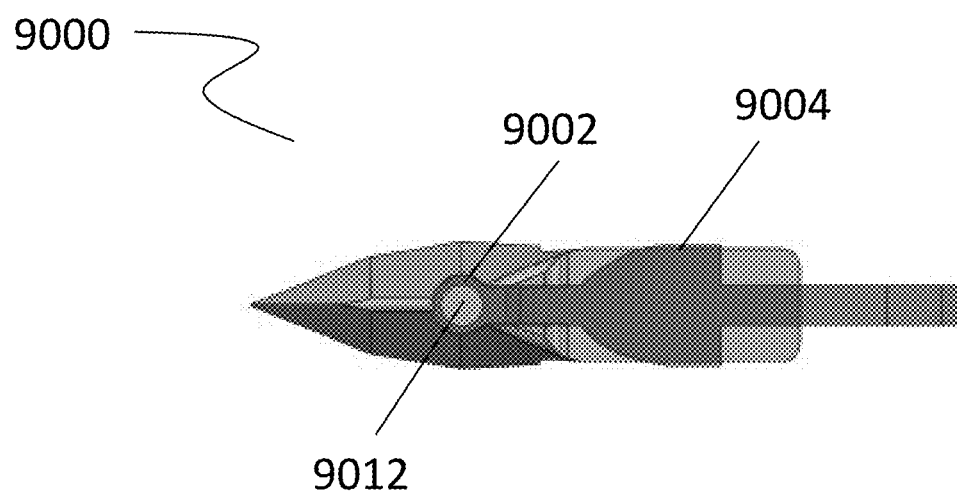
Figure 86E:
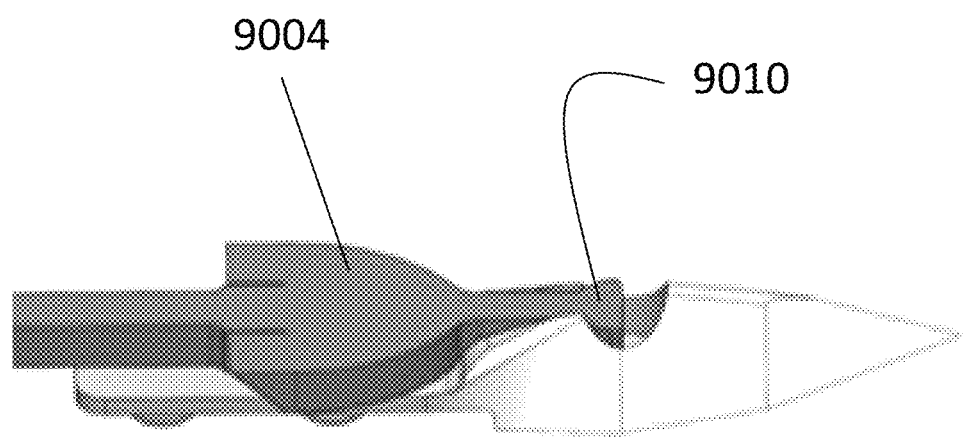

In yet further variations, the pocket of the cutting tip and/or the enlarged tip (toe) of the tension element may be configured to facilitate release of the distal anchor from the anchor delivery element. In these variations, the shape and/or size of the pocket and enlarged tip may help facilitate the release. For example, as shown in FIG. 86A, the enlarged tip (9002) of distal anchor (9004) may have a width (Y) that matches the width (X) of the pocket (9006) in the cutting tip (9008) of the anchor delivery element (9000) such that an interference fit is created. When the distal anchor (9004) is to be disengaged from the anchor delivery element (9000), a force may be applied toward the proximal end of the tension element to peel the enlarged tip (9002) out of the pocket (9006). Distal anchor (9004) release may also be facilitated when the distal end of the enlarged tip (9002) is shaped as a semi-circle (9010) that partially fills the pocket (9006), as shown in FIGS. 86B and 86E. The enlarged tip may also have a size and shape that does not correspond to the shape of the pocket. For example, as shown in FIG. 86C, the enlarged tip (9002) may be smaller in size than the pocket (9006) and have a different shape (e.g., non-circular shape) than the pocket shape (e.g., circular shape). In another variation, as shown in FIG. 86D, release from the anchor delivery element (9000) may be facilitated using a distal anchor including a central cutout (9012) in the enlarged tip (9002).

Figure 50A:
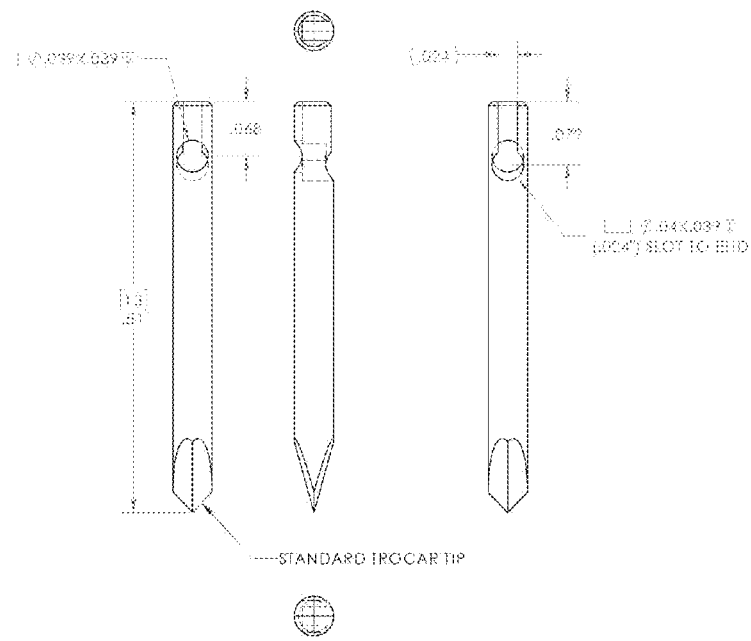
FIGS. 50A and 50B depict exemplary quick-release needles for use at the proximal end of the tension element.
Figure 50B:
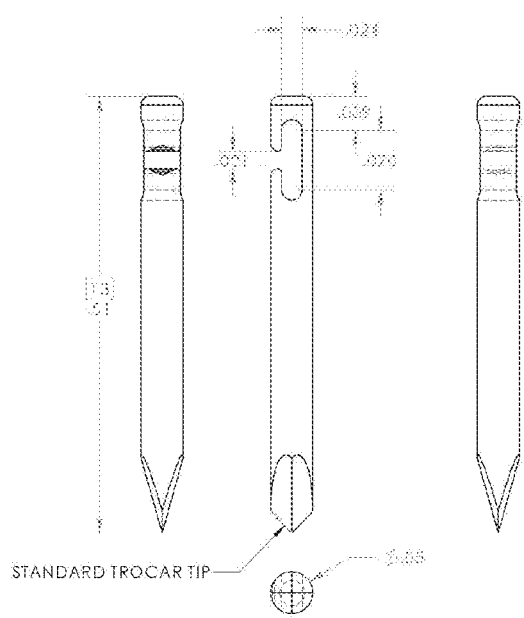

A proximal needle may be used to place or manipulate the proximal end of the elongate body through or around tissue, and may be removably attached in various ways to the tension element. For example, as shown in FIGS. 50A and 50B, the proximal needle may be a quick-thread needle designed to allow an operator to manually connect the proximal end just prior to insertion into the patient.

Figure 51A:
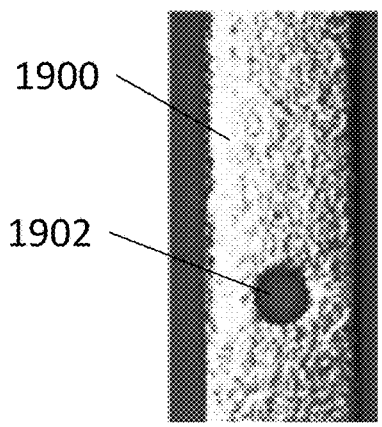
FIGS. 51A-51C depict exemplary keyhole shapes for removably coupling the toe of a tension element to an anchor delivery element.
Figure 51B:
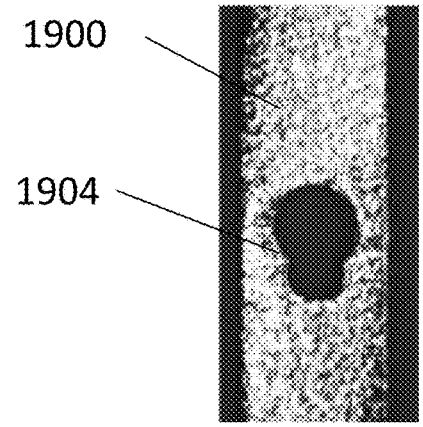
Figure 51C:
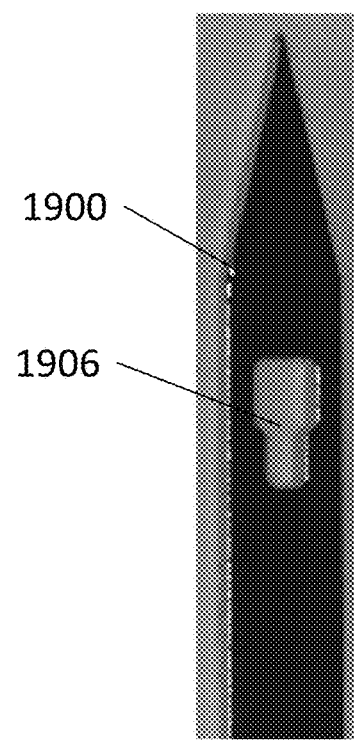

At the distal end of the tension element, an anchor delivery element may be coupled to the distal anchor. The anchor delivery elements may have various configurations, and may be reversibly secured to the tension element in various ways. In general, the anchor delivery element may include a cutting tip configured to pass the distal anchor through the tissue in its insertion configuration. In some variations, as shown in FIGS. 51A-51C, the anchor delivery element (1900) may include keyholes (1902, 1904, 1906) variously sized and shaped to removably couple a distal anchor (not shown) to the anchor delivery element (1900). For example, the keyholes (1902, 1904, 1906) may be dimensioned to keep the toe portion of the distal anchor coupled to the anchor delivery element during tissue insertion but allow disengagement of distal anchor during withdrawal of the anchor delivery element back through the tissue.

Figure 52A:
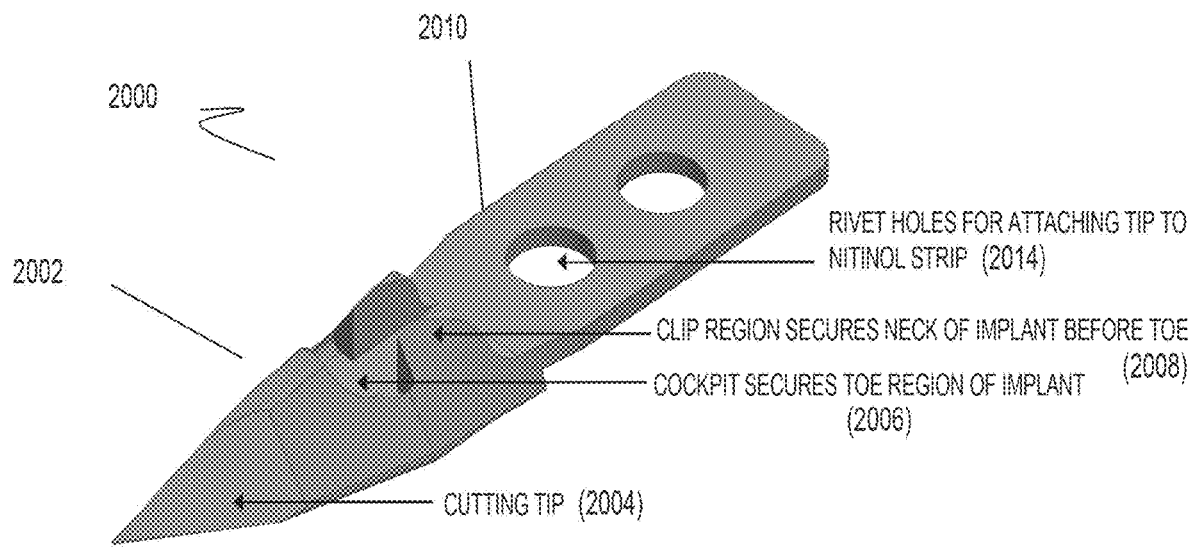
FIGS. 52A-52C depict an exemplary anchor delivery element.
Figure 52B:
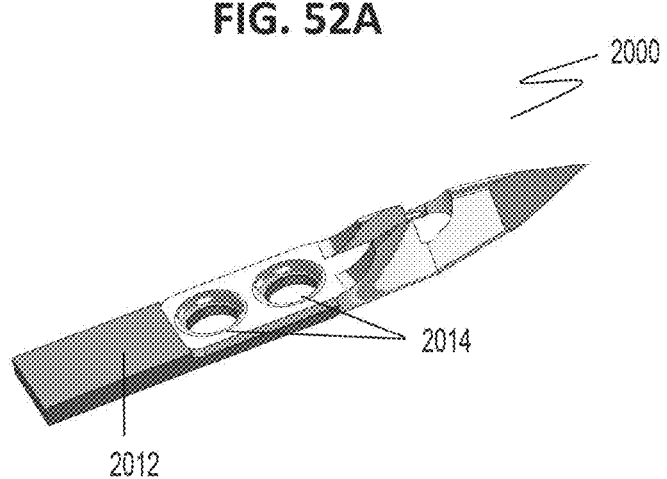
Figure 52C:
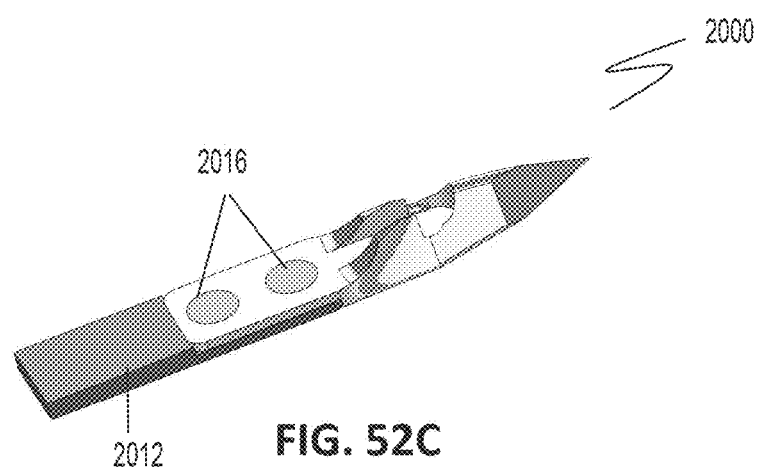
Figure 53:
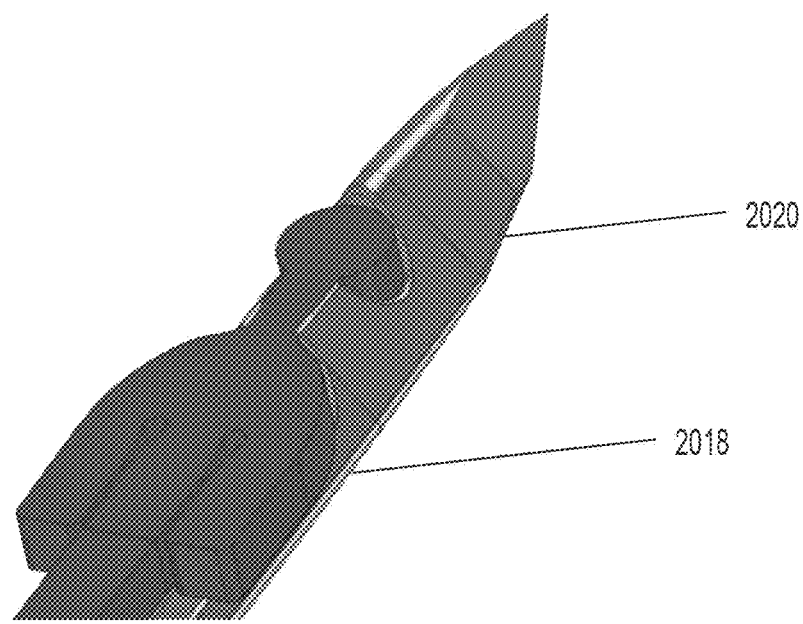
FIG. 53 depicts an exemplary Z-Flex anchor seated within the anchor delivery element of FIGS. 52A-52C.

In other variations, the anchor delivery element may include a tip component and an anchor support. Referring to FIGS. 52A-52C, the tip component (2002) of an anchor delivery element (2000) may include a cutting tip (2004), a cockpit or pocket (2006) shaped to removably secure the enlarged distal end of the tension element (toc) (e.g., see element 2020 in FIG. 53), a clip region (2008) that removably secures the region of the tension element between the toe and distal anchor to the anchor delivery element, and a seating region (2010) on the anchor support upon which the distal anchor may be positioned prior to deployment. FIG. 53 shows an exemplary Z-Flex anchor (2018) seated within the anchor delivery element described in FIGS. 52A-52C.

In one variation, the tip component and the anchor support may be integrally formed as a single piece. In another variation, the tip component (2000) and the anchor support (2012) may be separate components that are joined together, as shown in FIGS. 52A and 52B. In this variation, the tip component (2000) includes rivet holes (2014) that may align with corresponding rivet holes in the anchor support (2012). Rivets (2016) may be placed in the rivet holes to secure the tip component (2000) and anchor support (2012) together to form the anchor delivery element. The tip component and anchor support may also be joined by crimping or welding.

Figure 54:
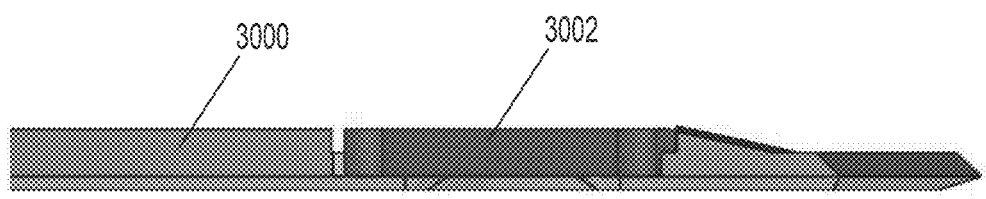
FIG. 54 depicts an exemplary distal anchor surface being level with the anchor delivery element surface.
Figure 72A:
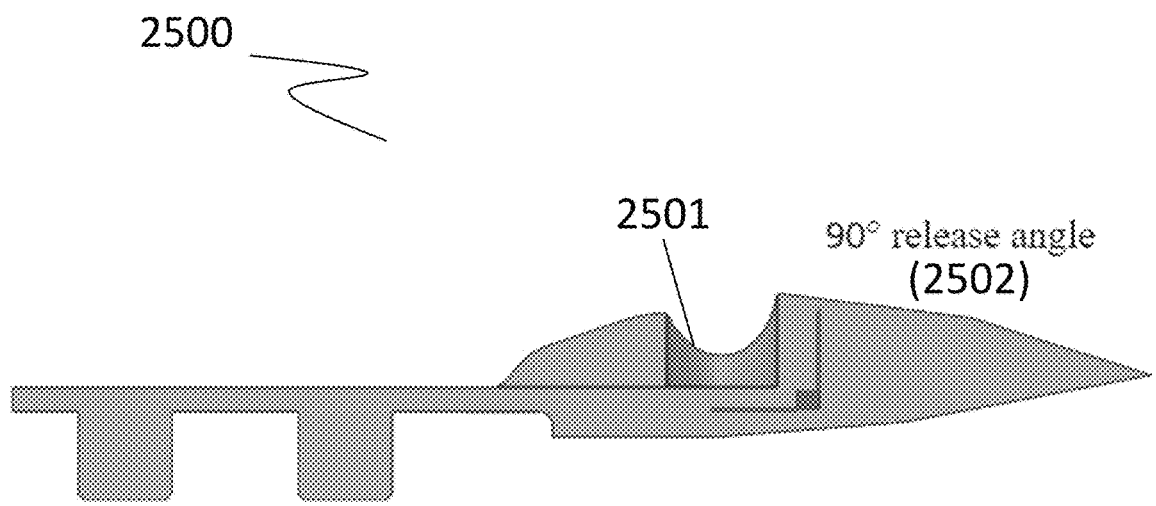
FIGS. 72A and 72B depict exemplary tip components with internal bevels.
Figure 72B:
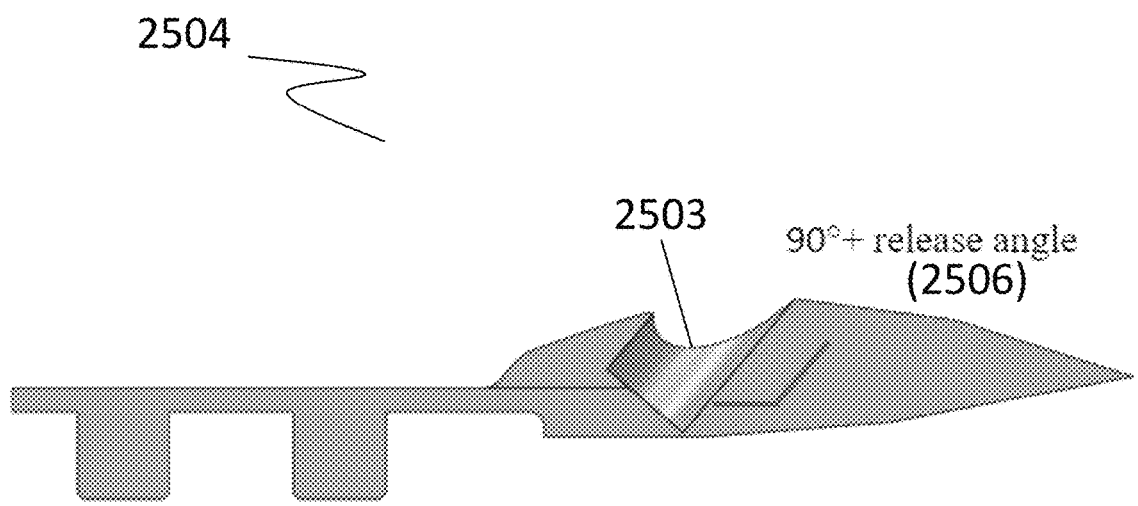

The tip component may be configured in various ways. In one variation, the tip component may be formed such that it or the distal anchor does not have any leading edges that may catch on tissue during delivery to a target tissue. For example, as shown in FIG. 54, the anchor delivery element (3000) and distal anchor (3002) of the tension element (not shown) may form a level surface that may prevent the distal anchor from catching on tissue during insertion. In other variations, as shown in FIGS. 72A and 72B, the tip component may include a bevel that helps to facilitate distal anchor release. For example, as shown in FIG. 72A, the tip component (2500) may include an internal bevel (2501) configured to create a 90 degree release angle (2502). Alternatively, as shown in FIG. 72B, the tip component (2504) may include an internal bevel (2503) configured to create a release angle (2506) of greater than 90 degrees (e.g., 120 degrees).

Figure 73:
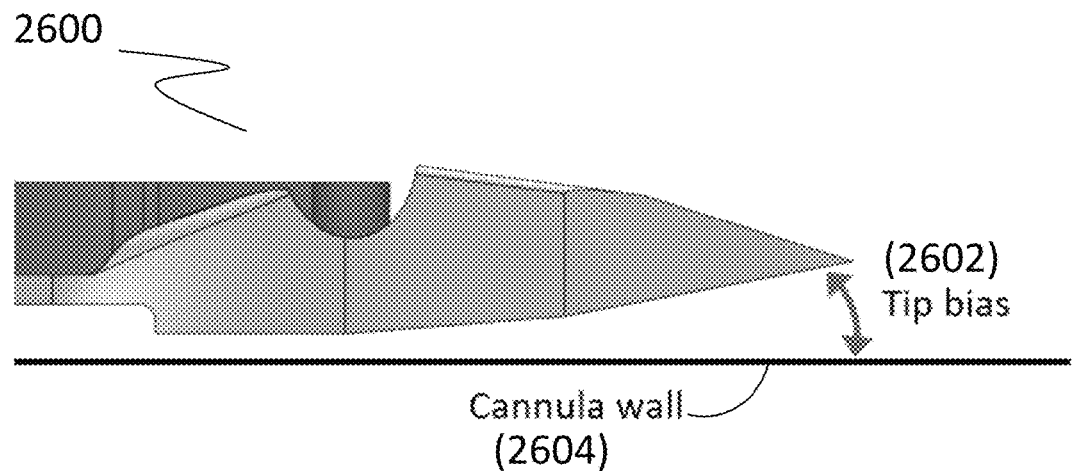
FIG. 73 depicts another exemplary tip component having a tip bias.
Figure 74A:
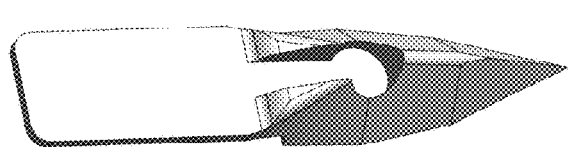
FIG. 74A depicts another exemplary tip component having a cutting profile. Use of the cutting tip component may result in the tissue defect shown in FIG. 74B.
Figure 74B:
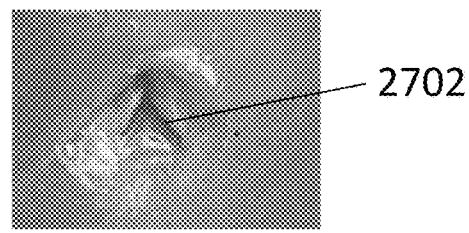
Figure 75A:
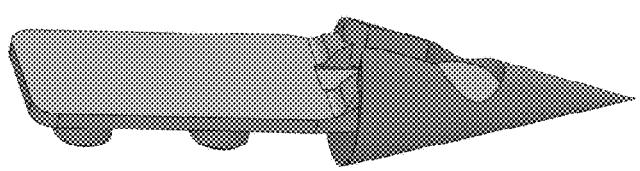
FIG. 75A depicts another exemplary tip component having a tapered profile. Use of the tapered tip component may result in the tissue defect shown in FIG. 75B.
Figure 75B:
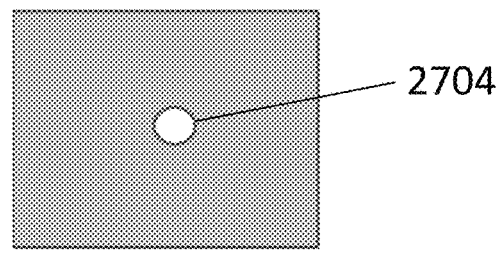
Figure 76:
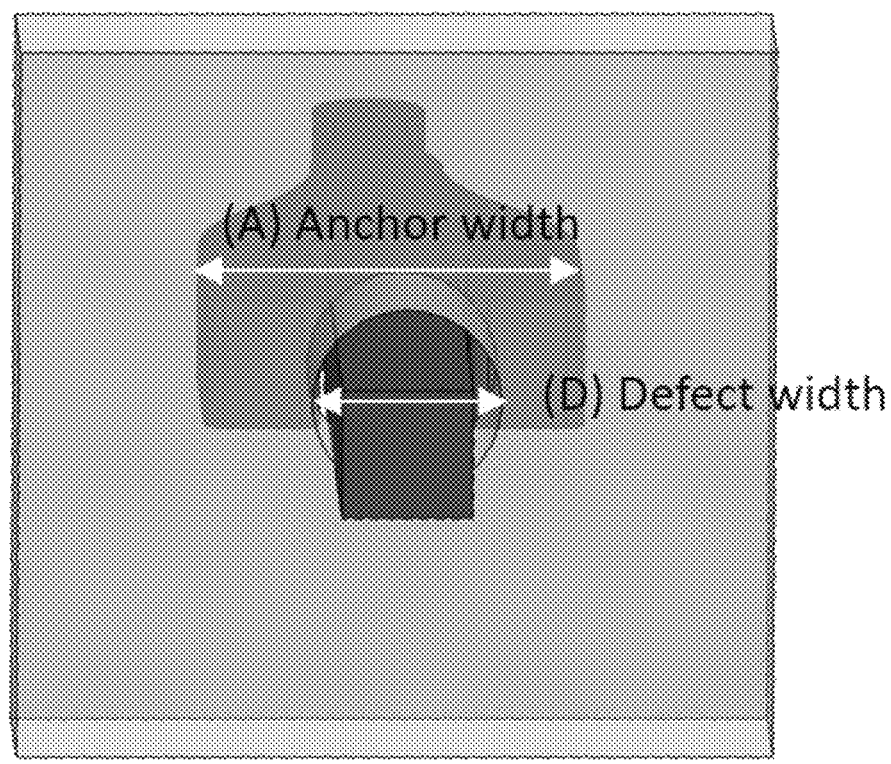
FIG. 76 provides a comparison between a distal anchor width (A) and a tissue defect width (D).

Referring to FIG. 73, the tip component (2600) may also be configured to include a tip bias (2602) from the cannula wall (2604) to help facilitate travel through tissue such as cartilage. As shown in FIG. 73, the tip bias (2602) may be about 20 degrees. However, in other variations, the tip bias may range from about 5 degrees to about 35 degrees from the cannula wall (2604) when loaded within a cannula. In one variation, the tip bias may be configured to match the bend angle or the curvature of the cannula. Other tip component variations may include a cutting profile, as shown in FIG. 74A, which may result in a tri-leaflet defect (2702) in cartilage, as illustrated in FIG. 74B. A tri-leaflet defect is non-coring (e.g., does not remove a large amount of tissue), and thus may reduce the risk of septal perforation when working with nasal septal cartilage and may improve healing of the tissue. Alternatively, the tip component may have a tapered profile, as shown in FIG. 75A, which may result in a circular defect (2704) in cartilage, as depicted in FIG. 75B. The configuration of defects may vary, but in general, and as illustrated in FIG. 76, it may be beneficial for the width of the distal anchor (A) to be larger than the defect width (D) to help fix the distal anchor within the target tissue. The tip component may be made from various materials, for example, polymers or metals. The polymer may be any biodegradable or a non-biodegradable polymer described herein. Exemplary metals include, but are not limited to, silver, platinum, stainless steel, nickel, titanium, and alloys thereof. The tip components may be made in various ways, for example, by injection molding, three-dimensional (3D) printing, or machining (e.g., electrical discharge machining (EDM) or computer numerical control (CNC) machining).

The tissues that may be manipulated with the devices describe herein include without limitation, nasal tissues, throat tissues, and car tissues. Non-limiting examples of nasal tissue include nasal septal cartilage, lateral nasal cartilage, major alar cartilage, minor alar cartilage, alar fibrofatty tissue, nasal bone, or a nasal turbinate. Exemplary throat tissues include without limitation, oropharyngeal soft tissue, the uvula, soft palate, and tonsils. Non-limiting examples of car tissues include cartilage of the helix, anti-helix, tragus, anti-tragus, superior crus, fossa triangularis, concha, and connective tissue of the earlobe.

Accessory Devices

Figure 89:
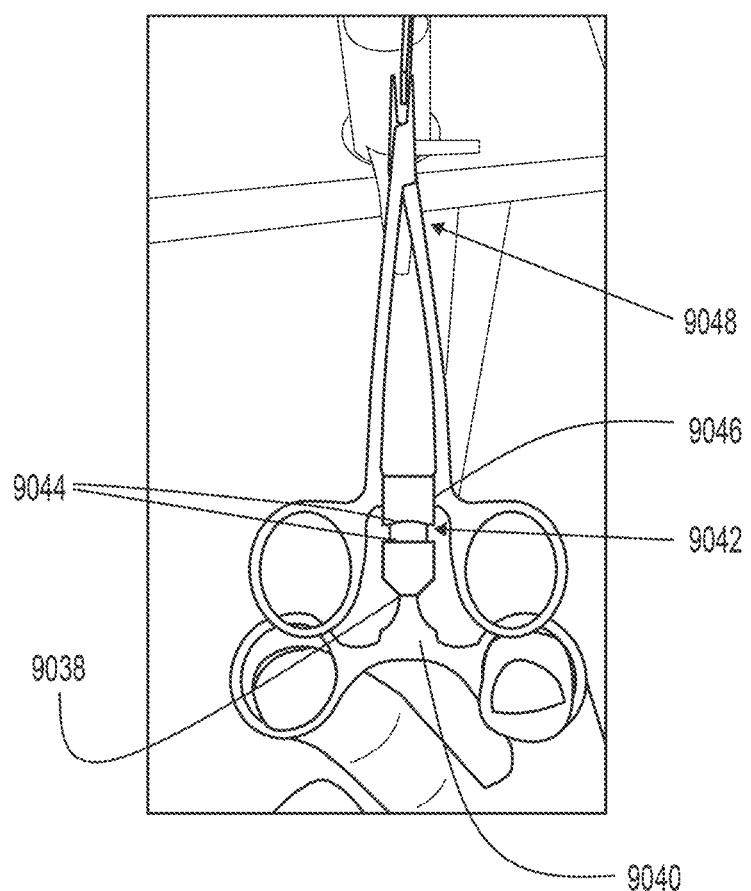
FIG. 89 shows an exemplary accessory tool for limiting the amount of tension force applied to the tension element.

Accessory devices that help to limit the amount of tension force applied to the tension element are also described herein. Limiting the applied tension may help prevent the tension element from being inadvertently pulled out of tissue, and may also reduce physician to physician variability in using the device and/or system. In some variations, the accessory device may be a tool comprising one or more magnets that may be decoupled upon application of a tension force above a threshold value, e.g., above about 5.0 N to about 20 N, including all values and sub-ranges therein. For example, the threshold value may be about 5.0 N, about 5.5 N, about 6.0 N, about 6.5 N, about 7.0 N, about 7.5 N, about 8.0 N, about 8.5 N, about 9.0 N, about 9.5 N, about 10 N, about 10.5 N, about 11 N, about 11.5 N, about 12 N, about 12.5 N, about 13 N, about 13.5 N, about 14 N, about 14.5 N, about 15 N, about 15.5 N, about 16 N, about 16.5 N, about 17 N, about 17.5 N, about 18 N, about 18.5 N, about 19 N, or about 20 N. Referring to FIG. 89, the tool (9038) may include a handle (9040) and a link (9042) comprising two magnets (9044). The link (9042) may be attached to the handle (9046) of another device, e.g., a clamp or needle driver (9048), that may be holding the tension element (not shown) for tensioning. When the tool (9038) is pulled proximally to apply tension to the tension element, the magnets (9044) may be configured to decouple when the applied tension is above the threshold value. Although two magnets are shown in FIG. 89, any suitable number of magnets may be employed.

Figure 90A:
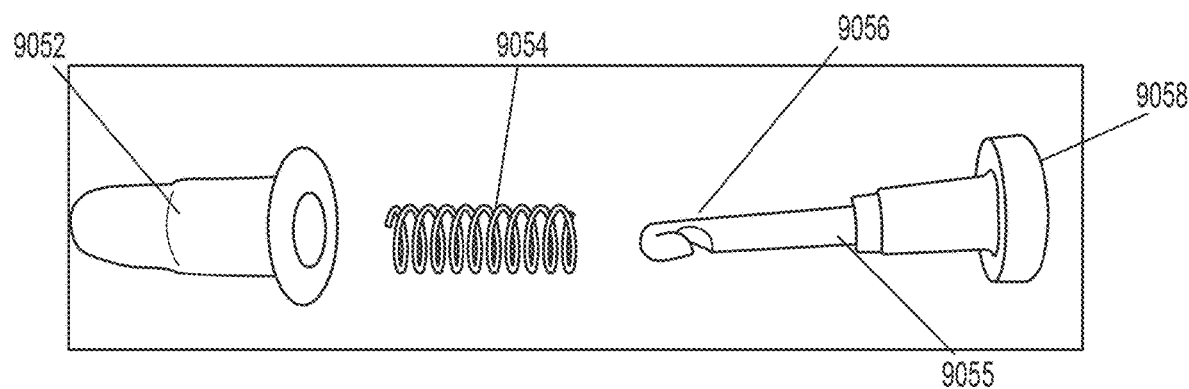
FIGS. 90A-90C show another exemplary accessory tool for limiting the amount of tension force applied to the tension element.
Figure 90B:
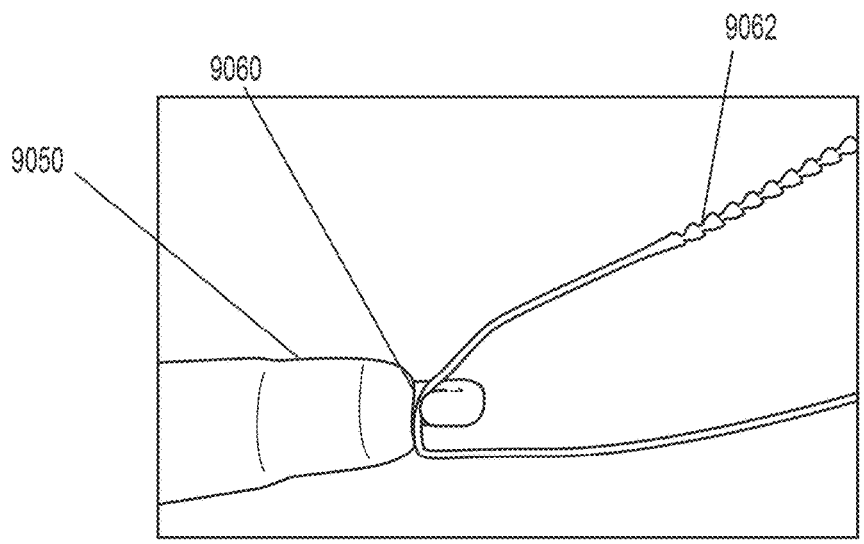
Figure 90C:
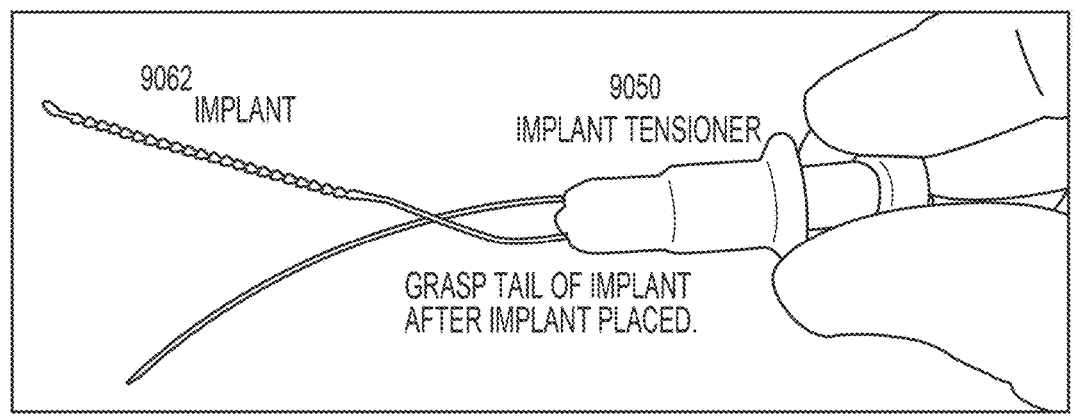

In another variation, the tool may include a spring configured to release the tension element when the applied tension is above the threshold value mentioned above. The spring constant of the spring may range from about 250 N/m to about 1000 N/m, including all values and sub-ranges therein. For example, the spring constant may be about 250 N/m about 300 N/m, about 350 N/m, about 400 N/m, about 450 N/m, about 500 N/m, about 550 N/m, about 600 N/m, about 650 N/m, about 700 N/m, about 750 N/m, about 800 N/m, about 850 N/m, about 900 N/m, about 950 N/m, or about 1000 N/m. Referring to FIGS. 90A-90C, the tool (implant tensioner, 9050) may include a housing (9052), a spring (9054), and a shaft (9055) comprising a hook (9056) at one end, and a grip (9058) at the other end. The spring (9054) may sit within the housing (9052) and be concentrically mounted on the shaft (9055), such that the hook (9056) may pass through a distal housing opening (9060) upon compression of the spring (9054) to allow threading of a tension element (9062) through the hook (FIG. 90B). After the proximal end (e.g., the tail) of the tension element (9062) is threaded through the hook (9056), the tension element (9062) is coupled to the tool (9050). The user may then grasp the grip (9058) and apply tension to the tension element (9062). If too much tension is applied, the spring (9054) will release the tension element (9062) from the tool (9050), release the implant from the hook (9056), and remove the tension force being applied on the tissue.

In some variations, the devices generally include one or more tension elements or shaping elements configured to apply and maintain a force against tissue to alter the shape of the tissue. The force may be a tension force. The tension element may include an elongate body having a proximal end, a distal end, a relaxed state, and a tensioned state. At the distal end, a securing element may be coupled to, or disposed on, the tension element to fix or anchor the tension element to a tissue. One or more migration prevention elements may be provided on the proximal end of the tension element to hold the tension element in its tensioned state after deployment. A needle may also be provided on the proximal end to direct or facilitate placement of the tension element through tissue.

In some variations, the devices for shaping a tissue structure of a subject may include an elongate member (e.g., an elongate member of a delivery device) comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

The tension element may be made from various materials. Exemplary materials include without limitation, LPLA (Poly (L-lactide)), DLPLA (Poly(DL-lactide)), LDLPLA (Poly (DL-lactide-co-L-lactide)), LPLA-HA (Poly(L-lactide) with hydroxylapatite), PGA (Poly(glycolide)), PGA-TMC (Poly (glycolide-co-trimethylene carbonate) or polyglyconate), PDO (Poly(dioxanone)), LPLG (Poly(L-lactide-co-glycolide)), DLPLG (Poly(DL-lactide-co-glycolide), a copolymer of any of these or other suitable polymers, or any other suitable material. In one variation, the tension element is made from PDO (Poly(dioxanone)).

The length of the tension element may range from about 3.0 cm to about 30 cm, including all values and sub-ranges therein. For example, the length of the tension element may be about 3.0 cm, about 4.0 cm, about 5.0 cm, about 6.0 cm, about 8.0 cm, about 9.0 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, or about 25 cm. In one variation, the length of the tension element is about 15 cm.

The shaping element may include a securing element that anchors or fixes the shaping element to a tissue, for example, a nasal tissue. The securing element may be configured such that a first end of the shaping element may be directed through the tissue but prevented from passing back through the nasal tissue. In some variations, the securing element comprises one or more of a T-fastener, an X-shaped fastener, an expandable anchor, a knot, a button, a shape-retaining structure, a barb, and a plurality of barbs. In one variation, the securing element includes a plurality of barbs. In other variations, the securing element may be adjustable or slidable along the shaping element relative to the first end. In some instances, the shaping element may include a plurality of protrusions spaced from one another adjacent the first end. A securing element coupled to the shaping element may be configured to releasably engage the protrusions to adjust the position of the securing element relative to the first end.

One or more migration prevention elements may be provided between the first (distal) and second (proximal) ends of the shaping element to hold the shaping element in its tensioned state after deployment. In one variation, a plurality of migration prevention elements may be disposed closer to the second (proximal end) than to the first (distal) end. The one or more migration prevention elements may comprise a plurality of ratchet elements on a region of the shaping element spaced from the first end. A plurality of barbs may also be used as migration prevention elements. In some variations, the migration prevention elements may be a plurality of hooks, arrows, spherical-shaped elements, or other shaped elements disposed along the shaping element. Alternatively, the one or more migration prevention elements may be configured to allow the shaping element to be directed through tissue in a first direction but prevent passage in a second direction back through the tissue.

The devices may further include a force distribution region on the shaping element spaced from first end to provide atraumatic contact of the shaping element with tissue. In some variations, the force distribution region may have a width and/or surface area greater than the shaping element adjacent the force distribution region. The width of the force distribution region may range from about 0.25 mm to about 2.5 mm, including all values and sub-ranges therein. For example, the force distribution region width may be about 0.25 mm, about 0.50 mm, about 0.75 mm, about 1.0 mm, about 1.25 mm, about 1.5 mm, about 1.75 mm, about 2.0 mm, about 2.25 mm, or about 2.50 mm. In some variations, the force distribution region width may range from about 0.50 mm to about 1.0 mm. Delivery of the shaping elements to a target region of a tissue may be accomplished using suture techniques or via an elongate member, for example, an elongate member of a delivery device. The elongate member may have any length suitable to access the target tissue region and place the shaping element therein. In some variations, the length of the elongate member may range from about 3.0 cm to about 10 cm, including all values and sub-ranges therein. For example, the length of the elongate member may be about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm, or about 10 cm.

The elongate member may include one or more ports for deployment of the shaping element from the lumen of the elongate member. In one variation, the elongate member includes a single port. In another variation, the elongate member includes two ports. The one or more ports may be located on a sidewall of the distal end, and may be any suitable size and shape. For example, the ports may be circular, ovular, triangular, rectangular, square, slit-like, etc. In one variation, the device further includes a guide element sized for introduction into the lumen. The guide element may be movable relative to the elongate member for directing a tip of the guide element out the side port into tissue. The guide element may also include a guide interface, where the first end of the shaping element engages with the guide interface such that the first end is deployable from the tip. In some variations, the guide element comprises a needle terminating in a sharpened distal tip configured to penetrate through tissue. In other variations, the guide element may include a hollow needle with a lumen. The length of the guide element may range from about 3.0 cm to about 10 cm, including all values and sub-ranges therein. For example, the length of the elongate member may be about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm, or about 10 cm. In some variations, the length of the guide element ranges from about 9.0 cm to about 11 cm, including all values and sub-ranges therein.

The elongate member may further include an actuator on the proximal end of the elongate member for selectively directing the guide element from a proximal position, where the tip of the guide element is within the distal end of the elongate member, and a distal position, wherein the tip of the guide element extends out a side port. In one variation, the tip of the guide element may be biased to a curved shape to direct the tip laterally relative to the distal end of the elongate member. In another variation, the elongate member includes an imaging or visualization element on its distal end. Exemplary imaging and visualization elements include without limitation, a fiberoptic visualization device, CCD, CMOS or other camera. In a further variation, a handle may be provided at the proximal end of the elongate member, and include one or more actuators for deploying the shaping element.

In another variation, the device for shaping a tissue structure of a subject may include an elongate member comprising a proximal end, a distal end sized for introduction into the subject's body, and a lumen extending between the proximal end and a port at the distal end, and a needle removably coupled to the elongate member. A shaping element may further be included that comprises a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

Other variations of the devices for shaping a tissue structure of a subject may include an elongate member comprising a proximal end, a distal end sized for introduction into the subject's body, and a lumen extending between the proximal end and a port at the distal end, a needle removably coupled to the elongate member, and a shaping element. The shaping element may include a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

In yet a further variation, the device is for shaping a tissue structure of a subject may include an elongate member comprising a proximal end, a distal end sized for introduction into the subject's body, a lumen extending between the proximal end and the distal end, a first port at the distal end, and a second port located proximal to the first port, and a shaping element. The shaping element may comprise a first end deployable from the first port to engage tissue at a first location adjacent the tissue structure, and a second end deployable from the second port to engage tissue at a second location adjacent the tissue structure, and one or more elements to maintain tension on the engaged tissue to alter the shape of the tissue structure.

The shaping of nasal tissue may further be aided by the delivery of one or more fluids to the nasal tissue. In these variations, the tension element may be configured with a fluid delivery mechanism such as a conduit, channel, or other mechanism for suitable delivery of fluid to nasal tissue. This fluid delivery mechanism may allow for the passage of fluid to achieve a therapeutic or physiologic effect. For example, the fluid delivery mechanism may be used to deliver a cold gas or liquid for the purposes of cryotherapy.

Other Exemplary Devices

Described below are devices including a tension element for altering the shape of a nasal tissue. The tension element (200) functions to secure the nasal tissue in an altered state by applying a force, pressure, or tension to the nasal tissue. In some variations, the tension element may have variable physical properties, e.g., having a flexible or rigid shape, being formed from inelastic or elastic materials, and/or including multiple segments of differing rigidity and/or other mechanical properties. In variations where some or all of the tension element is rigid, the tension element may optionally be configured such that the shape is set and maintained just before or after fixation within the nasal tissue. In some variations, the shape may be modifiable as desired by the patient or physician or as needed to obtain the required alteration in tissue shape. In some variations, the entire tension element of portions thereof may be made from a shape memory material, e.g., a shape memory polymer or metal (including metal alloys), such that the tension element may have shape memory or a tendency to return towards a preset shape when deflected. The shape memory polymer or metal may be triggered to return to its original, predetermined shape in response to stimuli including, but not limited to, temperature, pH, light, and exposure to water. Exemplary shape memory polymers may include without limitation, polytetrafluoroethylene (PTFE), polylactide (PLA), and ethylene-vinyl acetate (EVA). Exemplary shape memory metals may include without limitation, metal alloys of nickel and titanium (Nitinol); metal alloys of copper, zinc, and aluminum; metal alloys of copper, aluminum, and nickel; and metal alloys of iron, manganese, and silicon. In some variations, the majority or entirety of the tension element is flexible and may exert tension on the nasal tissue when the tension element is secured in place. In some variations, the tension element may be applied directly on the tissue to be altered. In some variations, the tension element may be applied to tissue adjacent, deep, superficial, or bilateral to the nasal tissue to be altered. The tension element may be of any suitable size, shape, length, or width.

In some variations, the tension element is configured to be reversible or removable. In such variations, the tension element can be configured to have at least some portion accessible above the nasal mucosa. The accessible portion can specifically comprise the securing portion at the distal end of the tension element, configured to reside above the mucosa on the concave surface of the deviation, contralateral to the body of the tension element. Alternatively, the tension element can be configured to include another or additional accessible portion or portions. The accessible portion can specifically be configured to be removed or retrieved, such as by scissors or scalpel inserted into the nostril, such that the remainder of the tension element can be pulled out of the nasal tissue without the securing portion. Alternatively, the accessible portion can be configured to be removed by another suitable method of retrieval. In such reversible or removable variations, the tension element can be easily retrieved and removed from the nasal tissue to allow the procedure to be easily reversible.

In some variations, the tension element is used to correct a nasal septal deviation. In this case, the tension element may preferentially be delivered beneath the nasal septal mucosa on the convex curvature of a deviation, but may also be configured to be placed above the nasal septal mucosa. When delivered beneath the nasal septal mucosa, a delivery device may be used to anchor a securing element, such as a T-fastener located on the distal end of tension element relative to the nasal septal cartilage. The delivery device may accomplish this using a penetrating feature or other mechanism, e.g., formed from Nitinol, spring steel, and the like, designed to deploy the securing element. The securing element, when placed, may reside above or below the contralateral nasal septal mucosa. For example, the securing element may be placed at the distal most aspect of the deviation. The proximal end of the tension element may have a penetrating feature that allows the tension element to be passed across the nasal septum to the contralateral nasal airway. Alternatively, the proximal end of the tension element may be passed across the nasal septum by way of a penetrating feature on the delivery device. Between the distal securing element and the proximal end of the tension element there may be one or more securing elements such as barbs that are designed to prevent backwards migration of the tension element. The one or more proximal securing elements may be designed to allow the tension element to gradually correct a nasal septal deviation. For example, barbs along the length of the tension element could be gradually pulled through the nasal septal cartilage until the desired correction is achieved.

In some variations, the device used for correction of a nasal septal deviation with a tension element may be designed to maintain the structural integrity of the nasal septal cartilage without significantly weakening it. In other variations, a physician may score, cut, and/or remove cartilage to facilitate the desired nasal septal deviation correction with the tension element.

Figure 6:
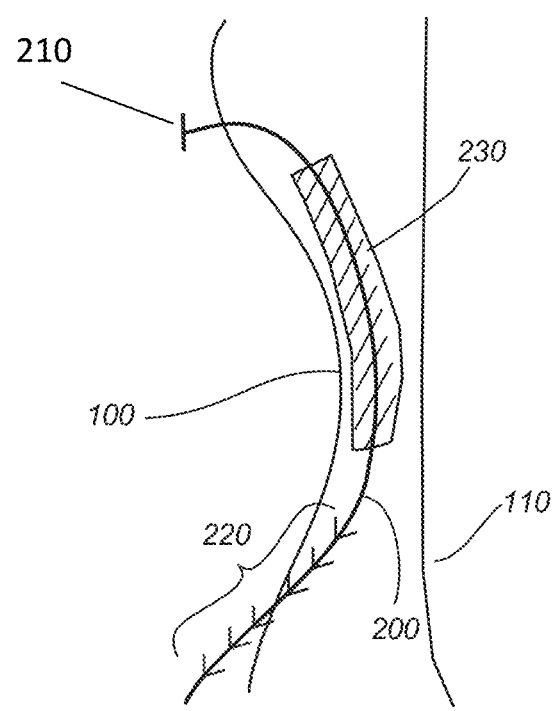
FIG. 6 depicts another exemplary tension element including a plurality of migration prevention elements and a force distributing region.

As shown in FIG. 6, in some variations, the tension element may contain one or more securing portions (210) at one or both ends. Optionally, the tension element may additionally or alternatively have one or more migration prevention elements (220) or one or more force distributing regions (230). Each of the migration prevention elements may take on the shape of a barb, ratchet, protrusion, or any other suitable configuration to prevent migration of the tension element, e.g., allowing the elements to be introduced through tissue in a first direction while preventing the elements from being pulled back through the tissue. The securing portion or portions (210) primarily functions to resist migration of the tension element through the nasal tissue and may be configured similar to a T-fastener, X-shaped fastener, expandable anchor, button, shape-retaining structure, barb, a plurality of barbs, or any other suitable structure for resisting movement. In some variations, the securing portion may be tension or position adjustable. In some variations, the tension element may be configured without the securing portions. The securing portion may be made of the same material or materials as the adjacent portion of the tension element or may be constructed from a different material or materials. The optional migration prevention element (220) may be configured as one or more barbs and may be arranged in a parallel or spiral pattern or in any arrangement suitable for securing the tension element. In some variations, such barbs may have fixed or variable sizes and may be composed of fixed or variable material or materials. In some variations, the tension element may include barbs at one end; in other variations, the tension element may include barbs along multiple regions; in other variations, all or none of the tension element may include barbs. The force distributing region (230) primarily functions to increase surface area and distribute pressure across nasal tissues. The force distributing region may be fixed or variable length and may have a fixed or variable position on the tension element. For example, in some variations, the force distributing region may be fixed in position relative to the tension element or may slide on, off, along, or around the tension element. The force distributing region may be composed of the same material or materials as the adjacent portions of the tension element or may be composed of a different material or materials. In some variations, the tension element contains one force distributing region. In other variations, the tension element contains no force distributing regions or multiple force distributing regions. In some variations the tension element may have a needle at none, one, or a plurality of ends of the tension element. In some variations the needle or needles may be flat or curved. The needle or needles may be made of any suitable material to allow for the tension element to be passed through tissue.

In some variations, the tension element may be solid. In some variations, the tensioning agent may be porous or non-porous. In some variations, the tension element may be configured to promote tissue regrowth or prevent blood clot formation. The tension element may optionally be designed to be coated with, bonded to, impregnated with, or otherwise release a functional agent suitable for altering a physiological property. The functional agent may be configured as a therapeutic agent such as an antibiotic agent, anti-inflammatory agent, growth promoting agent, hemostatic agent, clot prevention agent, analgesic, or any suitable drug, molecule, or compound to achieve a therapeutic effect.

The tension element may be secured partially or entirely beneath a nasal mucosa (110) or maybe exposed within the nasal airway.

In some variations, the tension element may have a monofilament or suture-like structure. In other variations, the tension element may have a rod-like structure, a braided structure, a woven structure, a nonwoven structure (e.g., when electrospun), a flat structure, or any other structure suitable for providing the desired mechanical properties. In some variations, all or a component of the tension element may be degradable, absorbable, resorbable, biodegradable, or bioabsorbable. Such variations may include components comprising LPLA (Poly(L-lactide)), DLPLA (Poly(DL-lactide)), LDLPLA (Poly(DL-lactide-co-L-lactide)), LPLA-HA (Poly(L-lactide) with hydroxylapatite), PGA (Poly(glycolide)), PGA-TMC (Poly(glycolide-co-trimethylene carbonate) or polyglyconate), PDO (Poly(dioxanone)), LPLG (Poly(L-lactide-co-glycolide)), DLPLG (Poly(DL-lactide-co-glycolide), a copolymer of any of these or other suitable polymers, or any other suitable material. In some variations, the tension element may be non-biodegradable or non-bioabsorbable or removable at a later point in time. In other variations, the tension element may be permanent. In some variations, at least one portion of the tension element may be modified after placement such as by trimming an excess portion of one end of the tension element.

In some variations, the tension element may, especially when deployed submucosally using an absorbable polymer, induce a remodeling response in a target tissue. In some variations where nasal cartilage is a target tissue, this remodeling response may include the formation of a pseudocapsule that functions to first protect against pressure necrosis, as is reported after the implantation of some non-absorbable implants, and second enable chondrocyte nutrition. The pseudocapsule may, from a histological view, enable the cartilage underneath the tension element to remain completely unchanged. In some variations, the tension element may also induce the recruitment or formation of new chondroblasts and the deposition of new cartilage at the border of the pseudocapsule or tension element. In some variations, this remodeling process may be optimized to occur within 5-25 weeks. In some variations, the process may be further optimized such that chondroblasts and new cartilage growth along the border of the cartilage defect occurs after about five weeks and absorption of the tension element is appreciable after about eight to twelve weeks, with complete absorption within about twenty-five weeks.

Figure 7:
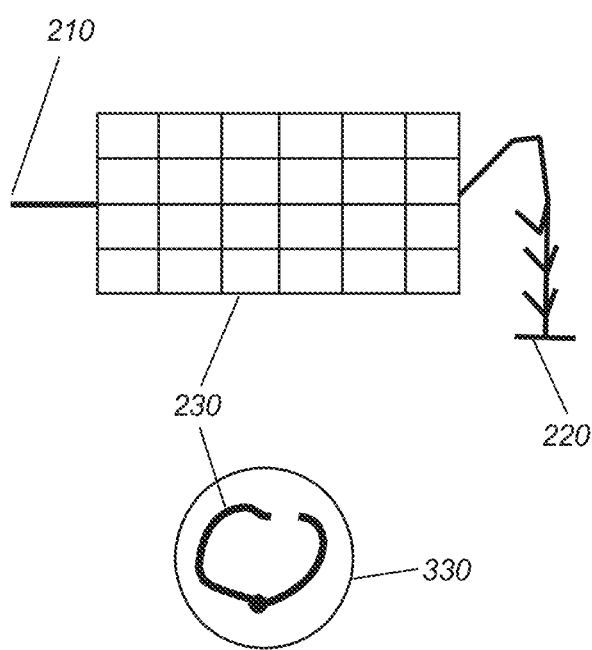
FIG. 7 depicts a further exemplary tension element including a plurality of migration prevention elements and a mesh-like force distributing region.

As shown in FIG. 7, in some variations the force distributing region (230) may have a solid, mesh-like, or other suitable configuration such that the force distributing region is able to be compressed in a delivery element. For example, as shown in FIG. 7, the force distributing region (230) may optionally be configured to be rolled in an elongated shaft (330) of a delivery tool.

Figure 8:
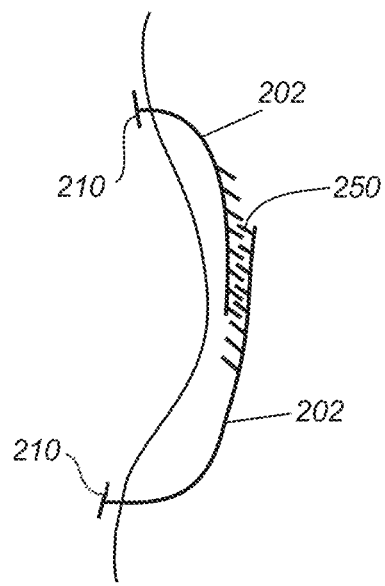
FIG. 8 depicts yet another exemplary tension element including multiple components that interact in an adjustable manner to apply tension to tissues.

As shown in FIG. 8, in some variations, the tension element (200) may be configured as at least two multiple components (202) that may contain an interaction mechanism (250). The interaction mechanism primarily functions to secure the multiple components with relative position in an adjustable manner. In some variations, the interaction mechanism may be configured as a catching mechanism, such as a zipper, ring grip, cinch, clasp, webbing buckle, or pressure gripping. In some variations, the interaction mechanism may be configured as a locking mechanism such as a button, tongue buckle, or snap buckle. In some variations, the interaction mechanism may be configured as a pinning mechanism, adhesive mechanism, or in any other suitable configuration for resisting the relative motion of the multiple components. In some variations, the interaction mechanism may set permanently. In some variations, the interaction mechanism may be adjustable over time or at different times. In some variations, the multiple components are secured on the non-interacting end with a position securing or movement resisting element or elements. In some variations, the multiple components are connected as one tension element, but the relative position of each component may be adjustable and securable via an interaction mechanism.

In some variations, the tension element may be fitted with an energy delivery element, such as one or more permanent or temporary electrodes, heating elements, or other energy delivery mechanism that allow the tension element to deliver energy to the nasal tissue. The energy delivery mechanism may be used to augment reshaping or remodeling of the nasal tissue by application of heat, electric current, or any suitable form of energy. In some variations, the energy delivery mechanism may be removed after energy is applied. In some variations, the energy delivery mechanism may be implanted with the tension element. In some variations, the energy delivery mechanism may be bioabsorbable or biodegradable. In some variations, the energy delivery mechanism is attached directly to the tension element. In some variations, the energy delivery mechanism is situated adjacent to the tension element.

In some variations, the tension element may be configured with a fluid delivery mechanism such as a conduit, channel, or other mechanism for suitable delivery of fluid to nasal tissue, as previously described. This fluid delivery mechanism may allow for the passage of fluid to achieve a therapeutic or physiologic effect. For example, the fluid delivery mechanism may be used to deliver a cold gas or liquid for the purposes of cryotherapy.

Figure 9:
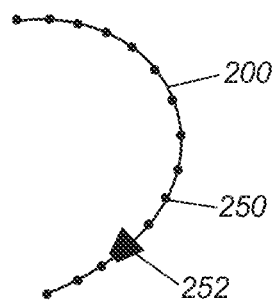
FIG. 9 depicts an exemplary tension element according to another variation including an adjustable securing element.

As shown in FIG. 9, the tension element (200) may optionally have an adjustable securing element (252) that can alter the tension, pressure, or position of the tension element. Optionally, multiple adjustable securing elements may be provided on the tension element (not shown), e.g., initially adjacent each end of the tension element. In some variations, the adjustable securing element uses a ball-in-cone ratcheting mechanism. In one variation, the tension element has one or more eminencies, protrusions, sphere, or tuberosities (250) positioned along its length. These protrusions are designed to pass first through a dilated end of the adjustable securing element (252) and then through a narrowed end of an adjustable securing element. The protrusion (250) and adjustable securing element (252) interaction may allow the tension element to be gradually tightened or shortened in a one-way fashion to prevent retraction and/or to augment pressure application of the tension element. In one variation, these protrusions are spherical in shape. In another variation, the adjustable securing element (252) may have a reversible configuration to allow the protrusions (250) to be retracted back through adjustable securing element. The protrusions (250) and adjustable securing element (252) may be made of a same or different material as the tension element (200).

Figure 10:
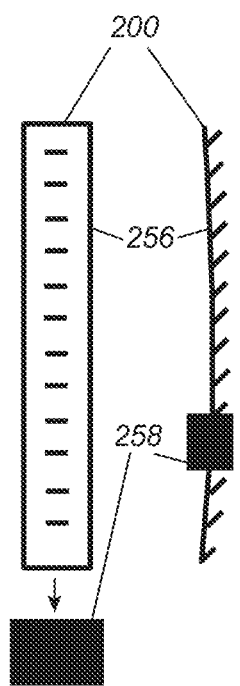
FIG. 10 depicts yet another exemplary tension element where the adjustable securing element interacts with ribs or fins positioned along the length of the tension element.
Figure 11:
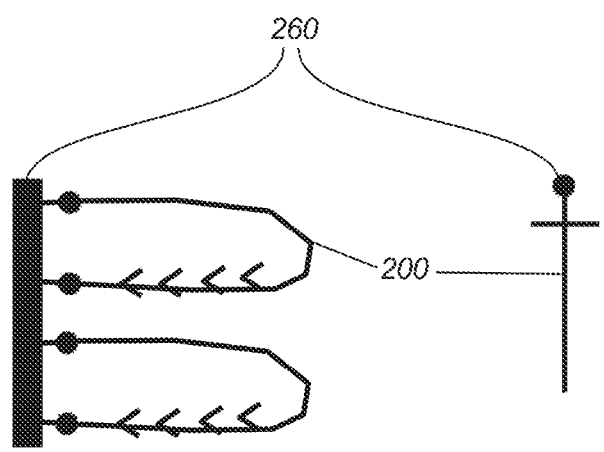
FIG. 11 shows a device according to another variation where multiple tension elements are held together with a detachable element.

As shown in FIG. 10, in some variations, the adjustable securing element (258) interacts with ribs or fins (256) positioned along the length of the tension element and are designed to be advanced through the adjustable securing element (258) in a one-way fashion. In another variation, the adjustable securing element (258) may be altered to allow the tension element to be pulled in the reverse direction. The ribs (256) and adjustable securing element (258) may be made of a same or different material as the tension element (200). The ribs may be oriented parallel, orthogonal, or oblique with respect to the longitudinal axis of the tension element. The tension element and adjustable securing element may be deployed by the same or different device.

In some variations, multiple tension elements may be held together with a detachable element (260). The detachable element (260) is designed to allow a plurality of repeating tension elements to be held together for loading into a delivery device. The detachable element may be made of a polymer, metal, composite, alloy, or any suitable material to allow the intended functionality. In another variation, multiple tension elements may be held together in a cartridge. In another variation, multiple tension elements may be held together in a sheet or any other configuration that allows a plurality of tension elements to be delivered either individually or simultaneously via the deployment mechanism of a delivery device.

Figure 12:
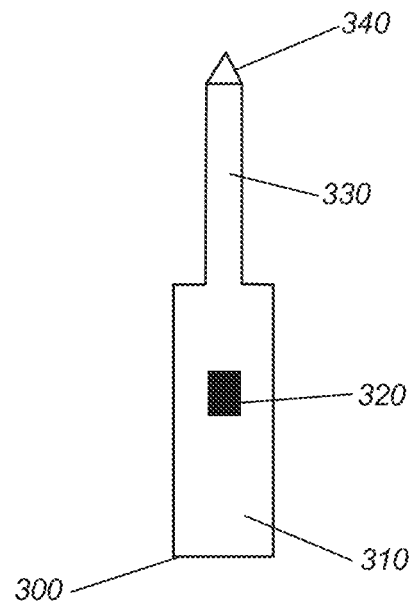
FIGS. 12 and 13 depict exemplary devices for delivering tension elements.
Figure 13:
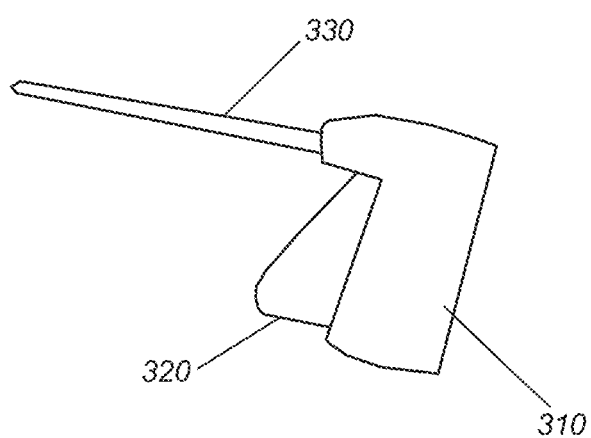

Turning to FIGS. 12 and 13, an exemplary variation of a delivery device (300) is shown that is configured to deliver a tension element for altering the shape of a nasal tissue includes a body (310), at least one action mechanism (320), an elongated shaft (330), and an optional tip (340). In some variations, the deployment device (300) may have a body (320) of an elongated or "pistol grip" shape (FIG. 13). In some variations, the at least one action mechanism (320) may be on the anterior, posterior, superior, inferior, or lateral aspect of the deployment device. The action mechanism may be a trigger, button, lever, arm, or any alternative suitable conformation in order to achieve a desired function. In some variations, the optional tip (340) may be blunt or sharp. In some variations, the tip (340) may be parallel with or oriented at an angle relative to the elongated shaft (330). In some variations, the elongated shaft (330) and/or tip (340) houses a tension element and placement mechanism to deliver the tension element through, on, or adjacent to the nasal tissue.

Figure 14:
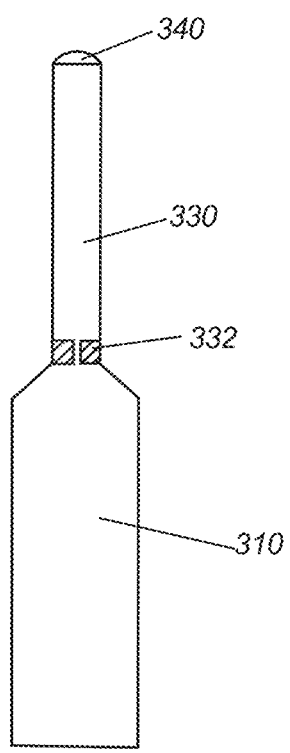
FIG. 14 depicts an exemplary delivery device according to another variation that includes an attachment site on the delivery device shaft for attachment to, or removal from, the body of the device.

As shown in FIG. 14, in some variations, the elongated shaft (330) may include an attachment site (332) for attachment to, or removal from, the body of the device (310). In such variations, the device may be configured to utilize various attachments using the same attachment site on the body of the device. In some variations, this will allow the elongated shaft to be replaced with another identical elongated shaft with the same configuration. For example, in the case where the elongated shaft includes only one tension element, it may be necessary to use multiple elongated shafts throughout the same procedure. Different attachments may be configured with the same primary function and different sizes and shapes or may be configured with alternate functions. In some variations, the body of the device may be configured with multiple attachment sites.

In some variations, the delivery device may be configured to allow for determining the extent of tissue shape alteration. For example, the extent of nasal septal deviation correction. In one variation, the extent of shape change is determined by visual inspection of the nasal airway diameter. In another variation, the delivery device is configured to measure a force. For example, the delivery device may be configured to measure tension along the length of the tension element.

Figure 15:
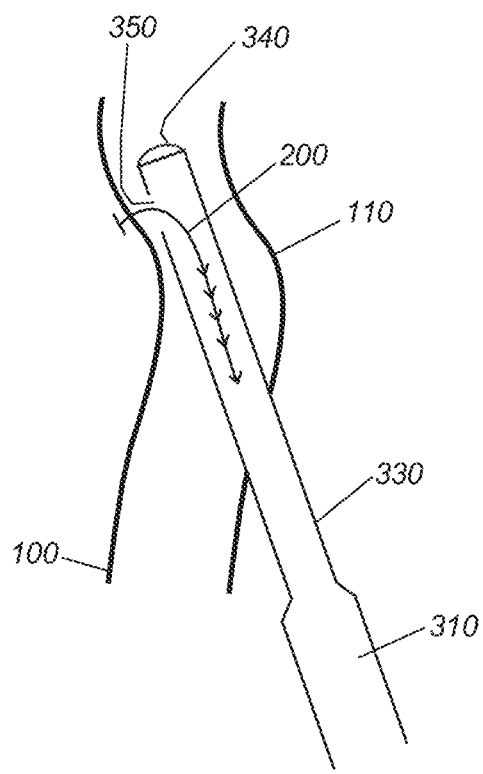
FIG. 15 depicts an exemplary delivery device including a blunt tip and an opening on the side of the delivery device shaft for lateral or orthogonal deployment of a tension element relative to the elongated shaft.

As shown in FIG. 15, some variations of a delivery device for altering the shape of a nasal tissue may include a blunted tip (340) of an elongated shaft (330). In this variation, the elongated shaft may optionally house at least one tension element (200) to be used to alter the shape of the nasal tissue. The elongated shaft may have an optional opening (350) that is on the side of the elongated shaft allowing for lateral or orthogonal deployment of the tension element relative to the elongated shaft. In another variation, an opening (350) for delivery of a tension element may be located at the distal end of the elongated shaft at its tip (340) to allow for parallel or oblique delivery of the tension element relative to the shaft. In some variations, the delivery device (300) may be configured to accept more than one tension element via a cartridge, sheet, or any other suitable configuration of a plurality of braces. In a variation where the delivery device is used for altering the shape of a nasal septum (100), the tip of the delivery device (340) may be inserted beneath the septal mucosa (110) and advanced to a desired position. In this case, the tip may contain a visualization element that can be used to track the position of the tip beneath the septal mucosa. Once at the desired site of placement, the delivery device may be activated to place at least one securing element of at least one tension element. In other cases, the delivery device may be positioned above the nasal septal mucosa before activation for placement of at least one securing element of at least one tension element.

Figure 16:
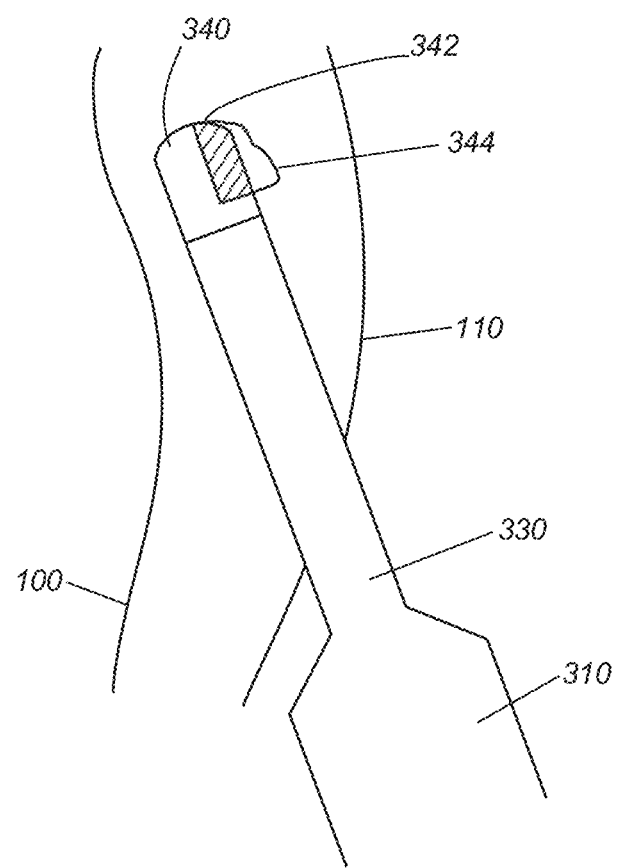
FIG. 16 depicts another exemplary delivery device including a visualization element at the tip of the device.

As shown in FIG. 16, some variations of a delivery device for altering the shape of a nasal tissue may include an optional visualization element (342) on the optional tip (340). The visualization element primarily functions to aid in positioning the device while it is beneath the nasal mucosa (110). The visualization element may be configured as an LED, a magnetic component, an electronic transmitter or receiver, or may be configured as any other material suitable for localization beneath the mucosa. In some variations, the tip of the delivery device may include a fin (344). The fin primarily functions to displace the overlying mucosa to aid in positioning the device while it is beneath the nasal mucosa (110). The fin may be configured to temporarily deploy or change shape to allow for transient displacement of the overlying mucosa. In some variations, the elongated shaft or tip of the delivery device may be adjustable in length. This may be accomplished via a telescoping mechanism, sliding mechanism, or any other suitable mechanism to alter the length of the elongated shaft or tip. In other variations the elongated shaft or tip may have an adjustable diameter. The elongated shaft or tip may also me malleable or shape adjustable. The elongated shaft or tip may also be able to rotate along its long axis. The elongated shaft or tip may also be fitted with an aspiration element to allow for suctioning of fluid. The elongated shaft or tip may also be fitted to hold or receive an endoscope. The elongated shaft or tip may also be fitted with a light to allow for enhanced visualization. The tip (340) may be of any suitable shape to allow for atraumatic maneuvering in the nasal airway and/or submucosal space. For example, the tip may be cylindrical or flat. It may alternatively have a non-symmetric configuration such as a shovel or scoop tip. In some variations, the tip may also be configured to include a cutting edge. The cutting edge may be configured to be retractable or fixed and can be used to facilitate introduction of the tip into a nasal tissue, separation of nasal tissues, or otherwise assist with positioning of the device.

Figure 17:
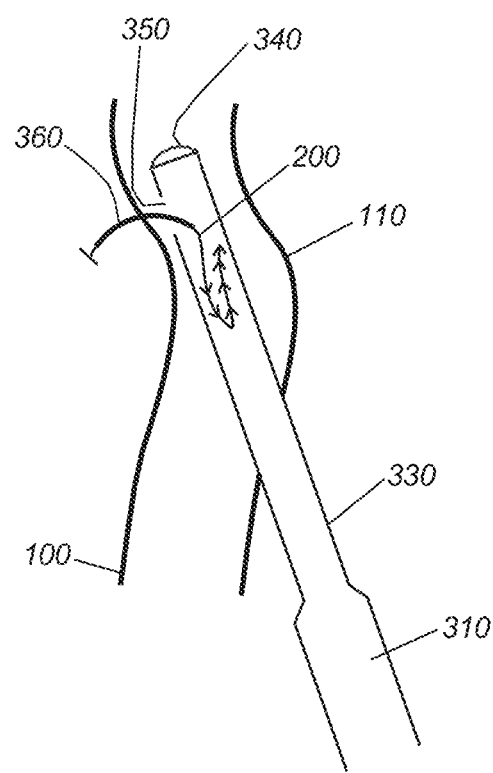
FIG. 17 depicts yet another exemplary delivery device including a placement mechanism to assist with deployment of a tension element into tissue.

As shown in FIG. 17, some variations of a delivery device for altering the shape of a nasal tissue have a placement mechanism (360) (also known as a delivery or deployment mechanism) that enables placement of a tension element. The placement mechanism may optionally be designed to extend out of an opening in the elongated shaft (350) to pierce or otherwise traverse the nasal tissue. Such an opening may be placed at the distal end of the tip or on the side of the elongated shaft or in any other suitable position to allow for optimal placement of the tension element. The placement mechanism (360) may be activated by an action mechanism located on the delivery device (310). In some variations, the placement mechanism may be pointed or sharp. It some variations, the placement mechanism may have an arc or other suitable shape appropriate for the desired function of penetrating or crossing the nasal tissue. Optionally, the placement mechanism may be fitted with an energy delivery element to facilitate tissue penetration. Optionally, the placement mechanism (360) may have an inner cannula which houses a tension element (200). In other variations the tension element may otherwise be secured to the outer portion of the placement mechanism. Once activated, the placement mechanism (360) may eject or otherwise release a desired end of the tension element (200). Once deactivated by means of releasing its action mechanism, the placement mechanism (360) may retract back through the opening (350) and into the housing of the elongated shaft (330).

Figure 18:
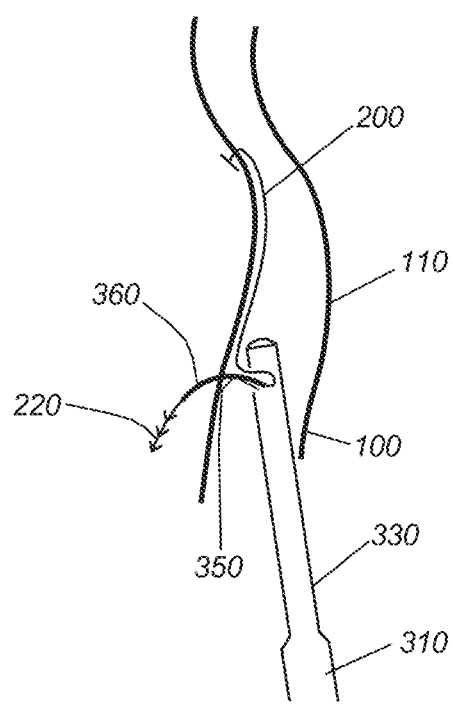
FIG. 18 depicts a further exemplary delivery device that places a first securing element at the distal end of a tension element, and a second securing element or migration prevention element at the proximal end of the tension element.

As shown in FIG. 18, one variation of the delivery device is configured with a placement mechanism (360) to allow for a first placement of a securing element (210) beneath the nasal septal mucosa (110) and across the nasal septal cartilage (100) at the distal end of the tension element (200) followed by a second placement of a securing element or migration prevention element (220) at the proximal end of the tension element. In some variations, the placement mechanism (360) has a reloading action such that it is able to capture the next desired aspect of the current or next tension element. In some variations, the placement mechanism (360) is designed to reload with an additional tension element fed from a cartridge, sheet, or other suitable configuration of a plurality of tension elements.

Figure 19:
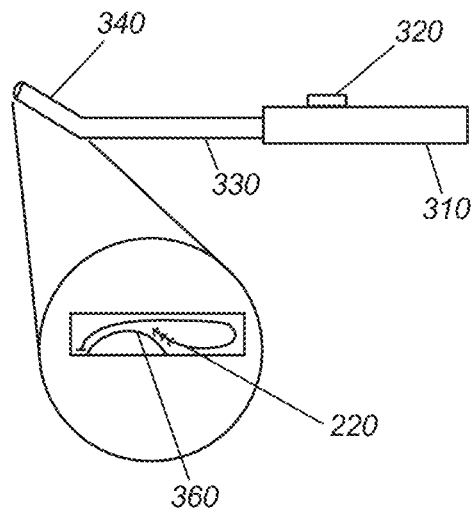
FIG. 19 depicts an exemplary delivery device including a retractable mechanism for deploying a tension element into tissue.

As shown in FIG. 19, one variation of a delivery device for altering the shape of a nasal tissue has a placement mechanism (360) that captures the first end of the tension element. An activation mechanism (320) may be used to protrude the placement mechanism (360) such that the placement mechanism penetrates or otherwise crosses the nasal tissue and subsequently ejects the first end of the tension element. Once deactivated by means of releasing the action mechanism, the placement mechanism (360) may retract back through the opening (350) and into the housing of the tip (340) and/or 61 longateed shaft (330). In some variations, the placement mechanism will be designed to capture the second end (220) of the tension element such that it may be placed at a different location from the first end.

Figure 20:
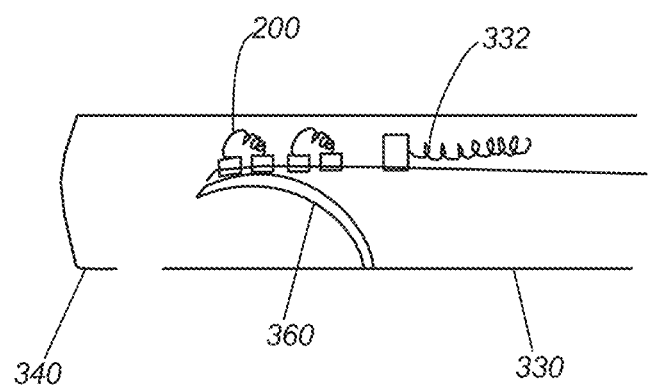
FIGS. 20 and 21 depict other exemplary delivery devices that include placement mechanisms having a reloading element.

As shown in FIG. 20, one variation of a delivery device for altering the shape of a nasal tissue has a placement mechanism (360) with a reloading element (332) that is capable of reloading the placement mechanism with additional ends of additional tension elements (200). This function allows the user to place multiple tension elements with a single device without having to insert additional tension elements into the device. After ejection of a first end of a tension element, the reloading mechanism (352) functions to load the second end of the current tension element or first end of the next tension element into the placement mechanism. The reloading mechanism may include a spring, push rod, or any suitable configuration to allow for the intended purpose.

Figure 21:
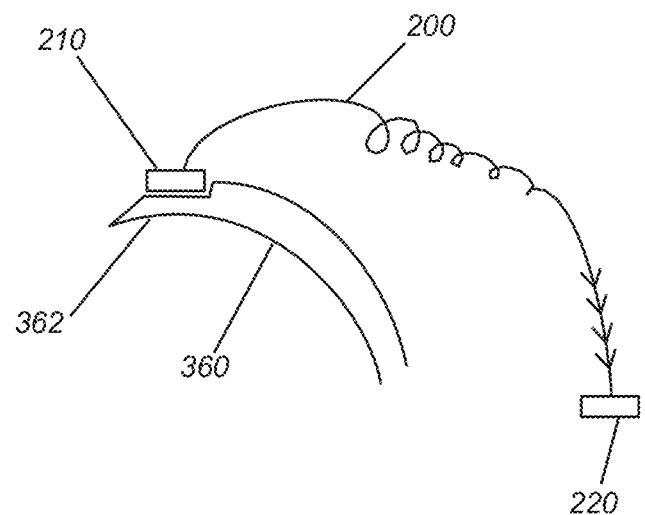

As shown in FIG. 21, one variation of the placement element (360) may have a receiving feature (362) that facilitates reloading of the next desired end of a tension element (210 or 220) by the reloading mechanism (332). This feature is designed to interact with either end of the tension element such that it temporarily secures the tension element onto the placement mechanism (360).

Figure 22:
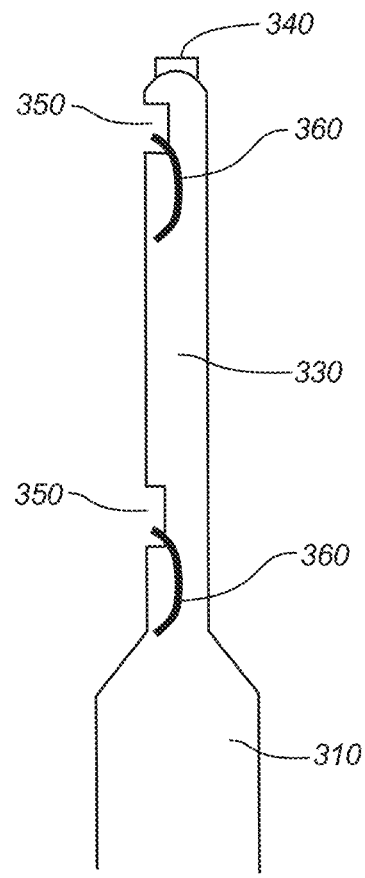
FIG. 22 depicts yet another exemplary delivery device including a plurality of placement mechanisms.

As shown in FIG. 22, in some variations of a delivery device for altering the shape of a nasal tissue, the device may be configured with multiple placement mechanisms (360). In such variations, the placement mechanisms may be configured to deploy multiple securing elements of one or more tension elements simultaneously or in sequence or may be configured to deploy multiple sections of a single tension element simultaneously or in sequence. In some variations, by utilizing multiple placement mechanisms, the device may be configured to apply the tension element into a final, secured position and may reduce the need to secure the tension element after its initial deployment. The optional multiple placement mechanisms may be located either in serial along the length of an elongated shaft or tip, or adjacent to each other at a specific length along the elongated shaft or tip.

Figure 23:
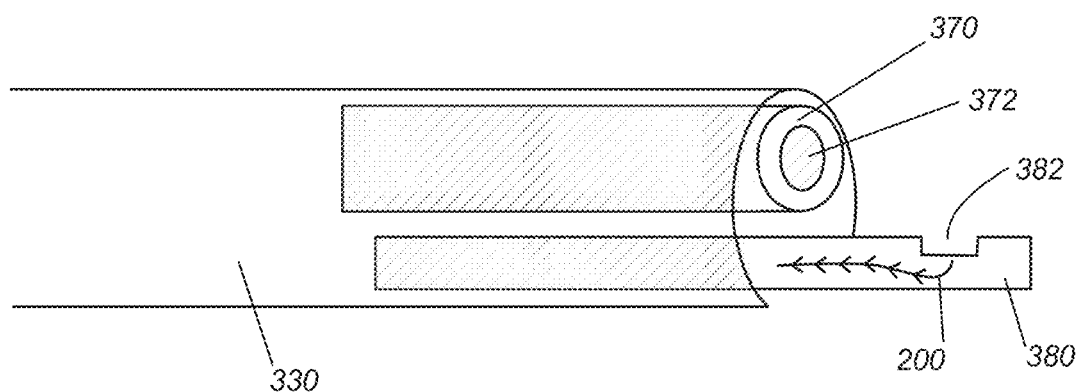
FIG. 23 depicts a further exemplary delivery device including a visualization element and an actuator arm that facilitates deployment of a tension element.

As shown in FIG. 23, some variations of a delivery device for altering the shape of a nasal tissue may include a visualization instrument (370) and/or an actuator arm (380) within the elongated shaft (330). The visualization element primarily functions to aid in visualization and may be configured as a disposable or reusable endoscope that is either flexible or rigid, a fiberoptic visualization device, a CCD, CMOS or other camera, or any another other suitable imaging or visualization modality. The visualization instrument may be configured with a wired connection or may be wireless. In some variations, the visualization instrument is included within the device; in other variations, the device is configured to house an external or separate visualization instrument of standard dimensions that may be inserted prior to use and removed afterwards. Optionally, the visualization instrument may include an adjustable lens (372) that is configured for visualization within the nasal tissue. In some variations, the delivery device may include an actuator arm (380) that may extend from within the elongated shaft (330). The actuator arm may extend parallel to the elongated shaft or may have joints or axes to enable additional degrees of positional freedom. The actuator arm may include an opening (382) to facilitate deployment of the tension element (200).

Figure 24:
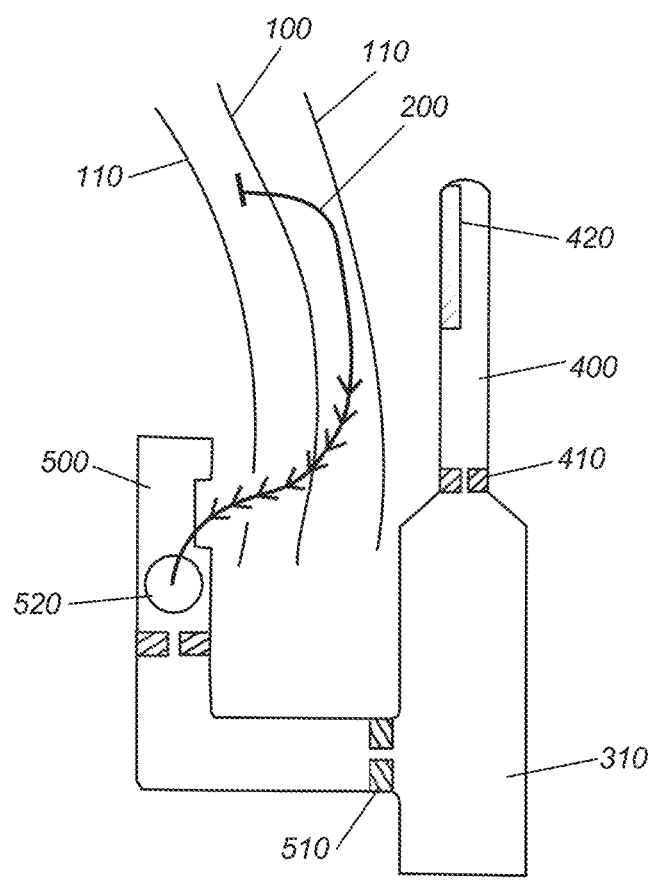
FIG. 24 depicts an exemplary delivery device according to another variation that includes a mechanical element for manipulating tissue into a desired altered shape before securing the shape with a tension element, and a tightening mechanism for tightening the tension element from its initial deployment position to a final position.

As shown in FIG. 24, some variations of a delivery device for altering the shape of a nasal tissue may be configured to adjust the tension element (200). In some variations, the device may include a mechanical element (400) that primarily functions to mechanically manipulate the nasal tissue into a desired altered shape before securing the shape with the tension element. In some variations, the mechanical element may be attachable to the body of the device (310) via an attachment site (410). In some variations, the mechanical element may incorporate a sensing modality (420) to facilitate the alteration of a nasal tissue to a desired shape. In exemplary variations, the sensing modality or modalities may be selected from sensors including, but not limited to, pressure sensors, accelerometers, force meters, angular sensors, tilt sensors, distance sensors, or any other sensing modality suitable for assessing the shape of the nasal tissue. In some variations, the device may include a tightening mechanism (500). In some variations, the tightening mechanism is attached to the main body (310), via an attachment site (510). The tightening mechanism primarily functions to secure the tension element (200) from its initial deployment to a final position. Optionally, the tightening mechanism may include a locking mechanism (520) that functions to secure the tension element to the device so that it can be tightened in a controlled fashion. In other variations, the tightening mechanism has a sensor feedback device that adjusts the rate, strength, speed, or other measurable aspect of tightening relative to measurements taken from an applicable sensor. For example, in one variation, the tightening element may have a force or tension meter that modulates tightening based on output from this sensor. In some variations, tightening may cease once a certain threshold is detected by such a sensor.

Figure 25:
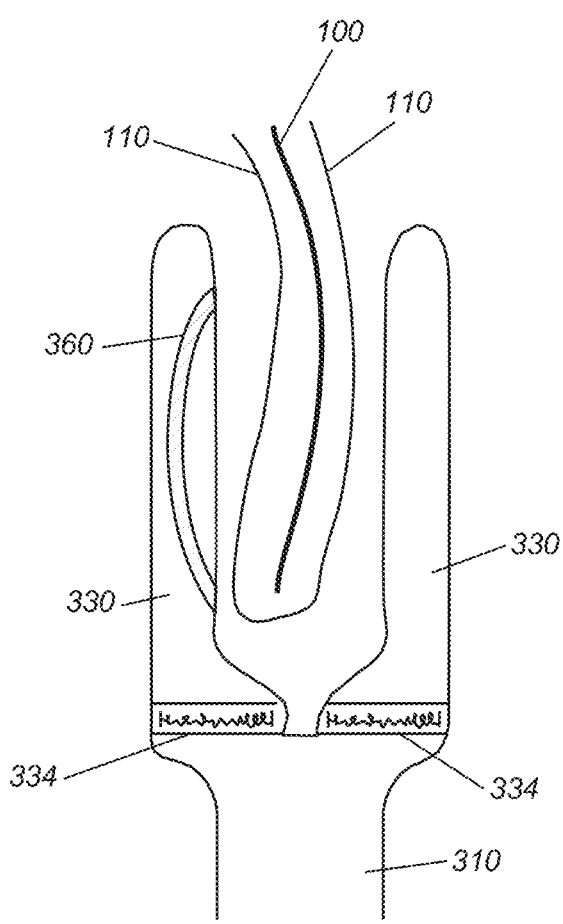
FIGS. 25 and 26 depict an exemplary device for delivering a tension element that alters the shape of the nasal septum.
Figure 26:
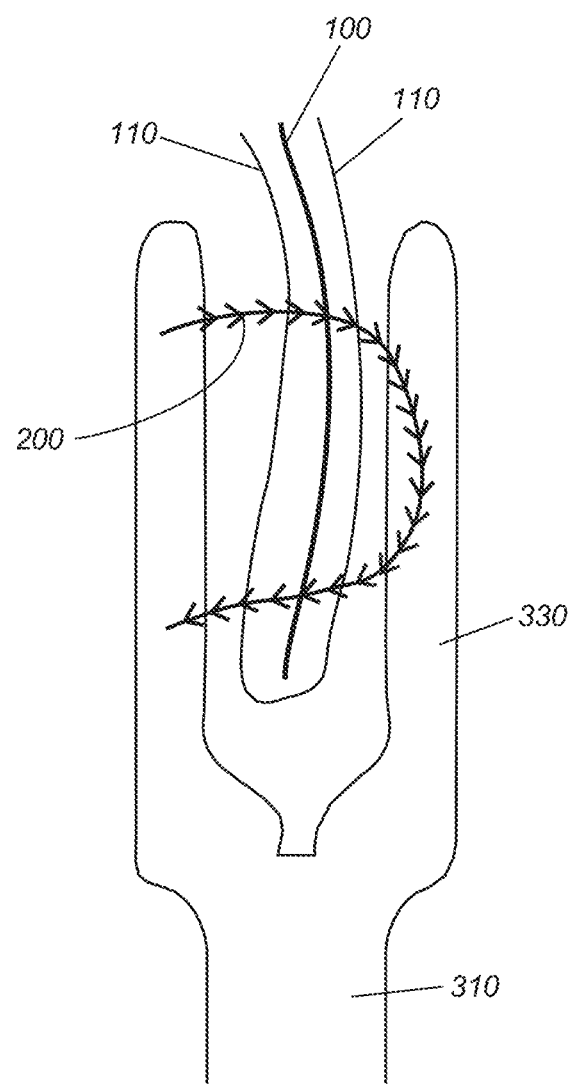

As shown in FIG. 25, some variations of a delivery device for altering the shape of a nasal tissue may be specifically configured for altering the nasal septum and may be configured to be deployed bilaterally, on either side of the septum. In some variations, the device may include multiple elongated shafts (330). In some variations, the relative position of the elongated shafts may be adjusted via one or more adjustable mechanisms (334). The adjustable mechanisms may function to manipulate the position of the elongated shafts in order to position the device for deployment of a brace across the nasal septal cartilage. The adjustable mechanisms may also function to apply force to the nasal septal cartilage or nasal bones to at least temporarily alter the shape before securing the brace. The device may include a deployment mechanism (360). In some variations, the deployment mechanism is configured to pass the brace between the elongated shafts and across the nasal septal cartilage, as shown in FIG. 26.

Figure 27:
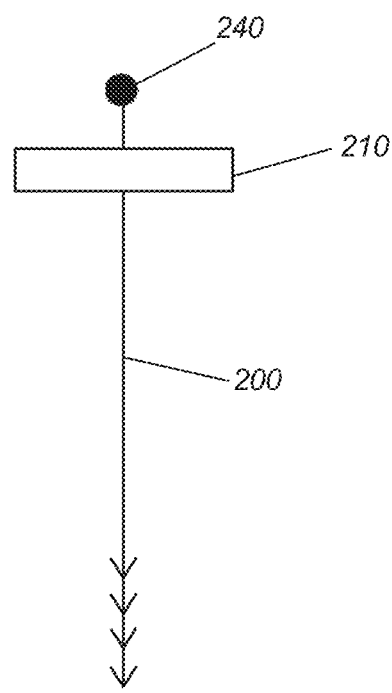
FIGS. 27 and 28 depict exemplary tension elements including components for securing the tension element in tissue.

As shown in FIG. 27, some variations of a tension element have an enlarged distal end (240) relative to the body of the tension element (200). The distal end may be any shape including but not limited to circular, spherical, hemispherical, rectangular, x-shaped, spiral, and the like. It may be designed to interface with a securing element (210); for example, as a ball-in-joint conformation. In some variations, the securing element moves in any plane relative to the tension element. In the particular variation shown in FIG. 27, the securing element is a rectangular structure that slides along the long axis of the tension element.

Figure 28:
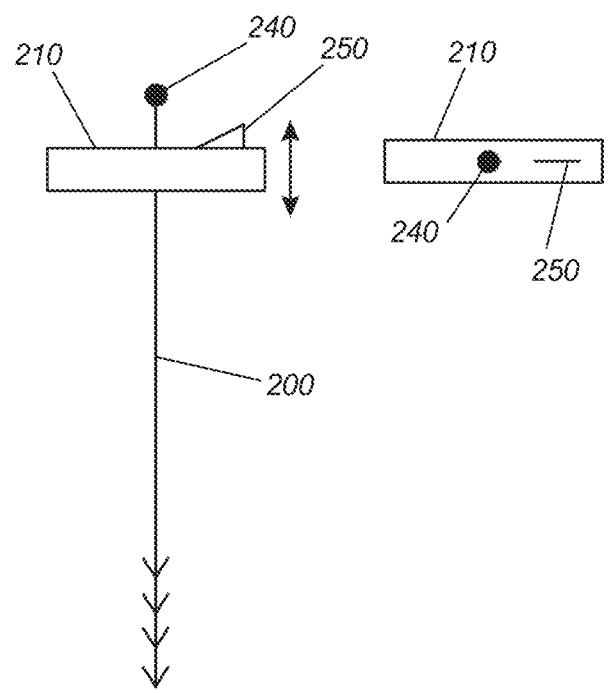

As shown in FIG. 28, in some variations the securing element may have a tissue interaction feature (250) that is designed to catch on tissue and cause the securing element to rotate, change position, or change shape. For example, shown in FIG. 28 is a fin feature that is triangular in shape such that when the securing feature is passed through tissue with the end of the securing feature opposite the end containing the fin, the fin is allowed to pass through the tissue but not back. In some variations, the securing element may be designed to interface with the placement mechanism of a delivery device such that the securing element is either passively or actively displaced from the placement mechanism of a delivery device.

Figure 29:
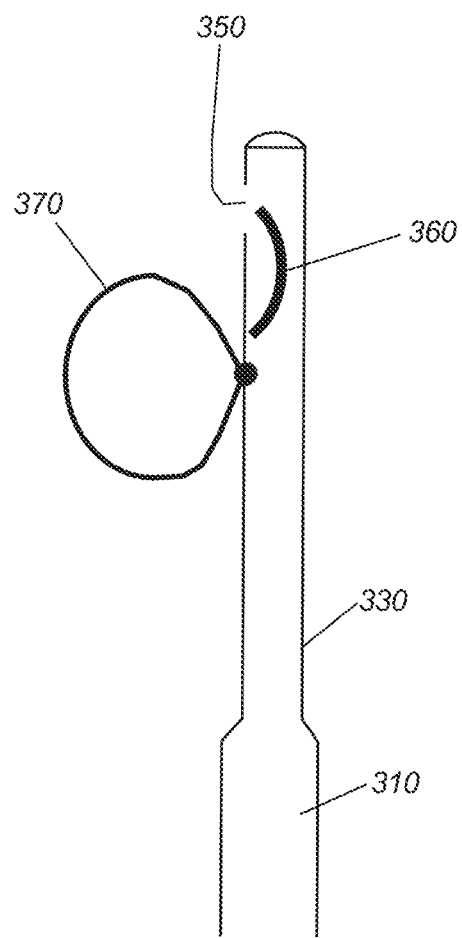
FIG. 29 depicts an exemplary delivery device including an expandable tissue displacement feature.

As shown in FIG. 29, some variations of a delivery device may include an expandable tissue displacement feature (370) that is designed to at least temporarily move tissue. One example of such an expandable tissue displacement feature would be an inflatable balloon designed to at least temporarily fracture or manipulate a nasal tissue into a desired shape.

Figure 30:
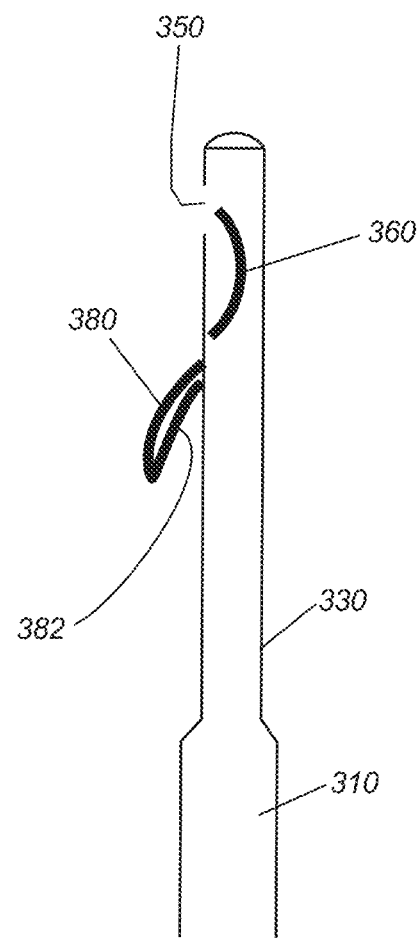
FIG. 30 depicts another exemplary delivery device including a tissue cutting feature.

As shown in FIG. 30, some variations of a delivery device may include a tissue cutting feature (382). In some variations, this tissue cutting feature may be housed within a deployable, expandable, adjustable, rigid, and/or flexible housing (380) such that the cutting feature does not engage with a tissue when the delivery device is moved in one direction but does engage with a tissue when the delivery device is moved in another direction.

Figure 31:
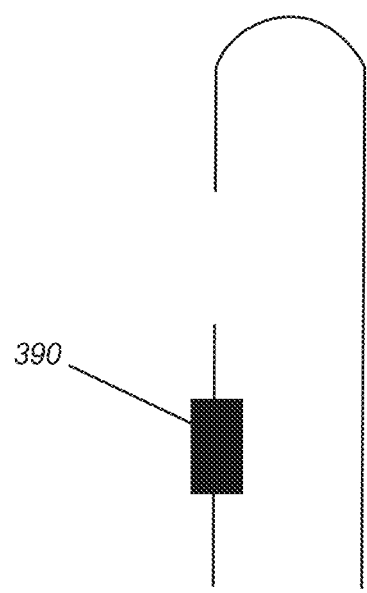
FIG. 31 depicts yet another exemplary delivery device including a tissue reduction feature.

As shown in FIG. 31, some variations of a delivery device include a tissue reduction feature (390). In one variation, the tissue reduction feature may be a motorized rotational burr designed to grind or file a tissue. The delivery device may include a housing for a battery or motor and may have a button or switch designed to turn the tissue reduction feature on or off.

Figure 32:
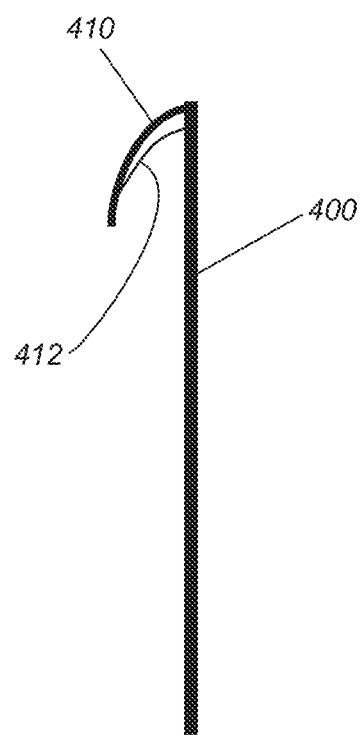
FIGS. 32 and 33 depict a further exemplary delivery device including a tissue cutting instrument that does not engage tissue when moved in a first direction, but which engages tissue when moved in a second direction.
Figure 33:
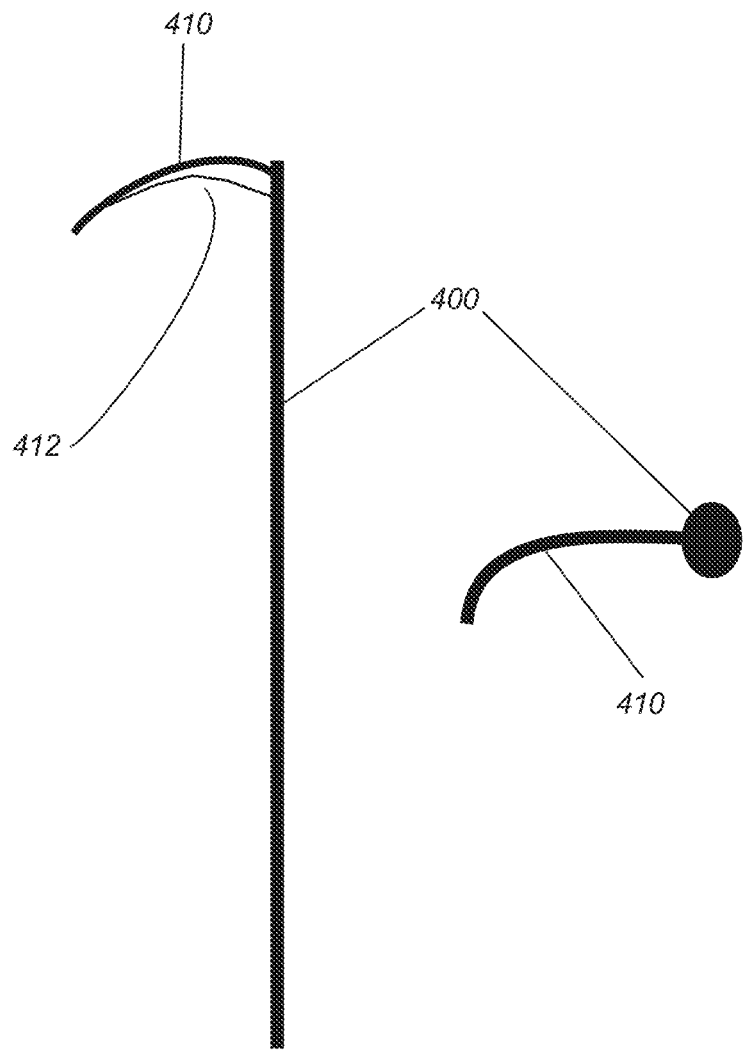

As shown in FIGS. 32 and 33, some variations of a device may include an accessory tissue cutting instrument (400). In some variations, this tissue cutting instrument includes a tissue cutting feature (412), which may be housed within a deployable, expandable, adjustable, rigid, or flexible housing (410) such that the cutting feature does not engage with a tissue when the cutting instrument is moved in one direction but does engage with a tissue when the cutting instrument is moved in another direction.

Figure 34:
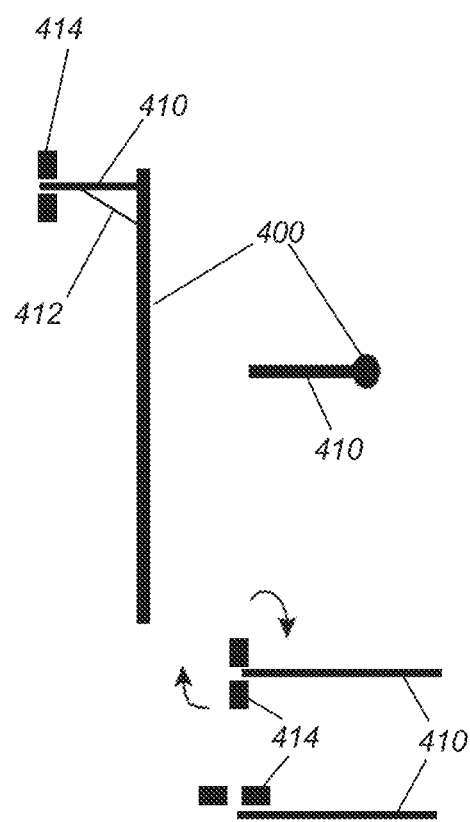
FIG. 34 depicts an exemplary accessory tissue cutting instrument including a head feature having first and second positions, and which allows puncturing through tissue in the first position but prevents pull back through the tissue when in the second position.

As shown in FIG. 34, some variations of an accessory tissue cutting instrument include a rotatable or expandable head feature (414) that changes from a first to a second position such that the instrument is able to puncture through a tissue in its first position but not pull back through when in its second position.

Figure 35:
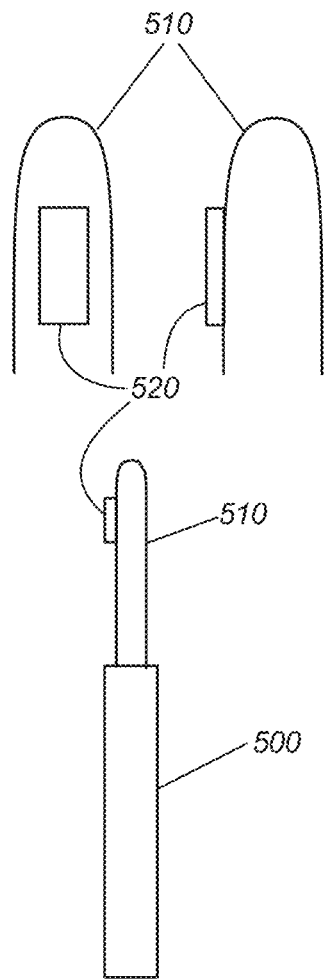
FIG. 35 depicts an exemplary accessory tissue reduction instrument designed to file or grind tissue.

As shown in FIG. 35, some variations of a device include an accessory tissue reduction instrument (500). In one variation, the tissue reduction instrument has a body, an elongate shaft (510), and a tissue reduction feature (520). In some variations, the tissue reduction feature includes ridges, ribs, or other features that allow the tissue reduction feature to file a tissue when manually moved. In other variations, the tissue reduction feature may be a motorized rotational burr designed to grind or file a tissue. The tissue reduction instrument may include housing for a battery or motor and may have a button or switch designed to turn the tissue reduction feature on or off.

Figure 36:
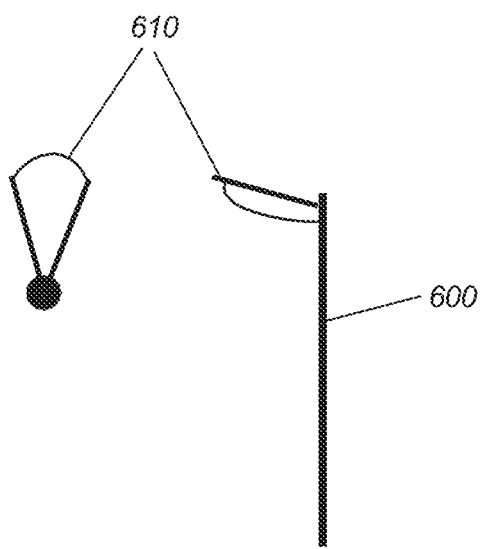
FIG. 36 depicts an exemplary accessory tissue displacement instrument.

As shown in FIG. 36, some variations of a device may include an accessory tissue displacement instrument (600). This instrument may have an elongate shaft and a head (610) that when moved, rotated, expanded, or otherwise activated is capable of at least temporarily displacing tissue. In one variation, this tissue displacement instrument may be designed in such a way that when the instrument is rotated about the axis of the elongate shaft the head also rotates such that the tissue is at least temporarily displaced away from the elongate shaft. In the case of nasal septal deviation secondary to deviation of the bony nasal septum, this may involve inward fracture of the bony septum so as to move it toward a more straightened conformation. In the case of nasal septal deviation, this instrument may be placed above or below the nasal septal mucosa.

Figure 37:
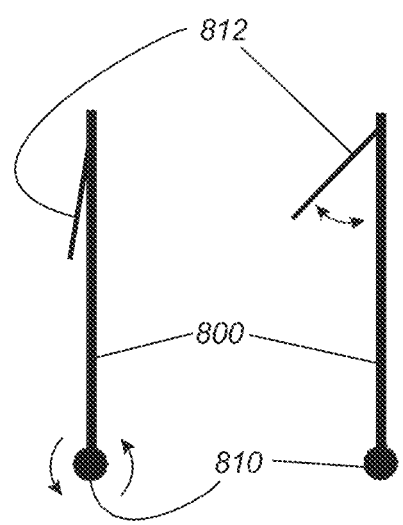
FIGS. 37 and 38 depict an accessory tissue displacement instrument according to another variation that displaces tissue upon changing from a first position to a second position.
Figure 38:
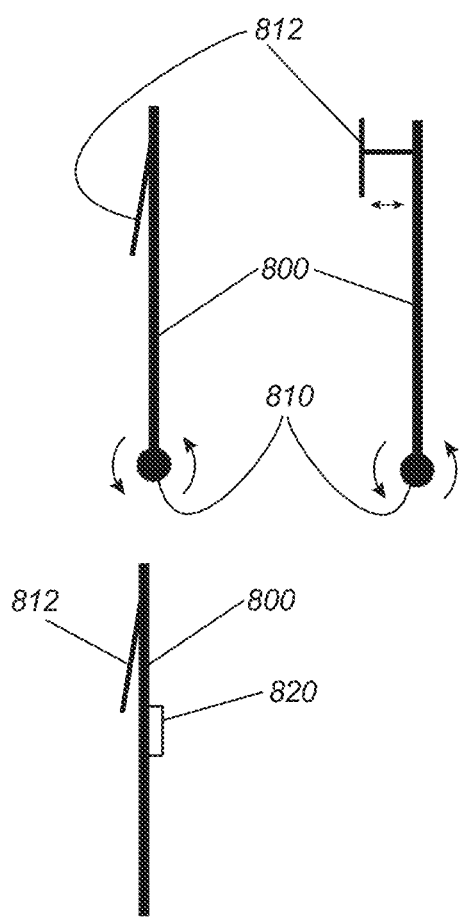

As shown in FIGS. 37 and 38, some variations of a device include a tissue displacement instrument with an expandable or deployable head (812) at one end of an elongate shaft (800) that, when deployed by an activation mechanism such as a switch, knob, button, inflation pump, or other suitable mechanism placed either at a second end of an elongate shaft (810) or along the body of an elongate shaft (820), changes from a first to a second position such that tissue is at least temporarily displaced.

Figure 39:
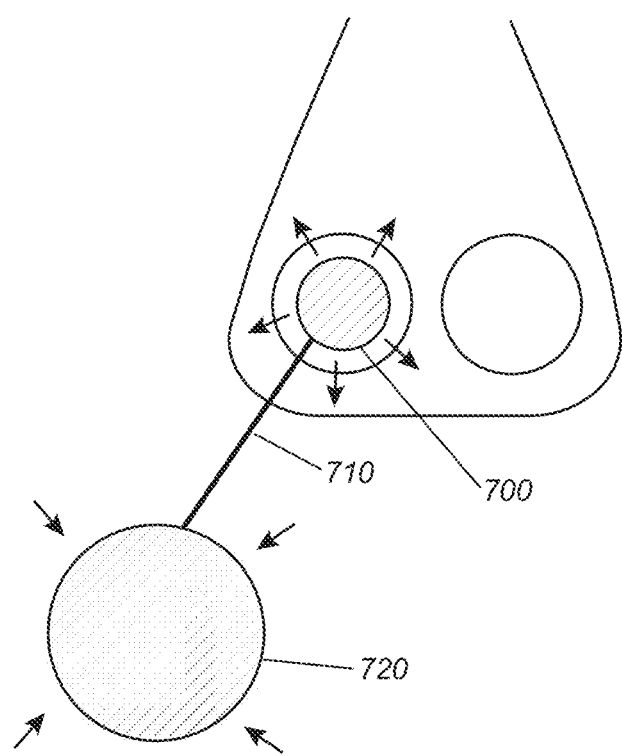
FIG. 39 depicts another exemplary tissue displacement instrument including an expandable element and an expansion activation element.

As shown in FIG. 39, some variations of a tissue displacement instrument include an internal balloon or expandable element (700) connected by a tube or elongated shaft (710) to an external expansion activation element (720).

Figure 40:
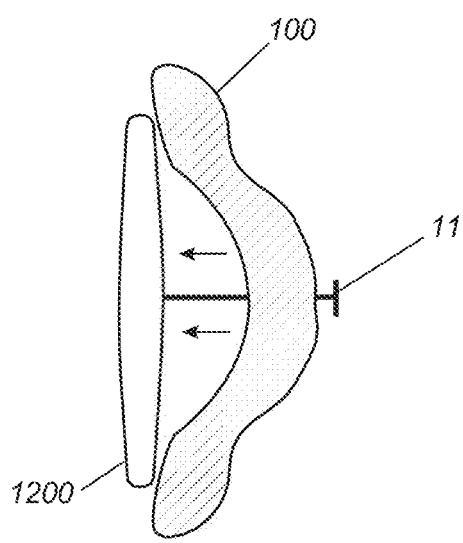
FIG. 40 depicts an exemplary tissue retention element for applying a force to tissue and holding the tissue in an altered shape.

As shown in FIG. 40, some variations of a device include a tissue retention element designed to hold a tissue into an altered shape (1000). This tissue retention element may also be known as a splint or stent. In some variations, this tissue retention element may be designed to straighten a deviated nasal septal cartilage (100). This tissue retention element may be placed above or below the mucosa. It may be placed on the concave or convex side of a deviation. It may include one or more tissue engagement features (11) that allow the tissue retention element to apply a force or remain connected to a tissue. The tissue retention element may be absorbable or nonabsorbable.

Figure 41:
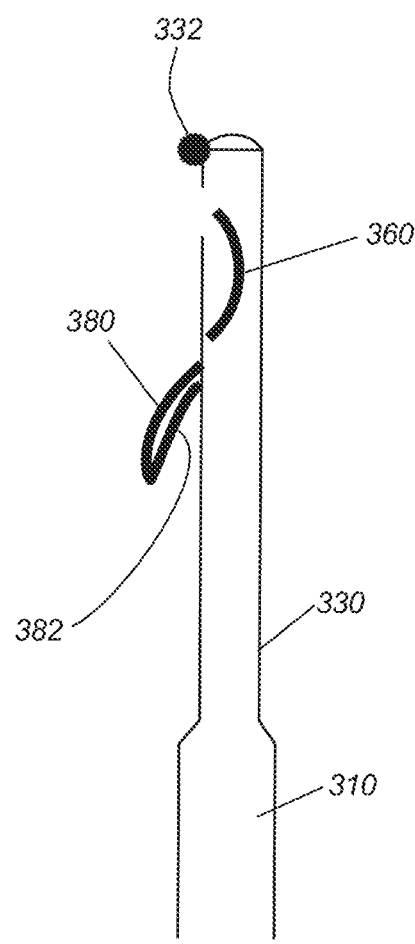
FIG. 41 depicts yet another exemplary delivery device including a tissue separation element.

As shown in FIG. 41, some variations of a delivery device include a tissue separation element (332) that allow the distal end of a delivery device to traverse within a tissue plane.

Figure 42:
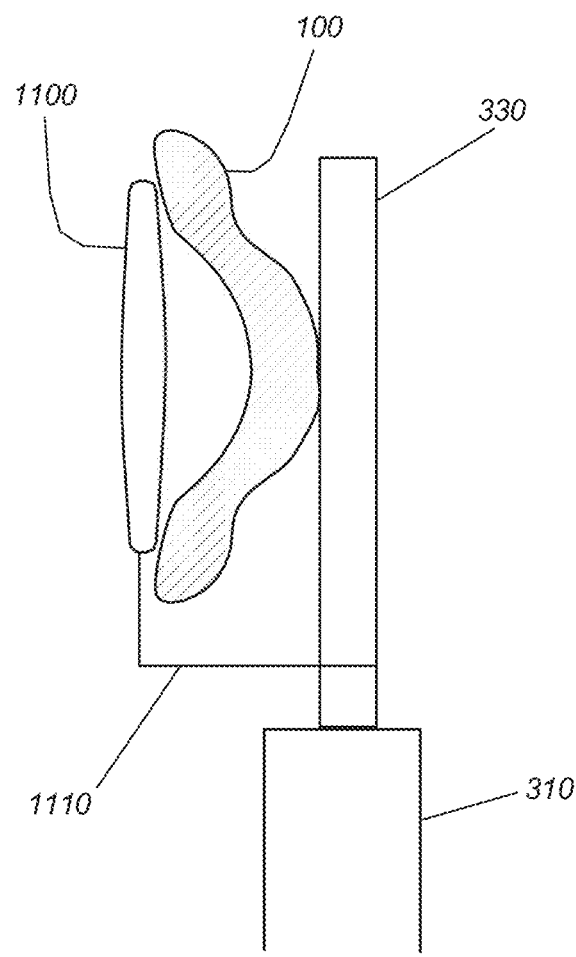
FIG. 42 depicts a further exemplary delivery device including an alignment feature for holding a tissue retention element in a position relative to the delivery device.

As shown in FIG. 42, some variations of a delivery device include an alignment feature (1110) that connects to either the elongate shaft (330) or body (310) of a delivery device such that it holds a tissue retention element in a position relative to the delivery device.

Methods

Methods for manipulating a tissue in a subject are also described herein. The methods may generally include securing a tension element to the tissue, where the tension element comprises an elongate body having a proximal end and a distal end, and a distal anchor at the tension element distal end. In some variations, the distal end of the tension element may be directed through the tissue with an anchor delivery element. The distal anchor may include an anchor body and a pivot point, and an insertion configuration and a deployed configuration. After securing the tension element to tissue, a force may be applied to the elongate body to swivel the distal anchor at the pivot point from the insertion configuration to the deployed configuration. The force appropriate to manipulate the tissue may then be adjusted by adjusting the tension of the tension element.

The proximal and distal ends of the elongate body of the tension element may be secured to the same tissue. Alternatively, the proximal and distal ends of the elongate body may be secured to different tissues. The tissue may be a nasal tissue, a throat tissue, or an ear tissue. Exemplary nasal tissues include without limitation, nasal septal cartilage, lateral nasal cartilage, major alar cartilage, minor alar cartilage, alar fibrofatty tissue, nasal bone, or a nasal turbinate. Exemplary throat tissues include without limitation, the uvula, soft palate, and tonsils. Non-limiting examples of ear tissues include cartilage of the helix, anti-helix, tragus, anti-tragus, superior crus, fossa triangularis, concha, and connective tissue of the earlobe.

The methods described herein may be used to treat various conditions and manipulate various tissues. For example, the manipulation of tissue by the tension elements may be used to treat nasal septal deviation, lateral nasal valve collapse, and other causes of nasal airway obstruction. Additionally, the manipulation of tissue may be used to medialize a middle turbinate, compresses or lateralize the inferior turbinate, or reapproximate nasal mucosa. Furthermore, the manipulation of tissue by the tension elements may alter the shape of various tissues. For example, the shape of a nasal tissue, a throat tissue, or an ear tissue may be altered. When the tissue is a nasal tissue, the tissue may include lateral cartilage, alar cartilage, columella, or a combination thereof. Additionally, the manipulation of tissue may be used to increase the stiffness or rigidity of a nasal tissue, a throat tissue, or an ear tissue. In some variations, the tension elements may be employed in minimally invasive face lift procedures.

Figure 68A:
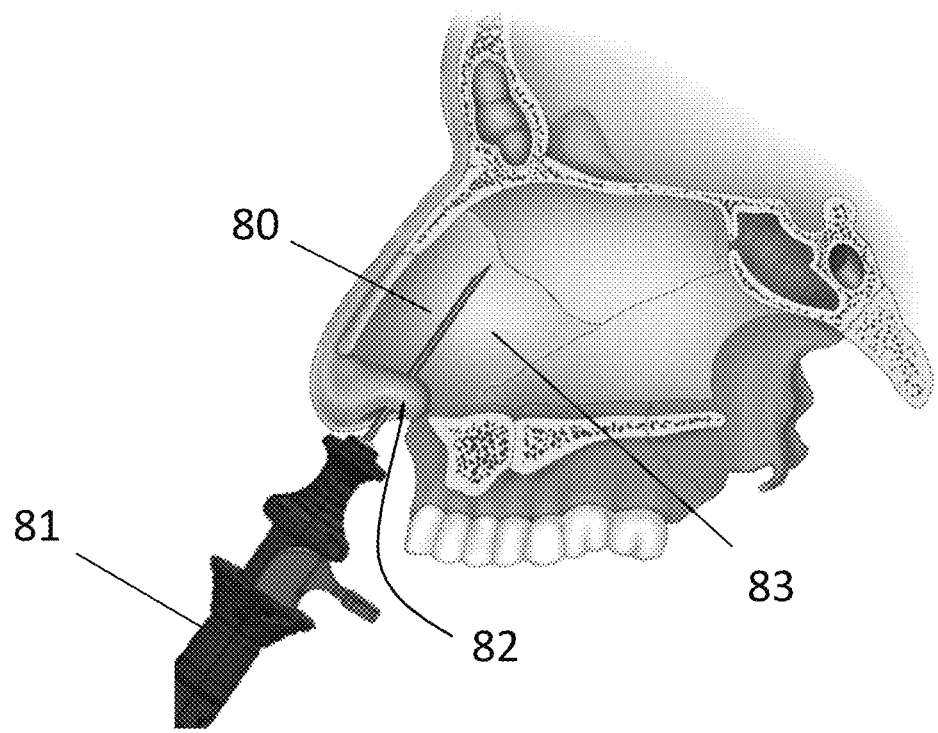
FIGS. 68A-68E depict an exemplary method of shaping a nasal septum using a tension element.
Figure 68B:
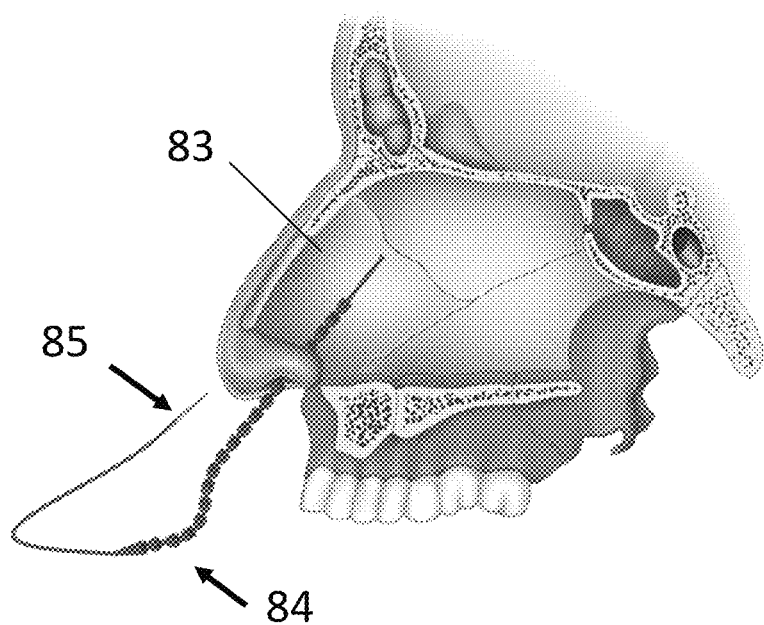
Figure 68C:
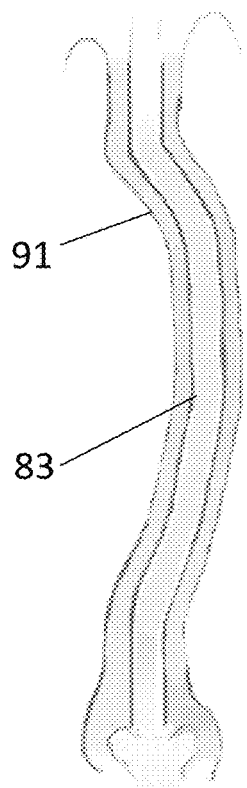
Figure 68D:
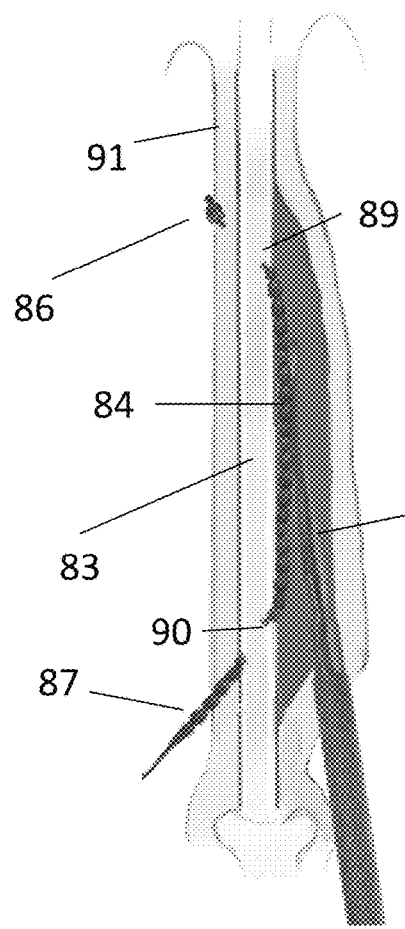
Figure 68E:
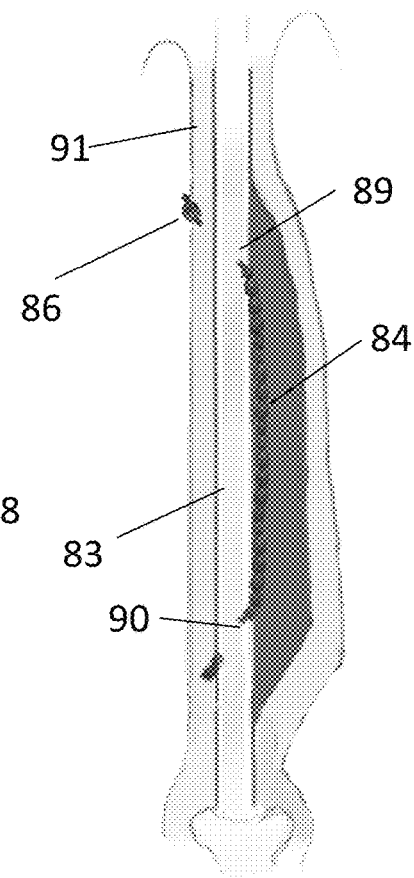

The methods may be used to shape the nasal septum, as shown in FIGS. 68A to 68E. A deviated nasal septum (83) is illustrated in FIG. 68C. Referring to FIGS. 68A to 68E, the method for shaping the deviated nasal septum (83) may include inserting a cannula (80) of a delivery device (81) into a nostril (82) and through the nasal septum (83) at a first location (89), securing a distal anchor (86) into the nasal cartilage (91), and deploying a tension element (84) from the delivery cannula (80). The proximal end (87) of the tension element (84) may then be passed through the nasal septum (83) at a second location (90). A force may be applied to the proximal end (87) of the tension element (84), which may create a medial force against the deviated nasal septum (83) to shape the tissue by straightening the tissue, as shown in FIG. 68D. Additional medial force may be applied by a surgeon using an instrument (88) to straighten the nasal septum (83). Once the desired amount of shaping is achieved, the force on the tension element (84) may be held by securing the proximal end (87) of the tension element (84) to the nasal septum (83) or nasal cartilage (91) near the second location (90).

In one variation, the methods for shaping or reshaping one or more nasal tissues in a subject may include advancing a delivery device through the one or more nasal tissues, where the delivery device may comprise an elongate tension element preloaded therein, and advancing the anchor delivery element from the delivery device through the one or more nasal tissues with a deployed force that is greater than an applied force by a user. After reaching a target area of the one or more nasal tissues, the tension element may be deployed from an anchor delivery element and into the target area. The ratio of the deployed force to the applied force may range from about 2:1 to about 4:1, including all values and sub-ranges therein.

When a deviated nasal septum is to be treated, the delivery device may be advanced by inserting a cannula of the delivery device through an access site in submucosal tissue on a first side of the nasal septum and through the nasal septum to a second side of the nasal septum. In some instances, the delivery device cannula may access a location anterior to the deviation and create a submucosal tunnel beneath the deviation. A distal anchor of the preloaded tension element may then be secured into nasal cartilage on the second side of the nasal septum (e.g., posterior to the deviation), where the distal anchor comprises a pivot point and has an insertion configuration and a deployed configuration. The method may include securing the distal anchor by applying a force to the elongate tension element to swivel the distal anchor at the pivot point from the insertion configuration to the deployed configuration.

Figure 91:
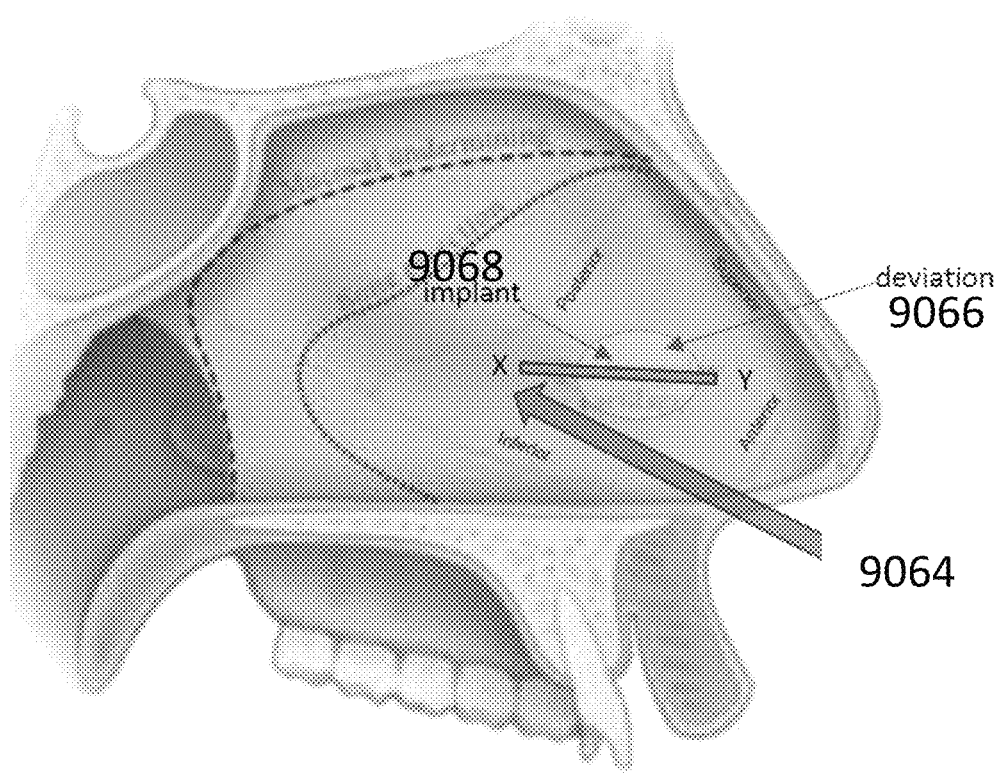
FIG. 91 depicts another exemplary method for placing a tension element to reshape a deviated nasal septum.

In some variations, the method may further include passing a proximal end of the elongate tension element back through the access site in submucosal tissue to the second side of the nasal septum, tensioning the elongate tension element to a tensioned state, and securing the proximal end of the elongate tension element in its tensioned state to tissue on the second side of the nasal septum. For example, referring to FIG. 91, a submucosal tunnel (9064) may be created with a delivery device cannula (not shown) below deviation (9066) for placement of a distal anchor (X) and a proximal anchor (Y) of a tension element (9068) to reshape the deviated nasal septum. The tension element in its tensioned state may apply a force ranging from about 1.0 Newton to about 70 Newtons (including all values and sub-ranges therein) to the deviated nasal septal tissues.

Figure 57A:
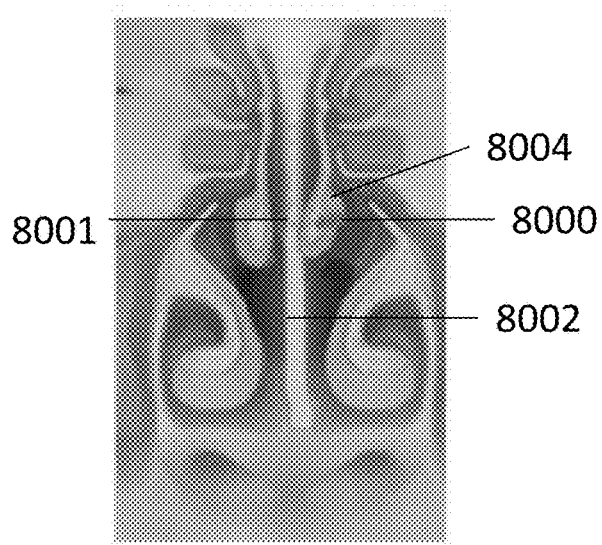
FIGS. 57A-57C depict exemplary methods for medializing the middle turbinate.
Figure 57B:
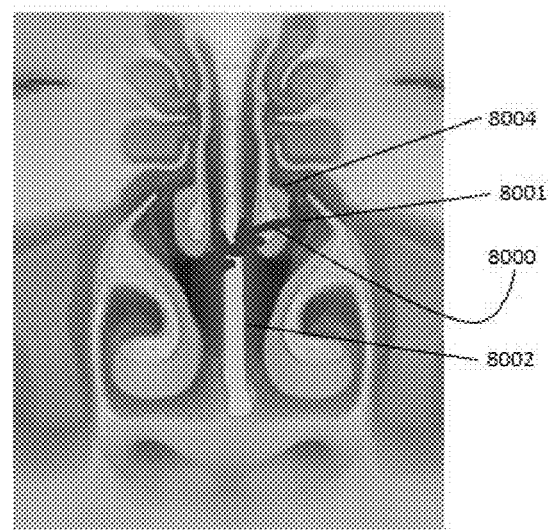
Figure 57C:
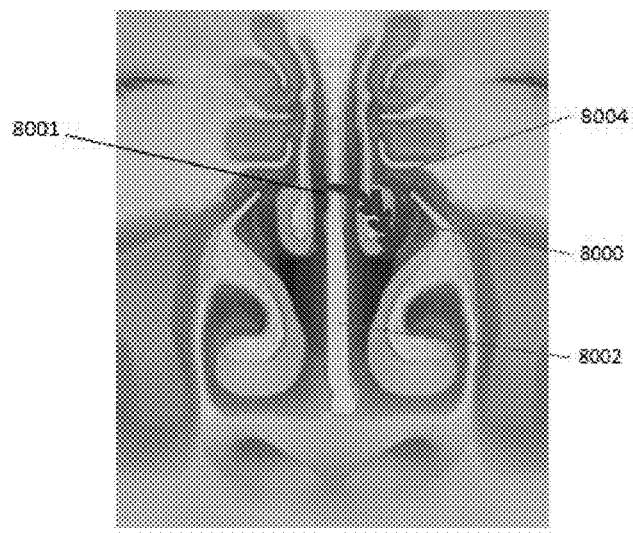

As shown in FIGS. 57A to 57C, the devices described herein may be used to medialize the middle turbinate. Referring to FIG. 57A, the method may include inserting a distal anchor (8001) of a tension element (8000) into nasal septal cartilage (8002), wrapping the tension element around the middle turbinate (8004), applying a force to the tension element to pull the middle turbinate (8004) medially toward the nasal septal cartilage (8002), and maintaining the medial position of the middle turbinate by securing the proximal end of the tension element (8000) to the nasal septal cartilage (8002). Securing the tension element proximal end may be accomplished by any suitable method. In one variation, suturing the proximal end to the nasal septal cartilage secures the tension element such that it maintains the force needed to medialize the middle turbinate. Alternatively, and as shown in FIG. 57B, the method for medializing the middle turbinate may involve inserting a distal anchor (8001) of a tension element (8000) into a middle turbinate (8004), applying a force to the tension element (8000) to pull the middle turbinate (8004) medially toward the nasal septal cartilage (8002), and maintaining the medial position of the middle turbinate (8004) by securing the proximal end of the tension element (8000) to the nasal septal cartilage (8002). Securing the tension element proximal end may be accomplished by any suitable method. As previously mentioned, suturing the proximal end to the nasal septal cartilage secures the tension element such that it maintains the force needed to medialize the middle turbinate. In yet a further variation, as shown in FIG. 57C, the method for medializing the middle turbinate may include inserting a distal anchor (8001) of a tension element (8000) into nasal septal cartilage (8002), passing the proximal end of the tension element (8000) through the middle turbinate (8004), and securing the middle turbinate (8004) in a medialized position by securing the proximal end of the tension element (8000) to the middle turbinate (8004).

Figure 58A:
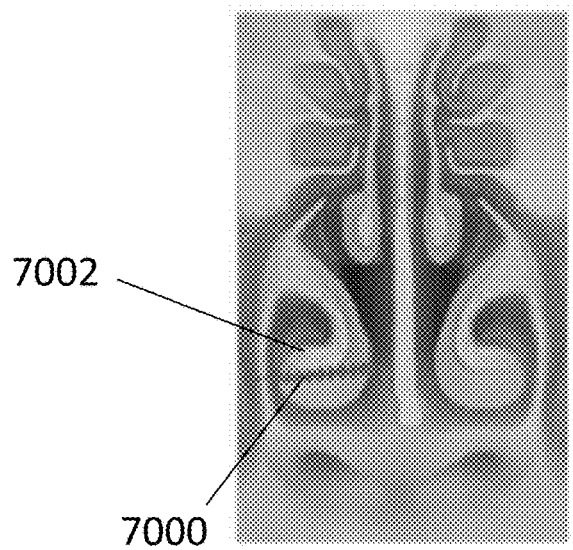
FIGS. 58A-58D depict exemplary methods for treating inferior turbinate hypertrophy.
Figure 58B:
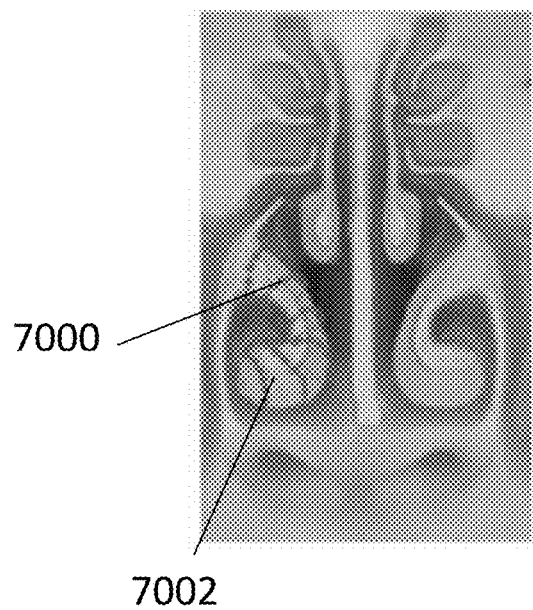
Figure 58C:
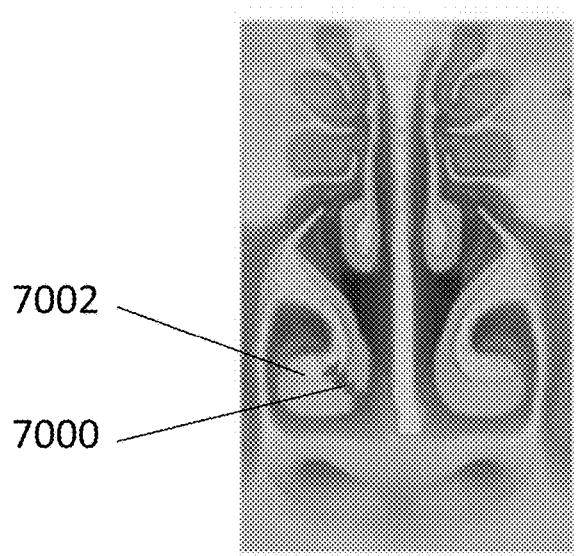
Figure 58D:
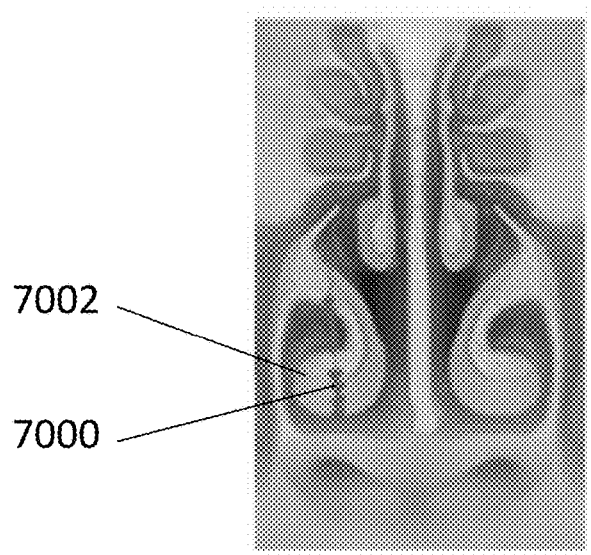

As shown in FIGS. 58A-58D, methods for treating inferior turbinate hypertrophy may include wrapping a tension element (7000) around the inferior turbinate (7002). A single turn may be used to wrap the tension element (7000) around the outer edges of the inferior turbinate (7002) to reduce its diameter (FIG. 58A). In another variation, multiple turns may be used to wrap a tension element around the entire inferior turbinate to compress and reduce the caliber of the inferior turbinate (FIG. 58B). Alternatively, a single turn may be used to wrap the tension element (7000) so that it is mobilized laterally (FIG. 58C) or superiorly (FIG. 58D).

Figure 59A:
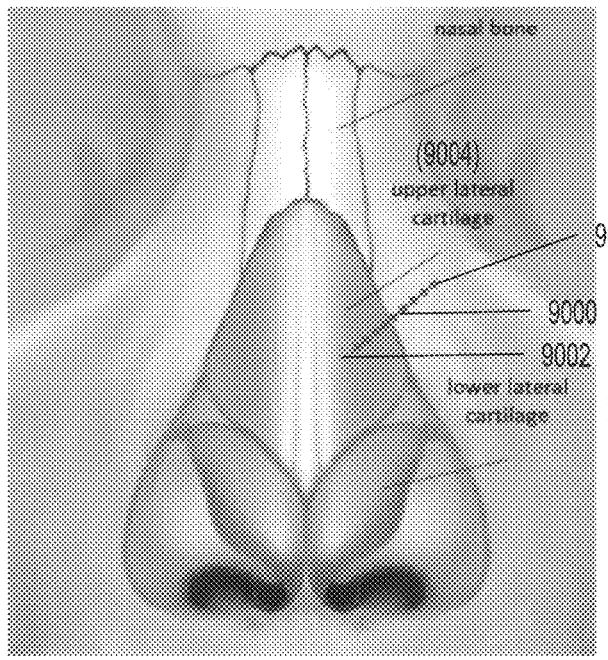
FIGS. 59A-59D depict exemplary methods for treating lateral nasal valve collapse.
Figure 59B:
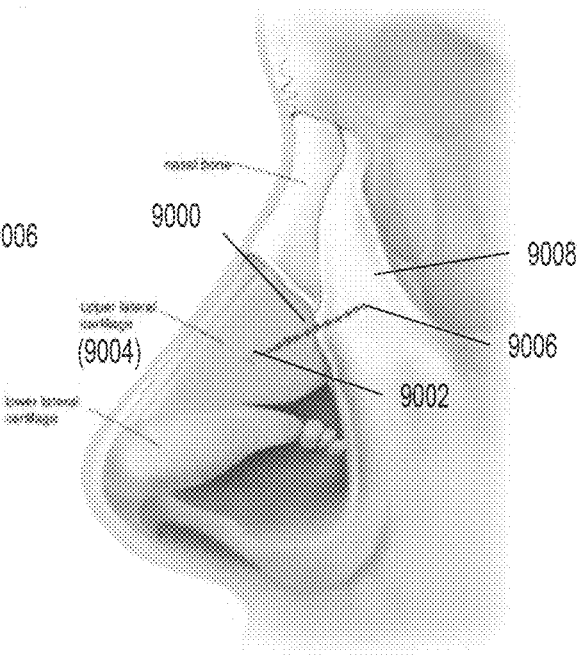
Figure 59C:
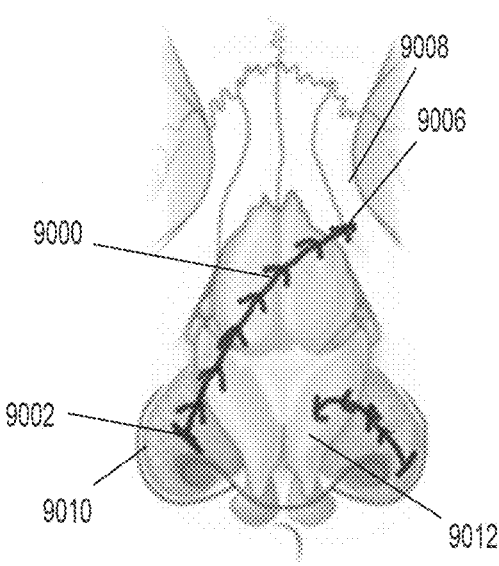
Figure 59D:
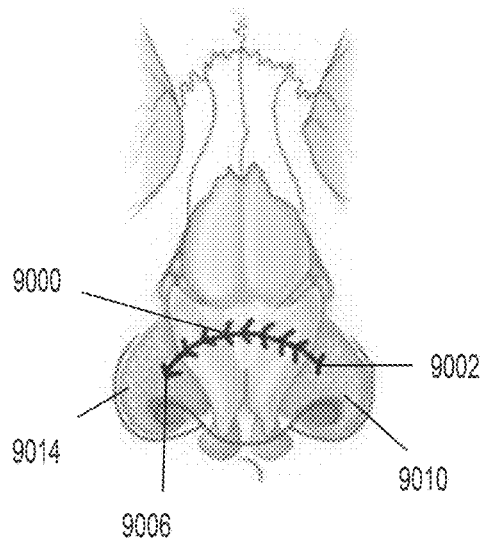

Lateral nasal valve collapse may also be treated with the tension elements described herein. As shown in FIGS. 59A-59D, a tension element (9000) may be anchored between two nasal tissues and a tension force applied therebetween to increase the patency of the nasal valve. For example, in FIGS. 59A and 59B, the distal end (9002) of tension element (9000) may be anchored in the upper lateral cartilage (9004) and the proximal end (9006) of the tension element (9000) secured in the maxillary bone (9008). As shown in FIG. 59C, the distal end (9002) of tension element (9000) may be anchored in fibrofatty tissue (9010), and the proximal end (9006) secured in the maxillary bone (9008) or a lower lateral cartilage (9012). Alternatively, as shown in FIG. 59D, the distal end (9002) of a tension element (9000) may be anchored in fibrofatty tissue (9010) and the proximal end (9006) secured to fibrofatty tissue on the opposing side (9014) of the nose.

Figure 60A:
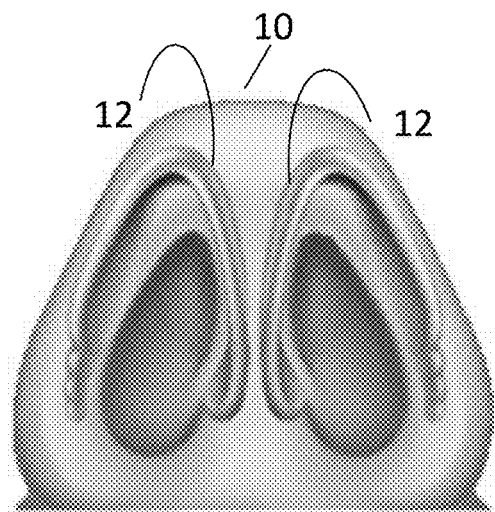
FIGS. 60A-60C depict an exemplary method for nasal tip reshaping.
Figure 60B:
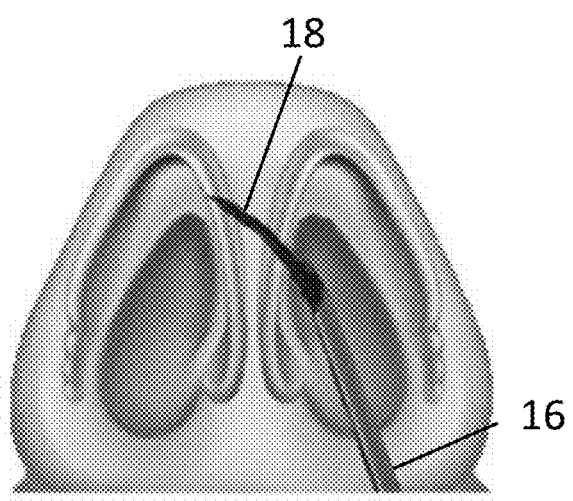
Figure 60C:
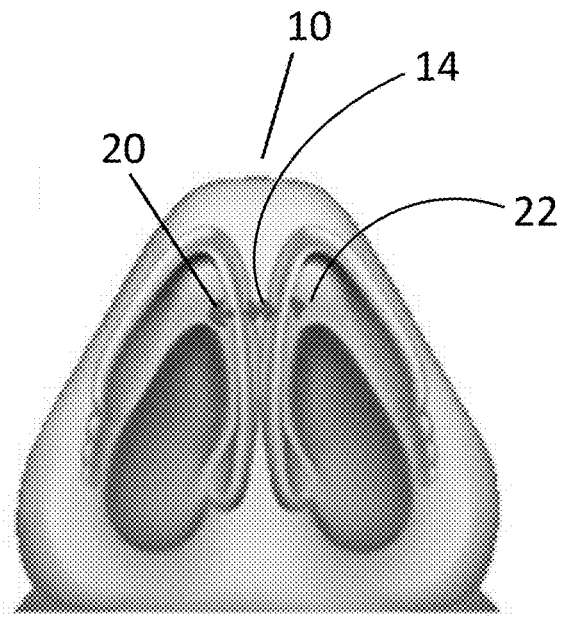

Nasal tip reshaping may further be accomplished with the tension elements described herein. As shown in FIGS. 60A-60C, the shape of nasal tip (10) may be altered by pulling lateral cartilages (12) medially. To this end, a tension element (14) coupled to an anchor delivery element (18) may be deployed from a delivery cannula (16) such that the distal anchor (20) of the tension element (14) is secured to one nasal cartilage (12) and the proximal end (22) of the tension element (14) is secured to the other nasal cartilage (12). A tension force provided between the distal anchor and the tension element proximal end may draw the lateral cartilages together to thereby alter the shape of the nasal tip (10).

Figure 61:
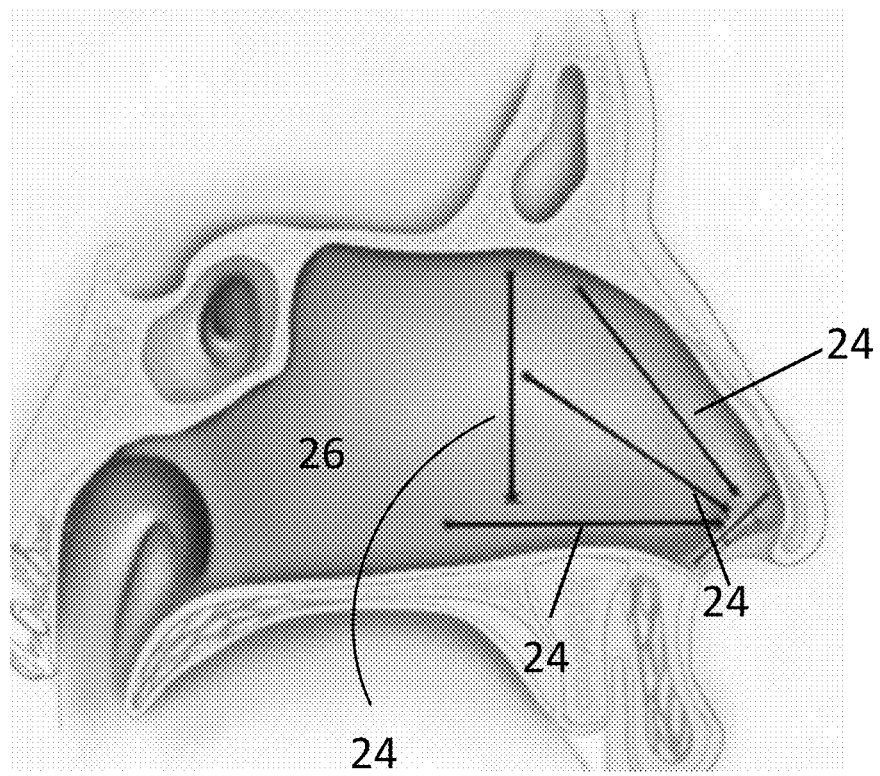
FIG. 61 depicts an exemplary method for tacking nasal mucosa to prevent nasal septal hematoma formation.

In some variations, the method may include reapproximating nasal mucosa to prevent the formation of nasal hematoma, for example, after nasal septoplasty. Referring to FIG. 61, a tension element (24) may be placed on the surface of the nasal mucosa (26) in one or more locations shown in the figure to tack down the mucosa and prevent any negative spaces from forming that could fill with blood.

Figure 62C:
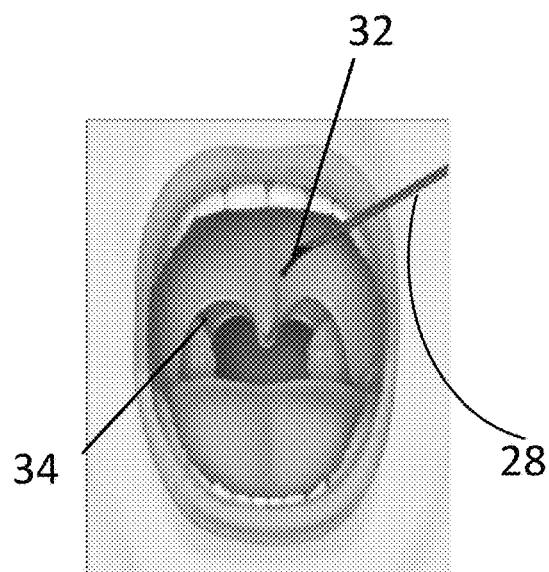
Figure 62C:
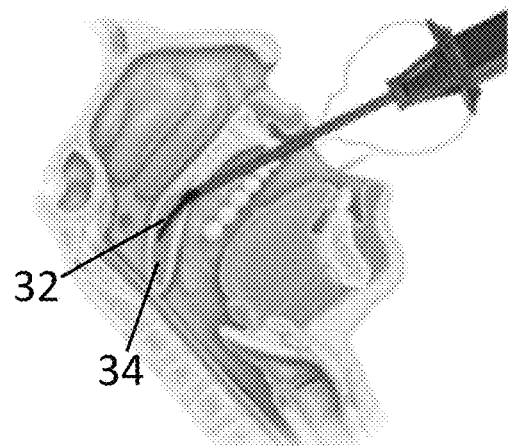
Figure 62C:
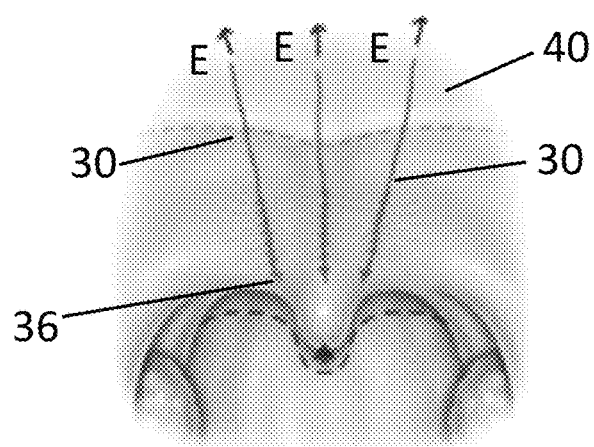

In other variations, the method may include placing one or more tension elements in throat tissue to treat obstructive sleep apnea. As shown in FIGS. 62A-62C, the method may include advancing a delivery cannula (28) carrying a tension element (30) coupled to an anchor delivery element (32) to the throat of a subject, inserting the anchor delivery element (32) into the uvula (34), setting the distal anchor (36) of the tension element (30) into tissue of the uvula, applying a tension force on the tension element (30) and distal anchor (36) in the direction of arrow E to lift the uvula, and securing the proximal end (38) of the tension element (30) in tissue of the soft palate (40) to maintain the tension force on the uvula (34). One or a plurality of tension elements may be employed to lift the uvula and treat obstructive sleep apnea.

Figure 63A:
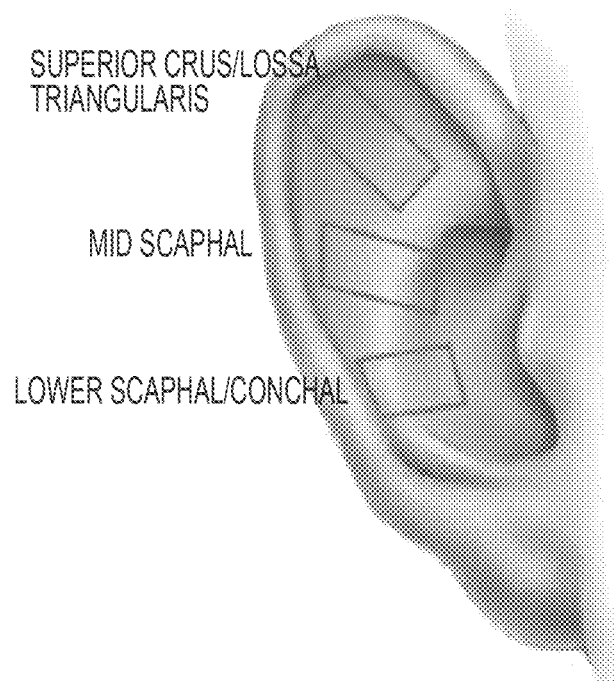
FIGS. 63A and 63B depict exemplary areas of the ear for placement of a tension element to reshape the ear.
Figure 63B:
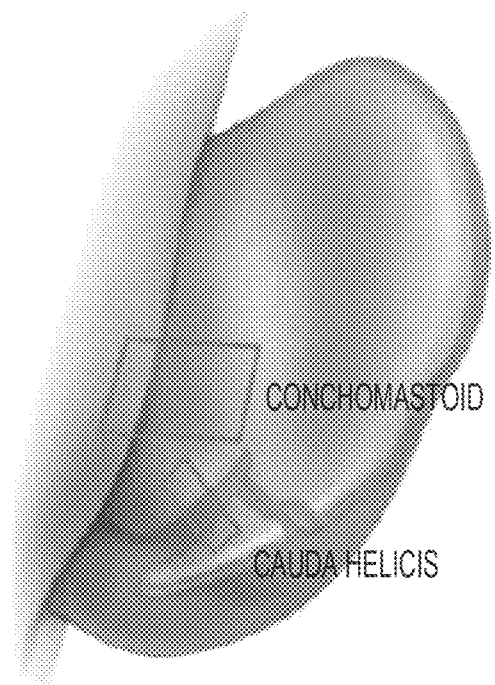

The reshaping of ear tissues may also be accomplished with the devices described herein. In some variations, reshaping is used to treat a poorly defined antihelix, for example, by creating or increasing the antihelical fold. In other cases, reshaping may be used to correct enlarged conchal cartilage. As shown in FIGS. 63A and 63B, the method to more clearly define the antihelix may include placing a tension element in one or more of the locations shown in the figures. For example, the tension element may be placed at the superior crus or fossa triangularis, the midportion of the scapha, the lower portion of the scapha or concha, or the conchomastoid and cauda helicis regions of the posterior ear.

The force applied to manipulate or shape a tissue may range from about 4.0 Newtons to about 70 Newtons, including all values and sub-ranges therein. The force may be generated by pulling on the free proximal end of the tension element after the distal anchor has been fixed to the target tissue. For example, the tension force may be about 4.0 Newtons, about 5.0 Newtons, about 10 Newtons, about 15 Newtons, about 20 Newtons, about 25 Newtons, about 30 Newtons, about 35 Newtons, about 40 Newtons, about 45 Newtons, about 50 Newtons, about 55 Newtons, about 60 Newtons, about 65 Newtons, or about 70 Newtons. Tensile strength of the tension element may range from about 100 Mpa to about 300 Mpa, including all values and sub-ranges therein. For example, the tensile strength may be about 100 Mpa, about 110 Mpa, about 120 Mpa, about 130 Mpa, about 140 Mpa, about 150 Mpa, about 155 Mpa, about 160 Mpa, about 165 Mpa, about 170 Mpa, about 175 Mpa, about 180 Mpa, about 185 Mpa, about 190 Mpa, about 195 Mpa, about 200 Mpa, about 210 Mpa, about 220 Mpa, about 230 Mpa, about 240 Mpa, about 250 Mpa, about 260 Mpa, about 270 Mpa, about 280 Mpa, about 290 Mpa, or about 300 Mpa. In some instances, the tensile strength of the tension element may be at least about 150 Mpa. In other instances, the tensile strength of the tension element may be at least about 300 Mpa. The applied force may decrease over time as the tension element biodegrades. In general, the tension element biodegrades over a period of about one months to about twelve months. For example, the tension element may biodegrade over a period of at least about one month, about two months, about three months, about four months, about five months, about six months, about seven months, about eight months, about nine months, about ten months, about eleven months, or about twelve months. In one variation, the tension element may degrade over a period ranging from about four months to about nine months.

Other methods for altering the shape of tissue structures of a subject are also described herein. The methods generally include deploying a shaping element or tension element into tissue, and manipulating the shaping element to apply a force to the tissue such that is alters the shape of the nasal tissue. The force may be a tensioning force. Various body tissues may be shaped using the tensioning force. Exemplary tissues include without limitation, nasal septal cartilage, lateral nasal cartilage, major or minor alar cartilages, alar fibrofatty tissue, nasal bone, and nasal turbinates.

The methods described herein may be used for treatment of nasal airway obstruction; treatment of a deviated nasal septum; straightening of a nasal septum; treatment of a thickened, deformed, or dislocated nasal septum; repair of nasal septal fracture; alteration of the shape of the nasal septum; treatment of nasal septal spurs or nasal bone spurs; alteration of the shape of the internal or external shape of the nose; treatment or alteration of structural deformity of a nasal cartilage other than the nasal septum; treatment of internal nasal valve collapse; or treatment of turbinate hypertrophy. The method may also be employed to treat or alleviate sleep apnea, nasal snoring, or may be configured for any other suitable alteration of nasal tissue or any combination of tissues. In other variations, the methods described herein may be used to buttress or aid in approximating broken nose fragments.

When the shape of the nasal septal cartilage is to be altered, for example, to correct a deviated nasal septum, the method may include passing a suture, barbed suture, or shaping element, through the nasal septum, tightening the suture until the septum is straightened, and trimming the excess suture. In some variations, the method for adjusting the shape of a deviated septum may include applying between about 4.0 Newtons and about 70 Newtons of force to the nasal septum using the shaping element. In other variations, the method may include applying between about 12 Newtons and about 25 Newtons of force to the nasal septum using the shaping element.

In some variations, the method may employ a device that includes an elongate member comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

Manipulating the shaping element may include manipulating a second end of the shaping element to apply a force to the tissue. In some variations, the second end of the shaping element may be secured to tissue adjacent the nasal airway after applying the force. Securing the second end may include directing the second end through tissue at a location spaced apart from the first end. In one variation, the first end may be secured to the tissue on one side of a deviated septum, and the second end is secured to the tissue on an opposite side of the deviated septum, and a force applied to alter the shape of the deviated septum. In another variation, the first end is secured to tissue distal to a deviated septum, wherein the second end may be secured to tissue proximal to the deviated septum, and a force applied to alter the shape of the deviated septum. The force applied by the shaping element is generally a tensioning force.

Alternatively, manipulating the shaping element may include engaging an intermediate region of the shaping element with tissue at a second location spaced apart from a first location to which the first end is secured, and applying a force to the shaping element between the first and second locations to alter the shape of the tissue between the first and second locations. One or more elements at the intermediate region may be engaged with the tissue at the second location to maintain the tension. Furthermore, engaging an intermediate region may include directing a second end of the shaping element through the tissue at the second location, and pulling the second end until the intermediate region engages the tissue at the second location. The intermediate region may include a plurality of migration prevention elements spaced apart from one another. Here the second end may be pulled until at least one of the migration elements passes through the tissue at the second location, thereby preventing the intermediate region from passing back through the tissue at the second location.

In some variations, manipulating the shaping element may further include adjusting a location of a securing element on the intermediate region with the tissue at the second location to maintain the tension. In other variations, the method further includes separating the second end of the shaping element from the intermediate region, for example, by cutting the shaping element adjacent the intermediate region to remove excess material from the shaping element.

In another variation, a method is provided for altering the shape of nasal tissue of a subject that includes inserting a distal end of a delivery device into a nasal airway of the subject, deploying a first end of a shaping element from the distal end into the nasal airway; securing the first end of the shaping element to tissue adjacent the nasal airway, manipulating the shaping element to alter a shape of the tissue, and removing the delivery device such that the shaping element at least temporarily maintains the altered shape of the tissue.

In a further variation, the method for altering the shape of nasal tissue of a subject includes deploying a first end of a shaping element into a nasal airway of the subject, securing the first end of the shaping element to tissue at a first location adjacent the nasal airway, manipulating the shaping element to alter a shape of the tissue, and securing the shaping element relative to tissue at a second location to maintain the altered shape of the tissue. Securing the shaping element at the second location may include securing a second end of the shaping element at the second location. In one variation, securing the shaping element at the second location includes securing one or more migration prevention elements on the shaping element at the second location. In another variation, the method further includes removing excess material of the shaping element once the one or more migration prevention elements are secured at the second location. In a further variation, the second location may be located closer to the nasal ostium than the first location.

Some methods for altering the shape of nasal tissue of a subject include introducing an anchor into a nasal airway of the subject, securing the anchor at a first location to a nasal septum of the subject, introducing a first end of a shaping element into a nasal airway of the subject, securing the first end of the shaping element to the anchor; manipulating the shaping element to alter a shape of the tissue, and securing the shaping element relative to tissue at a second location to maintain the altered shape of the tissue. The anchor may be introduced into a first nasal airway of the subject and secured by directing the anchor through the nasal septum at partially into a second nasal airway of the subject, and the first end of the shaping element may be introduced into the second nasal airway and secured to a portion of the anchor extending into the second nasal airway. In one variation, the first end of the shaping element is introduced into the nasal airway submucosally before securing the first end to the anchor.

Other methods for altering the shape of nasal tissue of a subject may include inserting a distal end of a delivery device into a nasal airway of the subject, deploying a first end of a shaping element from the distal end into the nasal airway, securing the first end of the shaping element to tissue at a first location adjacent the nasal airway, and removing the delivery device such that the shaping element extends from nasal airway. A needle coupled to a second end of the shaping element may then be inserted into the nasal airway, and the shaping element manipulated to alter a shape of the tissue. Securing the second end at a second location adjacent the nasal airway may temporarily maintain the altered shape of the tissue.

In some methods, shaping of nasal tissue may be accomplished using a shaping element or a tension element fitted with an energy delivery element. For example, one or more permanent or temporary electrodes, heating elements, or other energy delivery mechanism that allows the tension element to deliver energy to the nasal tissue may be included with the shaping element. The energy delivery mechanism may be used to augment reshaping or remodeling of the nasal tissue by application of heat, electric current, or any suitable form of energy. In some variations, the energy delivery mechanism may be removed after energy is applied. In some variations, the energy delivery mechanism may be implanted with the tension element. In some variations, the energy delivery mechanism may be bioabsorbable or biodegradable. In some variations, the energy delivery mechanism is attached directly to the tension element. In some variations, the energy delivery mechanism is situated adjacent to the tension element.

The tension element may also be used to alter the shape of tissues other than nasal tissue. In one variation, the tension element may be used to shape cardiac tissues. For example, the leaflets of a cardiac valve (e.g., a mitral valve, aortic valve, tricuspid valve, pulmonary valve) may be approximated to treat valve insufficiency due to leaflet prolapse, leaflet calcification, cardiomyopathy, or a congenital heart defect. Cardiac hypertrophy due congestive heart failure may also be prevented or minimized by wrapping the tension element around the heart to constrict enlargement of one or more of the cardiac chambers (e.g., right atrium, right ventricle, left atrium, left ventricle).

In other variations, the tension element may be used to assist with vascular closures (e.g., venous access closure) or to shift the location of an enlarged prostate to help maintain patency of the urethra. When used in orthopedic procedures, the shaping may employed in tendon repair or ligament repair (e.g., anterior cruciate ligament, posterior cruciate ligament, medial collateral ligament), meniscus repair, or bone repair. The shaping element may also be used for wound closure as an alternative to sutures, staples, or glue, or to approximate tissue layers for hernia repair. In further variations, the tension element may be used for shunt, port, or catheter stabilization, or as an alternative to barbed sutures during aesthetic procedures. In some variations, the tension element may be used in animals for the same purposes.

Fluids may also be delivered before, during, or after placement of the tension element using a fluid delivery mechanism. The fluid may provide a therapeutic or physiologic effect. For example, the fluid may include a therapeutic agent, or a cold gas or liquid for the purposes of cryotherapy. Other therapies such as radiofrequency or thermal therapies may also be used in combination with delivery of the tension elements. In some instances the additional therapies may be employed to mechanically or chemically induce submucosal fibrosis after tension element placement to aid in locking the tension element in place and/or maintain the desired tissue correction.

Methods for making the tension elements are also described herein. In some variations, the tension element may be manufactured from a single material or a composite material comprised of multiple materials. In some variations, the tension element may be manufactured from a polymer (e.g., polydioxonone) configured as a rectangular ribbon or an ovalized ribbon, and then cutting the tension element from the ribbon. In some instances, drawing or pulling of the polymer (e.g., during extrusion of the polymer) may be performed to give the polymer a desired polymer chain orientation, e.g., an orientation of −30 degrees, −45 degrees, −60 degrees, +30 degrees, +45 degrees, or +60 degrees. Cutting may be accomplished using various techniques, such as, but not limited to, die (shear) cutting, water jet cutting, laser cutting, and/or cutting using an abrasive material (e.g., garnet particles, aluminum oxide). In other variations, the tension element may be formed integrally with the anchor delivery element by 3D printing. After 3D printing, the distal end of the anchor delivery element may be CNC machined and sharpened.

Other Exemplary Methods

As shown in FIG. 1, an exemplary method for altering the shape of a nasal tissue (100) includes deploying at least one tensioning or other shaping element (200) into the nasal airway, adjacent to a nasal tissue, and securing the tension element (200), such that the nasal tissue at least temporarily maintains an altered shape. The tension element can also be known as a brace, suture, graft, buttress, implant, or supporting element. The method may utilize one tension element or multiple tension elements arranged in a parallel or non-parallel fashion. In some variations, securing the tension element may allow for the application of force to the nasal tissue that is configured to at least temporarily allow the nasal tissue to maintain an altered shape. In some variations, the force may be a tension force. In some variations, securing the tension element may involve fixing a portion of the tension element through the target nasal tissue or through another nasal tissue. In some variations, the tissue through which the tension element is secured is cartilage, bone, any semi-rigid tissue, or any combination thereof. The method may be configured to adjust the shape of a nasal tissue to a final state in one application or may be configured with an adjustable tension element that allows adjustments to the force or shape to be made over time. The method may also be configured to utilize tension elements deployed at varying time points to alter the shape of a nasal tissue sequentially.

In some variations, the method may involve applying an external force to alter the shape of the nasal tissue before or during deployment of the tensioning device. In some variations, application of external force may be accomplished by means of a force applying element such as a nasal speculum, spreader, suture passer, forceps, or other tool or device suitable for manipulating the nasal tissue. In some variations, the force may be applied transmucosally, transcutaneously, and/or extramucosally. In some variations, the method may involve applying an external force to alter the shape of the nasal tissue after initial deployment of the tension element but before final securing the tension element. In some variations, the method may involve applying an external force to alter the shape of the nasal tissue before or after deployment of the tension element.

In some variations, the method may be configured to be suitable for use in a medical clinic or office. In some variations, the method may be configured to be suitable for use in an otolaryngology clinic or office. In some variations, the method may be configured to be suitable for use in a surgical center or setting. In some variations, the method may be configured to include the use of an analgesic. In some variations, the method may be configured to include the use of anesthetic. In some variations, the method may be configured to include the use of supporting elements, which can also be known as splints. In some variations, the method may be configured to include elevating the nasal mucosa away from the target tissue by means of an instrument, balloon, or other method of mucosal elevation. In some variations, the method may be configured to include the use of a scope or other means of visualization. The methods described herein may be configured and/or adapted for one or more of treatment of nasal airway obstruction; treatment of a deviated nasal septum; straightening of a nasal septum; treatment of a thickened, deformed, or dislocated nasal septum; repair of nasal septal fracture; alteration of the shape of the nasal septum; treatment of nasal septal spurs or nasal bone spurs; alteration of the shape of the internal or external shape of the nose; treatment or alteration of structural deformity of a nasal cartilage other than the nasal septum; treatment of internal nasal valve collapse; or treatment of turbinate hypertrophy. The method can also be configured and/or adapted for sleep apnea, nasal snoring, or may be configured for any other suitable alteration of nasal tissue or any combination of tissues.

In some variations, a method for altering the shape of a nasal tissue may also include inserting a delivery device into the nasal airway, deploying at least one tension element (200), securing the tension element, and removing the device such that the nasal tissue at least temporarily maintains an altered shape. For example, the delivery device may be inserted into the nasal airway, inserted beneath the nasal mucosa, or positioned in any other configuration suitable for facilitating the placement or deployment of the tension element. In some variations, some or all of the delivery device may be disposable. In some variations, some or all of the delivery device may be reusable and may be configured to be suitable for sterilization.

Figure 2:
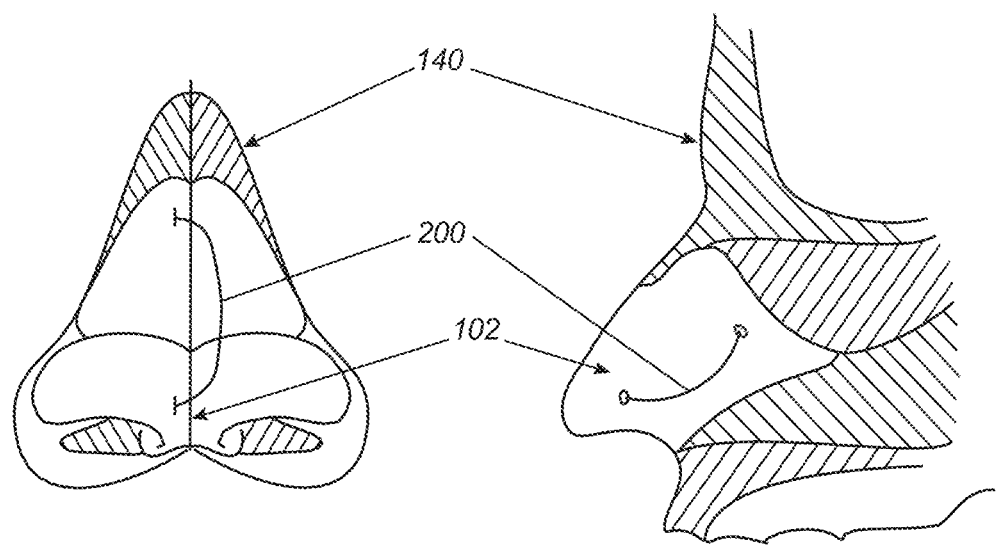
FIG. 2 depicts an exemplary method for shaping a nasal septal cartilage.

As shown in FIG. 2, a method for altering the shape of a nasal tissue may specifically be optimized for adjusting the shape of the nasal septal cartilage (102). The method may be configured to adjust the shape of a deviated septum of any kind, classification, or location, including, but not limited to, "C-shaped" deviations, "S-shaped" deviations, subluxation of septal cartilage, sagittal deviations, coronal deviations, deviations caused by bony deformation, cartilaginous deformation, ossified cartilage, dislocation of bone or cartilage, thickened or hypertrophied cartilage or bone, cartilaginous or bony spurs, trauma to bone or cartilage, or any other form of septal deviation or combination thereof. In some variations the method is used for correction of anterior caudal septal deviation. In some variations the method is used for altering the shape of the posterior septal cartilage. In some variations the method is used for correction of external nasal deformities involving the "L-strut," but may additionally or alternatively be used for any suitable applications, clinical, functional, cosmetic, or otherwise. In some variations, the tension element may be secured to or thorough cartilage. In some variations, the tension element may be secured to or through bone or any other suitable nasal tissue. In some variations the tension element may be placed on the convex side of the deviation. In some variations the tension element may be placed on the concave side of the deviation. In some variations where the method is configured for altering the shape of the nasal septal cartilage, the method may be configured as correction of a deviated nasal septum by means of passing suture or barbed suture through the nasal septum, tightening the suture until the septum is straightened, and trimming the excess suture. In some variations, the method configured for adjusting the shape of a deviated septum may be specifically optimized to provide between 4 and 40 Newtons of force. In some variations, the method may be further optimized to provide between 12 and 25 Newtons of force.

Figure 3:
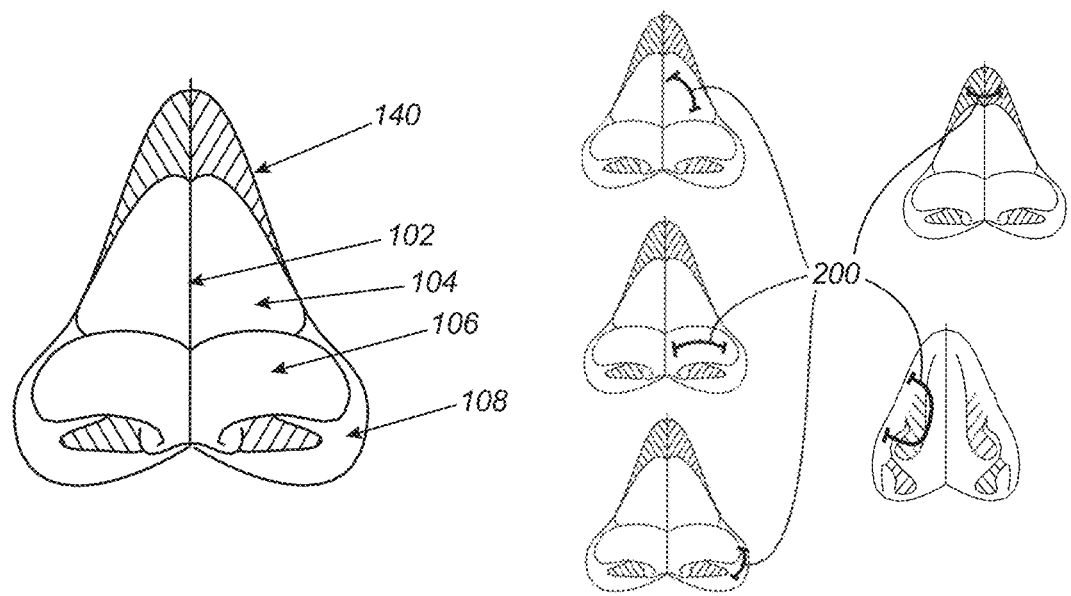
FIG. 3 depicts exemplary methods for shaping a lateral nasal cartilage, a major or minor alar cartilage, alar fibrofatty tissue, a nasal bone, and a nasal turbinate.

As shown in FIG. 3, a method for altering the shape of a nasal tissue may be specifically optimized for adjusting the shape of a nasal tissue other than the nasal septal cartilage (102). In some variations, the method may be configured to adjust the shape of the lateral nasal cartilage (104), the major or minor alar cartilage (106), the alar fibrofatty tissue (108), a nasal bone (140), a nasal turbinate (150), or any other suitable nasal tissue.

Figure 4:
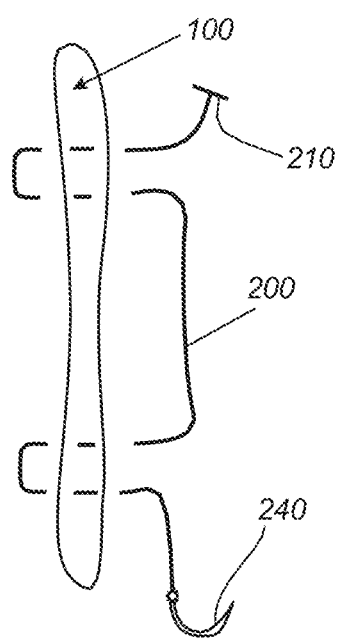
FIG. 4 depicts another exemplary tension element comprising a suture having a securing element at one end, and a needle at the other end.

As shown in FIG. 4, in some variations, the method may be configured to use suture or sutures as the tension element (200). In some variations, the tension element may be optionally configured as barbed suture or sutures. The suture may be of any diameter, size, shape, length, or width. In some variations, the sutures may be arranged in a pattern to sufficiently alter the shape of a nasal tissue. The method may be configured for any number of suture passes or patterns. The suture may include a securing element (210) designed to prevent migration or translocation of the suture through the nasal tissue. The configuration may include a series of at least one vertical or horizontal-mattress-like sutures. In some variations, the suture may be placed and secured submucosally, transmucosally, or transcutaneously. In some variations, the suture may be introduced via a needle (240) attached to at least one end of the suture. The method may be configured to use a needle or needles that are straight, curved, flat, or otherwise shaped. The method may be configured to use a needle or needles that are attachable or detachable from the suture. The method may be configured to utilize a kit or packaged set of instruments, tools, or suture materials for placing and tensioning suture to alter the shape of a nasal tissue.

Figure 5:
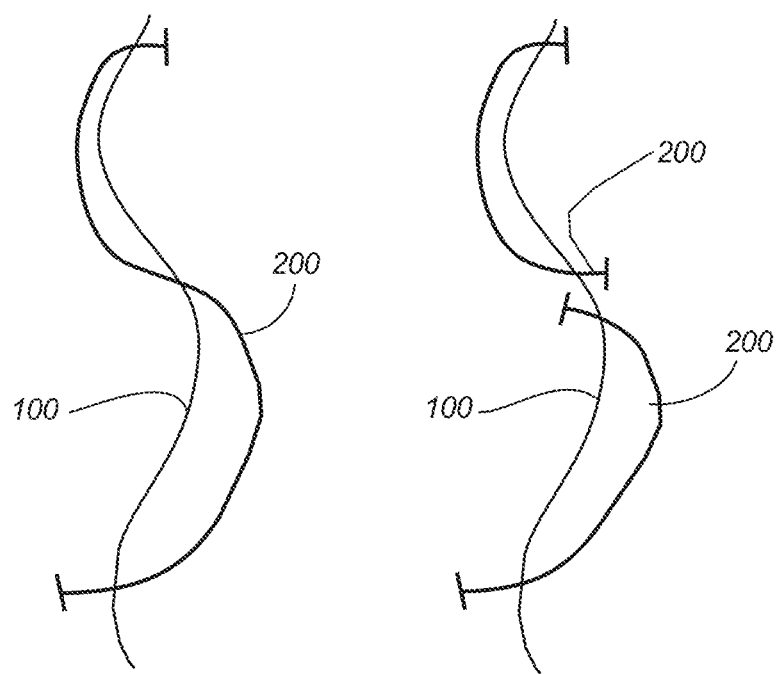
FIG. 5 depicts an exemplary method for shaping a nasal tissue using a tension element configured to act on multiple regions of a target nasal tissue.

As shown in FIG. 5, in some variations the method may be configured to alter the shape of a nasal tissue in multiple regions. In some variations, the method may be configured to utilize a single tension element (200) that is configured to act on multiple regions of the target nasal tissue. In some variations, the method may be configured to utilize more than one tension element to act on multiple regions of the target nasal tissue. In some variations, the method may be configured to alter the shape of multiple nasal tissues. In some variations, the method may be configured to alter the shape of multiple nasal tissues in multiple regions.

Delivery Devices

The tension elements described herein may be delivered using various delivery devices. The delivery devices may be configured to access various tissues in an atraumatic fashion, and may aid the passage of the tension elements through tissues in their insertion (low-profile) configuration. In general, the delivery devices may include a cannula comprising a proximal end, a distal end, and an atraumatic tip. The cannula may be straight or configured with a curve at its distal end, and may further include a lumen extending from the proximal end through the atraumatic tip, in which a tension element may be housed. A curved cannula may be useful in indexing rotation of the cannula and may allow buttressing against tissue, e.g., cartilage. Use of a curved cannula may also assist or support the anchor delivery element during penetration into tissue. The tension element may include a distal anchor configured to swivel at a pivot point from an insertion configuration to a deployed configuration upon the application of force to the tension element, as previously described herein. In some variations, the delivery devices may include a component that mechanically, electronically, or visually indicates the tension level of the tension element. In other variations, the tension level measurement component may be provided on the tension element itself.

The tension element and anchor delivery element may be preloaded in the delivery device or loaded into the delivery device directly before a procedure. A handle may be coupled to the cannula proximal end, and an actuator disposed on the handle. In one variation, the actuator may be concentrically disposed about the handle. In another variation, the actuator may comprise a pair of tabs that may be advanced and retracted with respect to the handle. The actuator may be coupled to the anchor delivery element and the tension element coupled thereto to advance the tension element and anchor delivery element from the lumen of the cannula.

In some variations, the cannula of the delivery device is made from a transparent material, such as a transparent plastic selected from the group consisting of acrylic, polycarbonate, polyethylene terephthalate, polyvinyl chloride, polyethylene, polypropylene, and polystyrene. In other variations, the cannula may be made from stainless steel or other suitable metals. The cannula may also have various cross-sectional shapes. For example, the cross-sectional shape of the cannula may be circular, non-circular, semi-circular, or ovular. Non-circular cannula cross-sectional shapes may aid in orienting the cannula to the plane of the cartilage or other tissue. Various cannula features may be combined. For example, a cannula may be straight and have an ovular cross-sectional shape, or the cannula may have a curved distal end and a circular cross-sectional shape. The tip of the cannula may also be configured to be atraumatic or cutting. For example, when working with submucosal tissue, an atraumatic cannula tip may be used to prevent unintentional trauma to the tissue. Alternatively, a cutting cannula tip may be used to create kerfs or scores in the cartilage prior to deploying the tension element to facilitate advancement of the tip component through the cartilage.

Figure 88A:
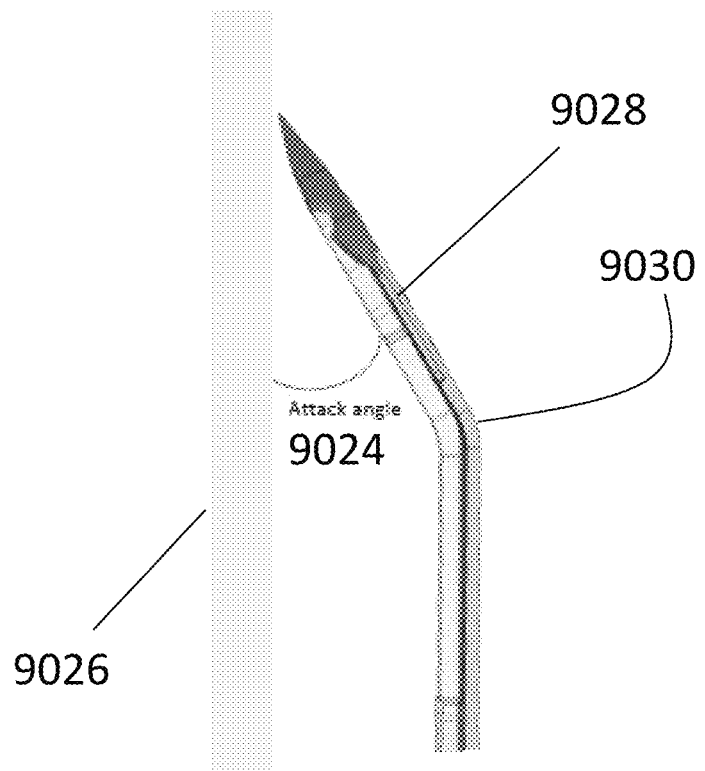
FIG. 88A depicts an exemplary cannula angle for deployment of a distal anchor into tissue and FIG. 88B depicts laser markings on an exemplary cannula.

When the cannula includes a curved distal end, as shown in FIG. 88A, the angle (9024) between tissue (e.g., nasal cartilage 9026) and the portion of the cannula (9028) distal to the curve (9030) may range from about 10 degrees to about 60 degrees, including all values and sub-ranges therein For example, the angle (9024) may be about 10 degrees, about 15 degrees, about 20 degrees, about 25 degrees, about 30 degrees, about 35 degrees, about 40 degrees, about 45 degrees, about 50 degrees, about 55 degrees, or about 60 degrees. The angle employed may help deploy the distal anchor at the target location.

Figure 88B:
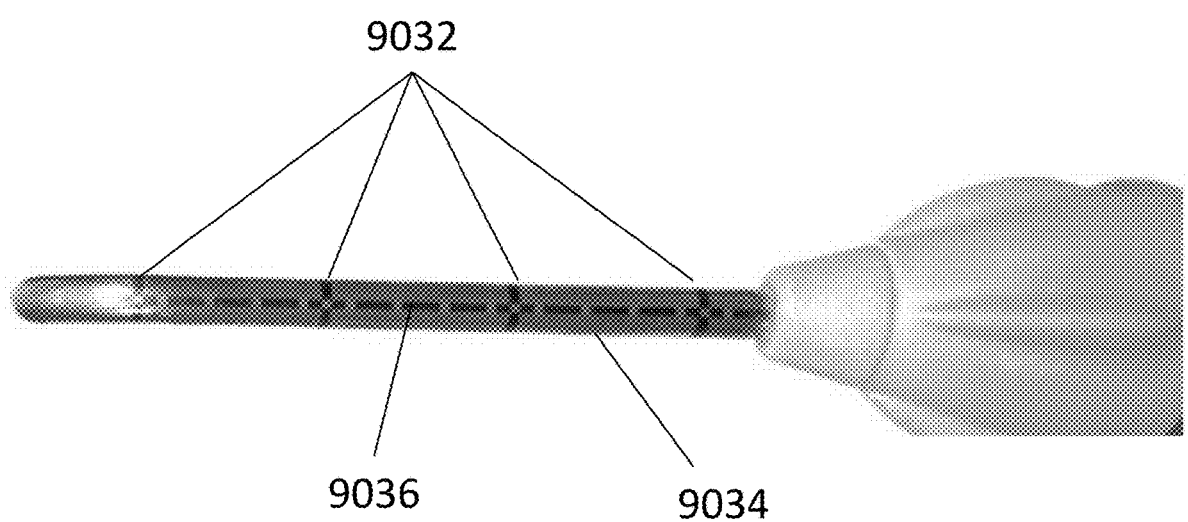

Cannula length may range from about 50 mm to about 70 mm, including all values and sub-ranges therein. For example, the length of the cannula may be about 50 mm, about 55 mm, about 60 mm, about 65 mm, or about 70 mm. In some variations, one or more portions along the cannula length may be flexible or malleable. In other variations, one or more markers may be provided along the cannula to help with visualizing the distal end of the cannula and/or determining the length of cannula inserted into the nasal cavity or tissue. In some variations, the markers may be laser markings. For example, as shown in FIG. 88B, a first set of laser markings (9032) spaced approximately 1.0 cm apart along the length of the cannula (9034) may be included to help determine the length of the cannula (9034) that has been inserted into the nasal cavity or tissue. Another centerline laser marking (9036) may be included to help with rotational orientation of the cannula (9034) prior to deployment of the tension element. A light element may also be included in the delivery device to help with visualization. In some variations, the light element may be a light wire configured to slide within the cannula lumen or a second lumen concentrically disposed within the cannula lumen or a lumen provided in the delivery device handle.

Some variations of the cannula may include an internal deflector within the cannula distal end that deflects or angulates the anchor delivery element as it is advanced out of the cannula. The internal deflector may be a flat, rigid surface within the cannula distal end that is angled about 30 degrees to about 70 degrees with respect to the longitudinal axis of the cannula. In other variations, the cannula distal tip may be preformed to have an angle of about 30 degrees to about 70 degrees with respect to the longitudinal axis of the cannula.

One or more ports in fluid communication with the lumen may be provided in the cannula for delivery of the tensioning element from the lumen into tissue. The one or more ports may be provided in any suitable location on the cannula, for example, at the distal tip of the cannula or distal side wall of the cannula. The one or more ports may also have any suitable shape. For example, the one or more ports may be circular, semi-circular, or ovular. When a port is provided at the distal tip of the cannula, the port may have a length and a depth. The length of the port may range from about 3.0 mm to about 6.0 mm. For example, the port length may be about 3.0 mm, about 3.5 mm, about 4.0 mm, about 4.5 mm, about 5.0 mm, about 5.5 mm, or about 6.0 mm. The depth of the port may range from about 1.0 mm to about 2.0 mm. For example, port depth may be about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm. In some variations, the port may have a depth that is about 30% to about 70% of the cannula outside diameter. The port may also have a curved portion and a flat portion when viewed from the side.

The delivery devices may also include a handle comprising a grip. Handle length may range from about 13 cm to about 25 cm, including all values and sub-ranges therein. The grip may include a plurality of ridges for enhancing the hold of a user on the handle. The handle and grip may be made from the same material or different materials. For example, the handle and grip may be made from materials such as, but not limited to, Nylon, silicone, polycarbonates, polyethylene, polypropylene, polyetheretherketone, polyetherimide, polyetherimide, Delrin, acrylic, polybenzimidazole, polyester, styrene acrylonitrile, or acrylonitrile butadiene styrene (ABS). Additionally, one or more directional indicators for orienting the port with respect to the location of anchoring in the target tissue may also be provided. One or more indicators on the handle may also be included to verify whether the tension element has been partially or entirely deployed from the cannula of the delivery device.

Figure 64A:
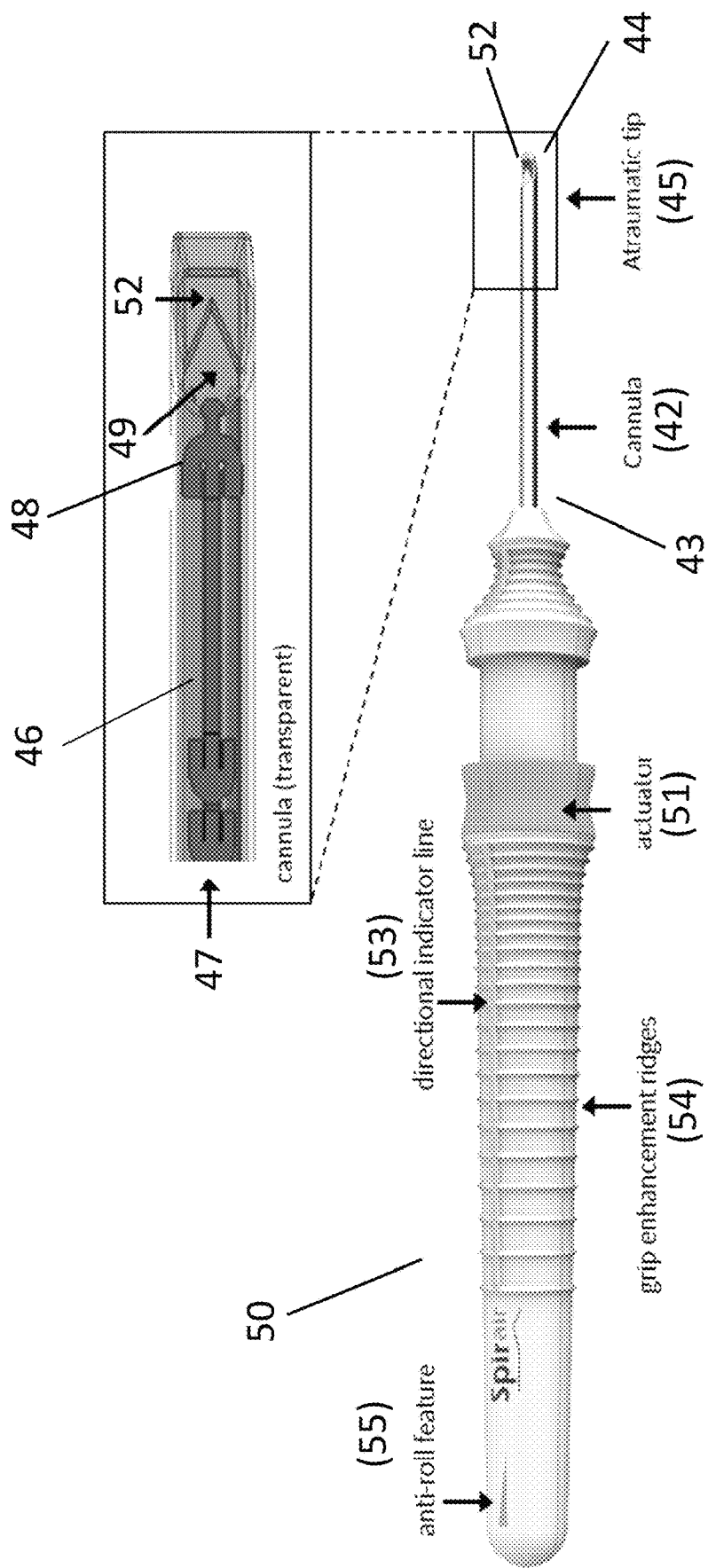
FIG. 64A depicts and exemplary device for delivering a tension element.
Figure 64B:
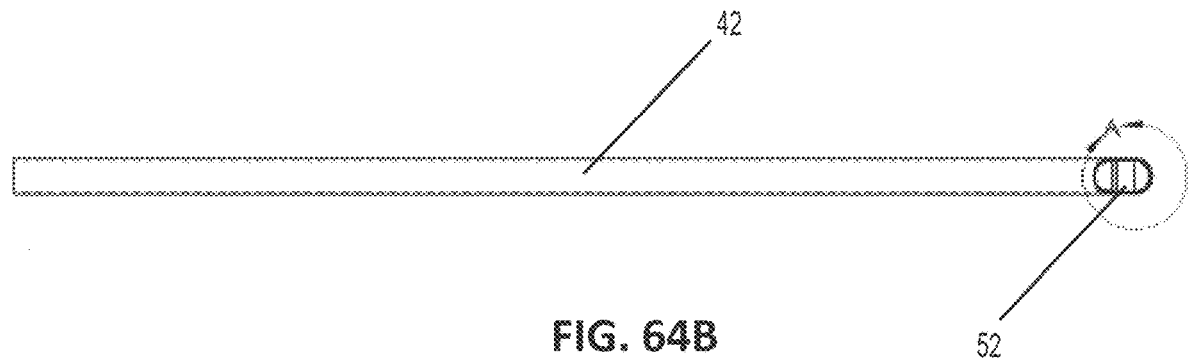
FIGS. 64B-64D depict further features of the distal port of the cannula shown in FIG. 64A.
Figure 64C:
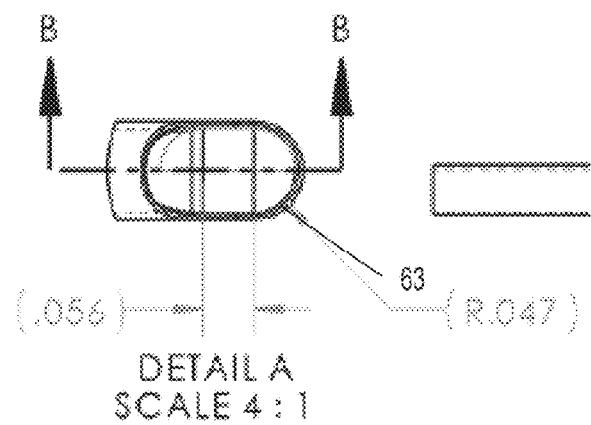
Figure 64D:
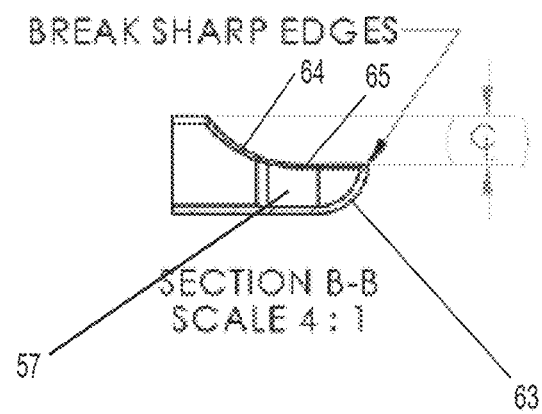
Figure 64E:
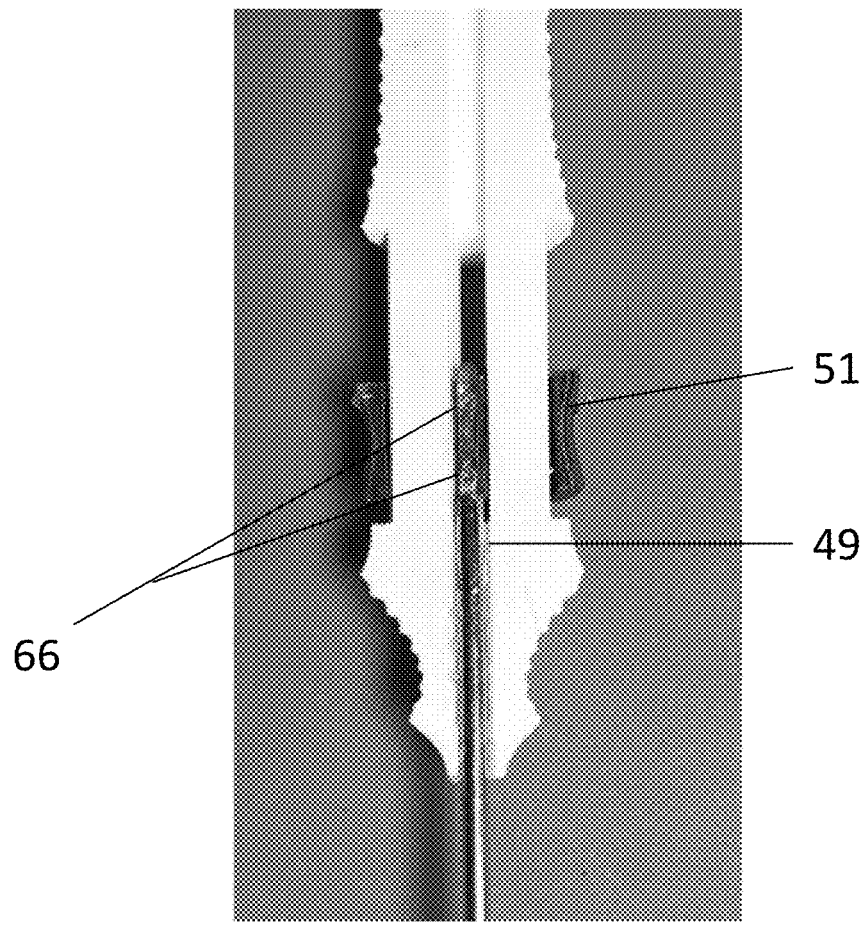
FIG. 64E depicts a cross-sectional view of the actuator of the delivery device shown in FIG. 64A coupled to an anchor delivery element.
Figure 65:
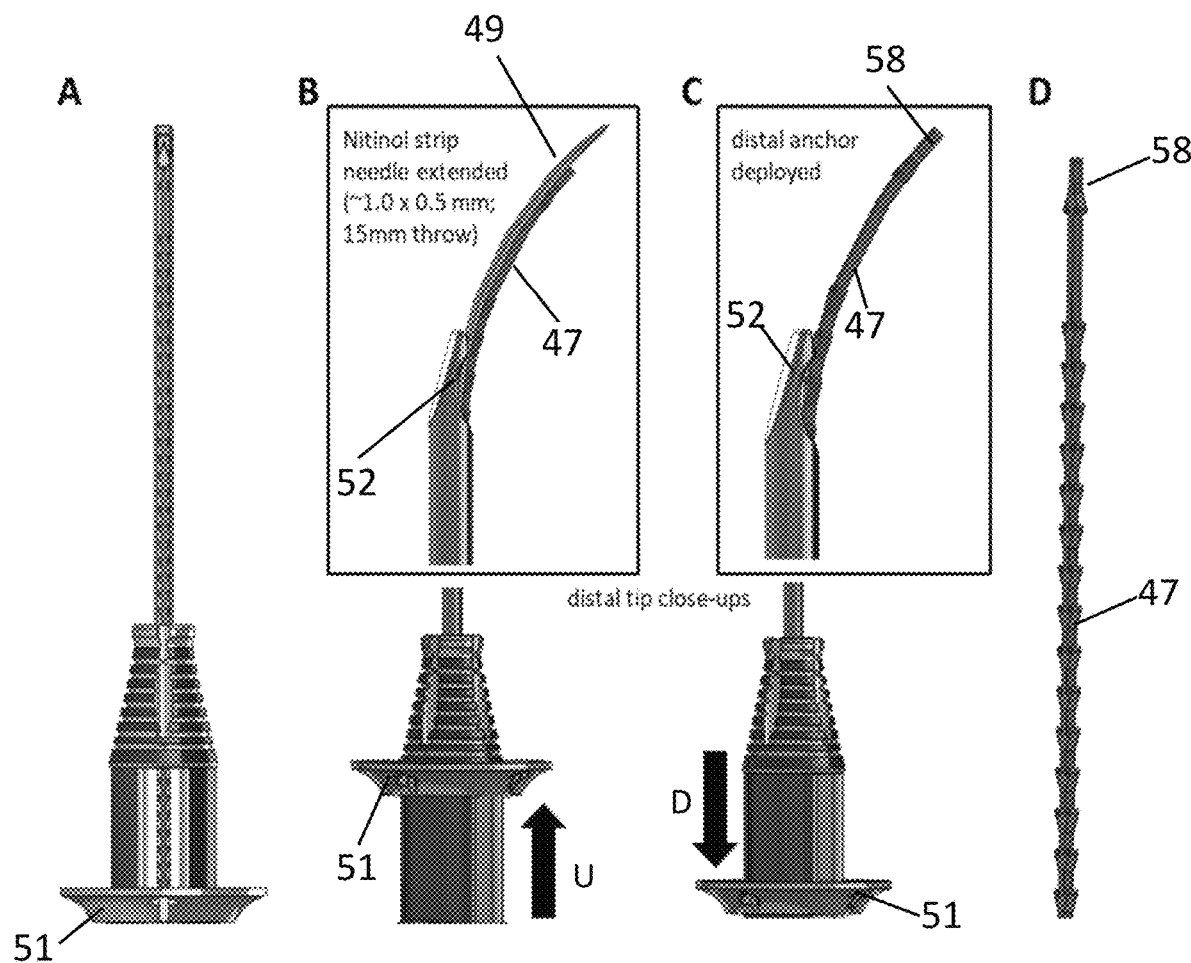
FIG. 65 depicts an exemplary method for deploying a tension element from a delivery device.

As shown in FIG. 64A, an exemplary delivery device may include a cannula (42) comprising a proximal end (43), a distal end (44), and an atraumatic tip (45). The cannula (42) may further include a lumen (46) extending from the proximal end (43) through the atraumatic tip (45), in which a tension element (47) may be housed. The tension element (47) may include a distal anchor (48) configured to swivel at a pivot point from an insertion configuration to a deployed configuration upon the application of force to the tension element, as previously described. Within the cannula lumen (46), the tension element (47) may be coupled to an anchor delivery element (49) with a cutting tip for use in piercing or penetrating tissues. A handle (50) may be coupled to the cannula proximal end (43), and an actuator (51) concentrically disposed about the handle (50). Actuator (51) may be advanced to deploy the tension element (47) from a distal port (52) of the cannula (42). As shown in more detail in FIG. 65, the actuator (51) may be advanced in the direction of arrow U to advance the tension element (47) and anchor delivery element (49) from the cannula distal port (52). After disengagement of the tension element from the anchor delivery element (49) and deployment of the distal anchor (58), the actuator (51) may be retracted in the direction of arrow D, and the delivery device withdrawn to deploy the full length of the tension element (47). As shown in the cross-sectional view of FIG. 64E, the actuator (51) may be coupled to the anchor delivery element (49) via screws (66). Referring back to FIG. 64A, a directional line indicator (53) may be provided on the handle (50) to help align the distal port with the tissue of interest. Grip enhancing ridges (54) may enhance the hold of a user on the handle (50). An anti-roll feature (55), which may be a thickened portion of the handle, may help steady the delivery device during delivery of the tension element (47). As shown in FIG. 64B, the distal port (52) of the cannula (42) may have an ovular shape. In the enlarged view provided in FIG. 64C, the atraumatic tip (45) may have a rounded portion (63). The rounded portion (63) may have a radius of curvature of approximately 1.19 mm. Additionally, port (52) may have a length (L) and a depth (D). The port length may range from about 3.0 mm to about 6.0 mm, and the port depth range from about 1.0 mm to about 2.0 mm, as previously described. The port may also have a curved portion (64) and a flat portion (65), as shown in the side view of FIG. 64D. This configuration of the cannula tip may aid in atraumatically accessing various tissues.

Figure 66:
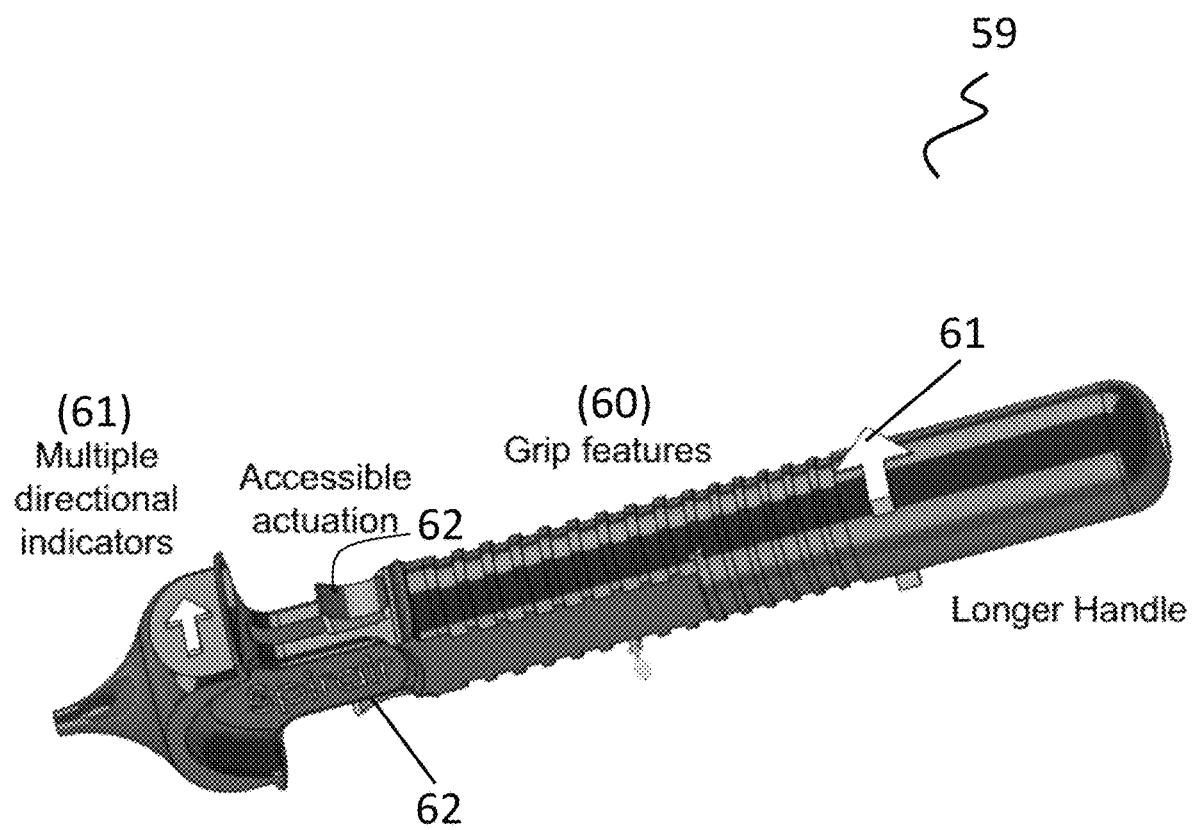
FIG. 66 depicts another exemplary handle for a delivery device.

In another variation, as shown in FIG. 66, the handle (59) may include a plurality of grip enhancing ridges (60) and directional indicators (61), similar to the handle provided in FIG. 64A. However, instead of being concentrically disposed about the handle, the actuator comprises two tabs (62). Advancement of the tabs toward the tissue may deploy the tension element from the delivery device, while retraction of the tabs (62) may withdraw and decouple the anchor delivery element from the tension element.

Figure 80A:
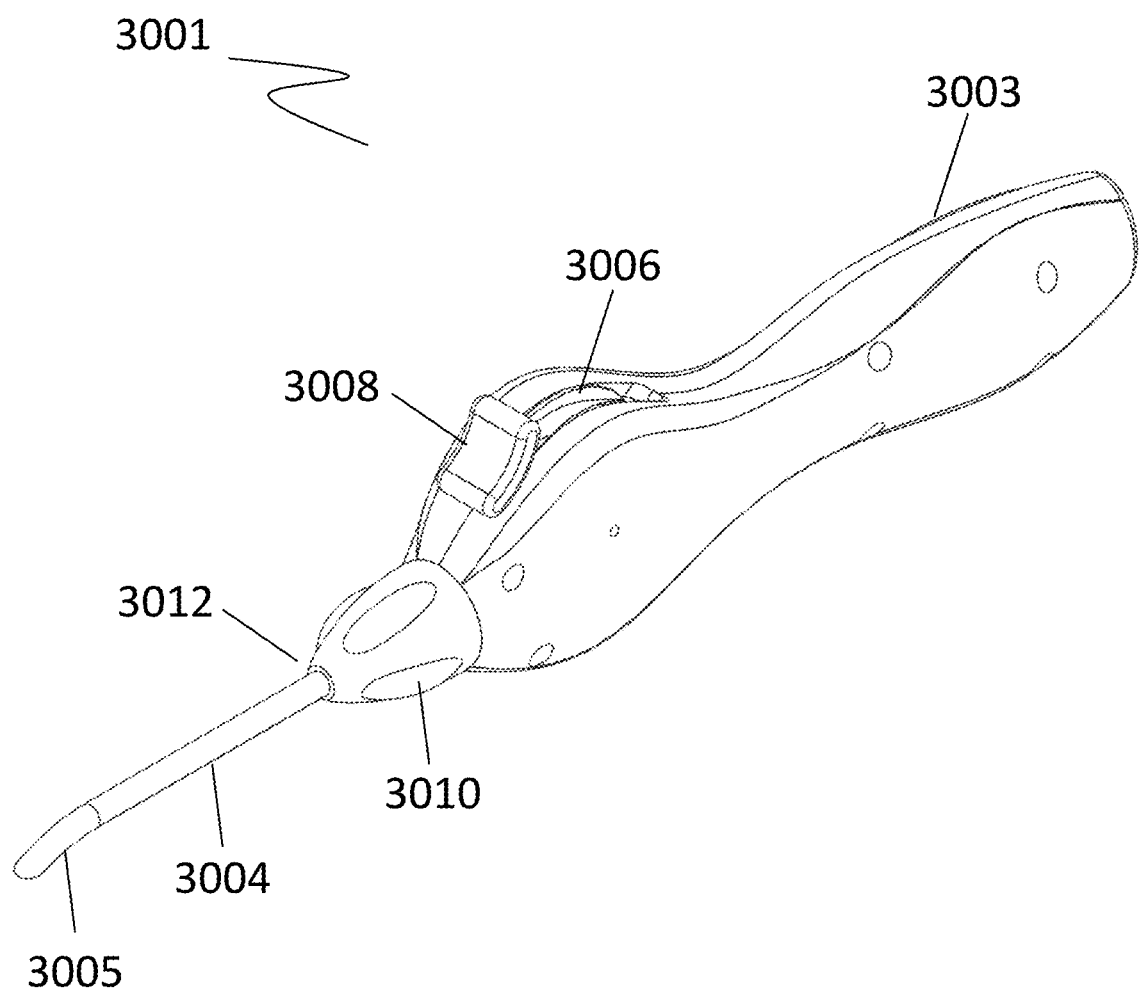
FIGS. 80A-80C depict exemplary delivery devices including rack and pinion mechanisms for deployment of an anchor delivery element.
Figure 80B:
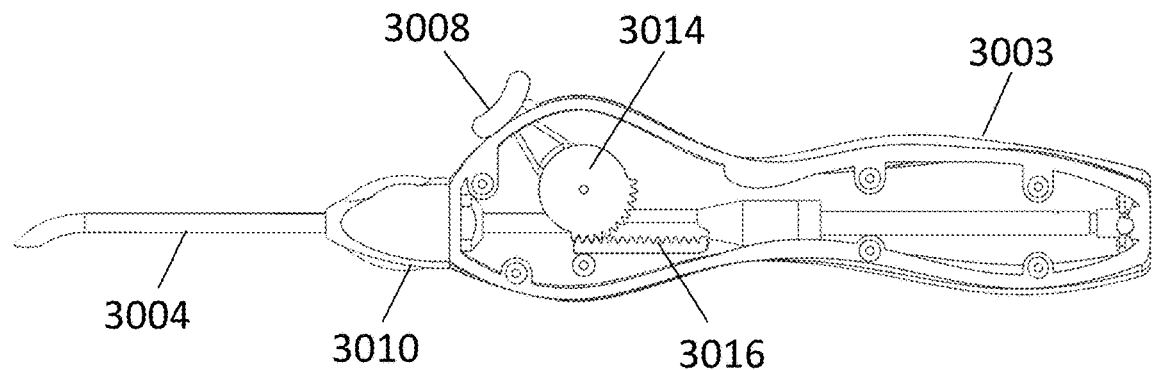
Figure 80C:
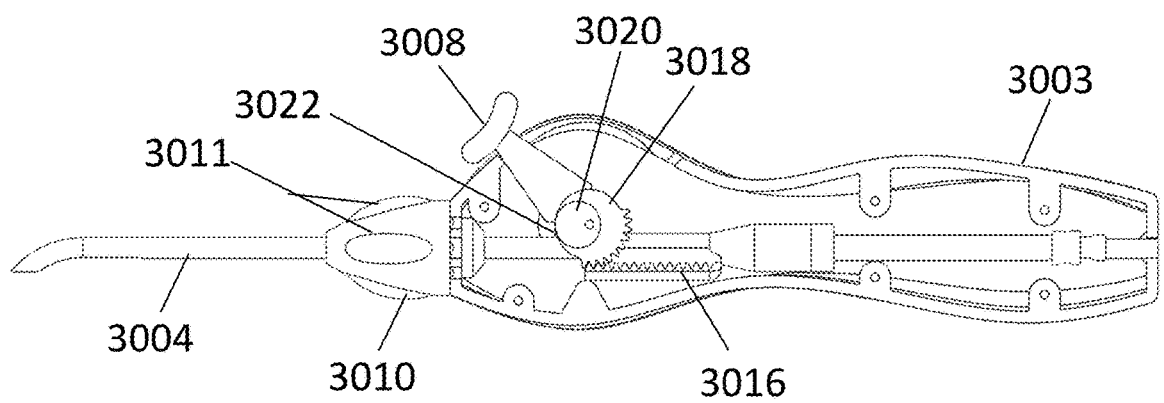

The delivery devices may include a mechanism or actuator configured to provide mechanical advantage to the deployment of the anchor delivery element from the cannula. Delivery devices with improved mechanical advantage may improve the ability of the device to puncture bone or thick or ossified cartilage, may improve the case of tension element deployment for the physician/surgeon, and/or may help reduce the pressure applied to brace the delivery device (and thus reduce the discomfort felt by an awake patient). The mechanical advantage may range from about 2:1 to about 4:1, including all values and sub-ranges therein. For example, the mechanical advantage may be about 2:1, about 2.5:1, about 3:1, about 3.5:1, or about 4:1. Such mechanisms may include linear gears and circular gears, e.g., rack and pinion mechanisms. The mechanisms may also include a capstan and a bowstring. An exemplary rack and pinion mechanism for the delivery device shown in FIG. 80A is illustrated in FIGS. 80B-80C. In FIG. 80A, delivery device (3001) includes a handle (3003) and a cannula (3004). Although the cannula (3004) is shown as having a curved distal end (3005), it is understood that the distal end may also be straight. The handle (3003) may include a slot (3006) through its surface so that a finger tab (3008) may be moved back and forth to actuate a pinion, as further described below. A knob (3010) may be attached to the proximal end (3012) of the cannula (3004) and be configured to rotate the cannula when rotated. Additionally, one or more indicators may be included on the surface of the knob (3010) to help identify the orientation of the curve when the delivery device includes a curved cannula. The indicator may be a detent, recess, nub, fin, or other protuberance extending from the surface of the knob. For example, referring to FIG. 80C, the one or more indicators may be fins (3011).

In one variation, as shown in FIG. 80B, the pinion may be a fixed sector gear (3014) configured to engage a corresponding rack (3016). In use, when the finger tab (3008) is moved back or forward in the slot (3006) (see FIG. 80A), the fixed sector gear (3014) that is coupled thereto rotates, which in turn linearly moves the rack (3016) to advance or retract the anchor delivery element (not shown). In another variation, as shown in FIG. 80C, the pinion may comprise an eccentric gear (3018). The eccentric gear (3018) may include a central pin (3020) that rides within a channel (3022) of the handle (3003). When the finger tab (3008) is moved back or forward in the slot (3006) (see FIG. 80A), the eccentric gear (3014), which is coupled to the finger tab (3008), also rotates, which in turn linearly moves the rack (3016) to advance or retract the anchor delivery element (not shown). Use of the eccentric gear (3018) may help maximize initial cartilage puncture and also enhance travel of the anchor delivery element. The rack and pinion mechanisms of FIGS. 80B and 80C may provide a mechanical advantage of about 2:1 to about 4:1.

Figure 81A:
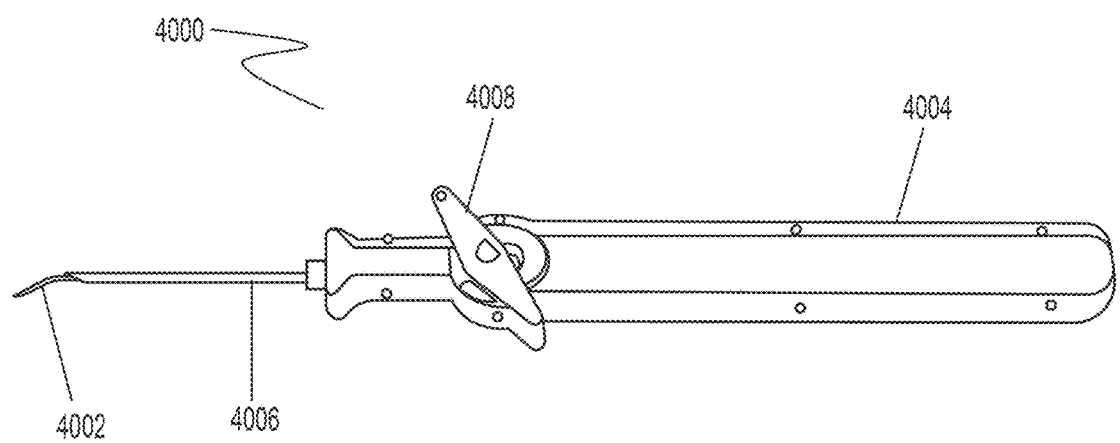
FIGS. 81A and 81B depict an exemplary delivery device including a capstan and bowstring mechanism for deployment of an anchor delivery element.
Figure 81B:
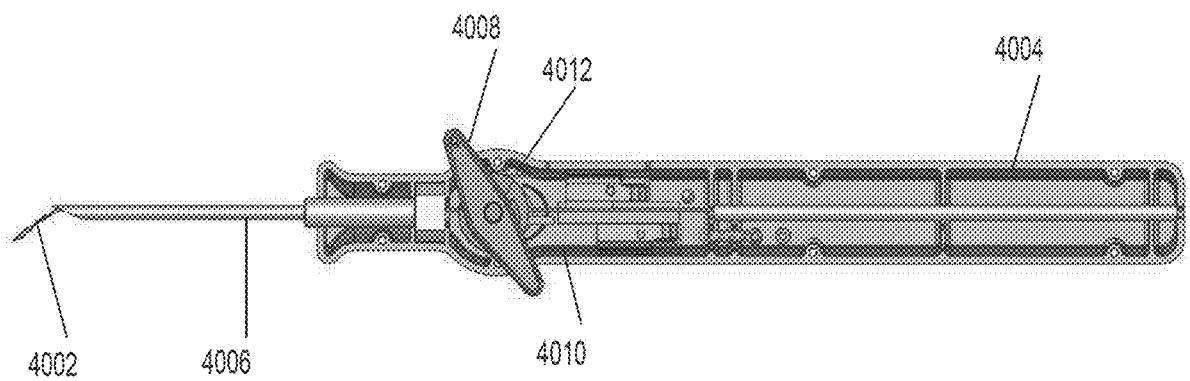

An exemplary capstan and bowstring mechanism is illustrated in FIGS. 81A and 81B. Referring to FIG. 81A, delivery device (4000) for deployment of an anchor delivery element (4002) may include a handle (4000), a cannula (4006) and lever (4008), which is rotatable with respect to the handle (4004). As shown in the cross-sectional view of FIG. 81B, the lever (4008) may be coupled to a capstan (4012) within the interior of the handle (4004) such that rotation of the lever (4008) rotates the capstan (4012). Upon rotation of the capstan (4012), a bowstring (4010), which may be attached to the capstan (4012), moves linearly to either advance the anchor delivery element out of the cannula (4002) or retract the anchor delivery element (4002) into the cannula (4006). The mechanical advantage provided by the delivery devices employing a capstan and bowstring mechanism may range from about 2:1 to about 4:1; however, in some instances it may be greater that 4:1.

Figure 82A:
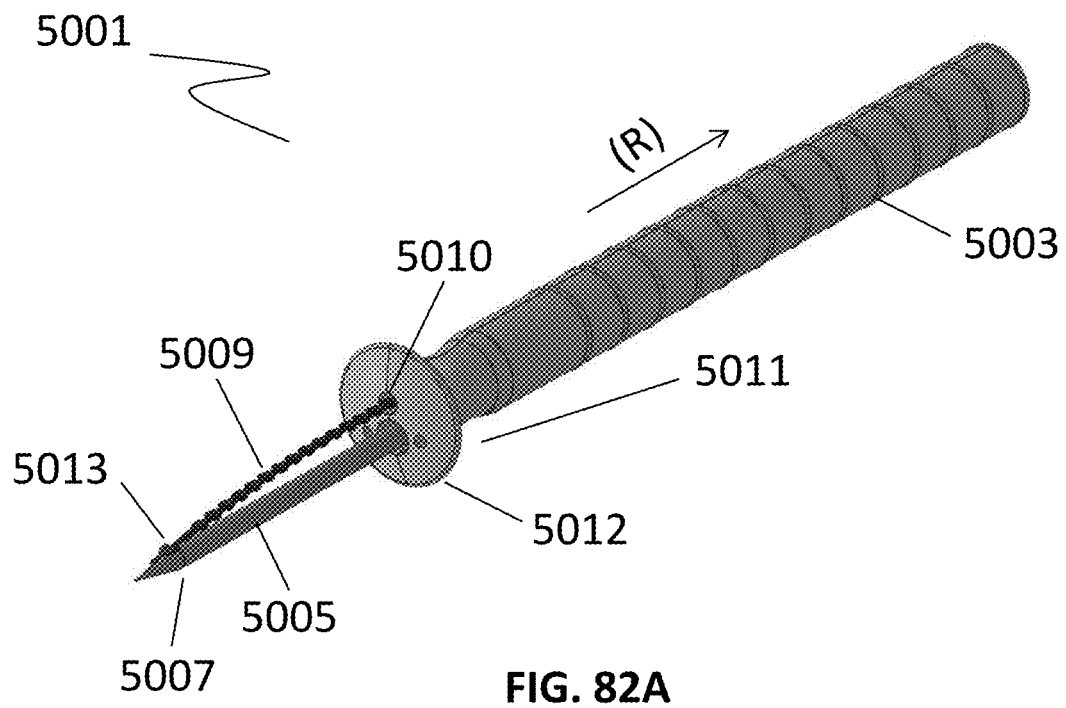
FIGS. 82A and 82B depict another exemplary device for delivering a tension element.
Figure 82B:
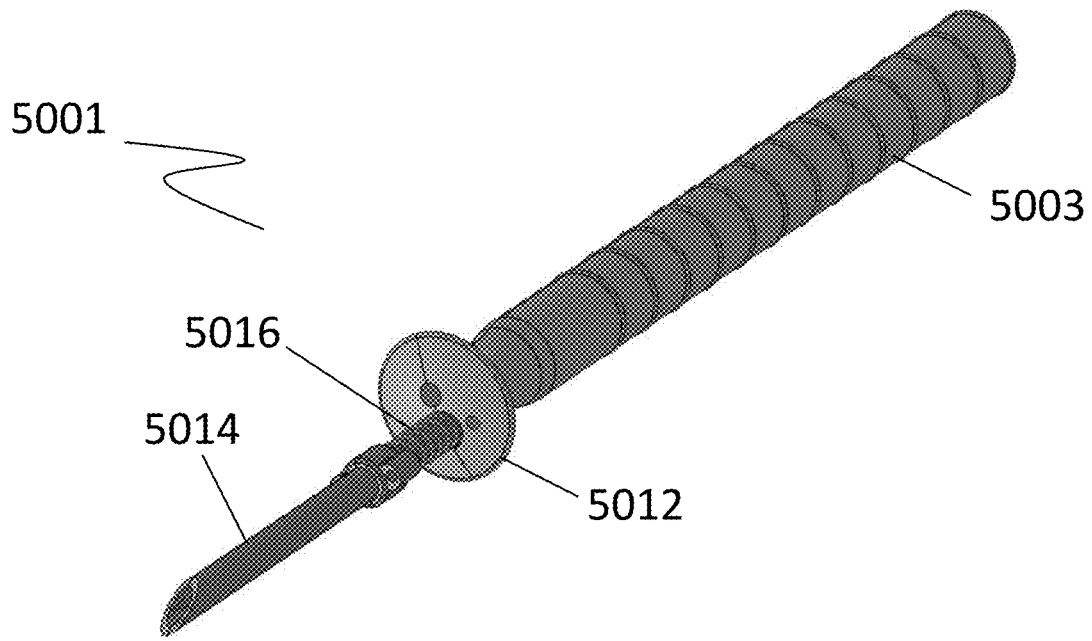

In some variations, as illustrated in FIG. 82A, the delivery device (5001) may comprise a handle (5003) with a flange (5012) at its distal end (5011), and a needle (5005) extending from the handle (5003). The flange (5012) may be provided as a stop against which further advancement into tissue is prevented. The distal anchor (5013) of a tension element (5009) may be coupled to the distal end (5007) of the needle (5005). After advancement through tissue to a target location, and upon retraction of the tension element (5009) in the direction of arrow (R) through opening (5010) of the handle (5003) (e.g., by a surgeon), the distal anchor (5013) may be detached from the needle (5005). As shown in FIG. 82B, the delivery device (5001) may further include a sheath (5014) concentrically disposed about the needle (5005) (see FIG. 82A) and retractable by compression against a spring (5016) to help protect the needle prior to its deployment.

EXAMPLE

The following example is illustrative only and should not be construed as limiting the disclosure in any way.

Example 1: Tension Element Tolerability and Effect on Obstruction Symptoms

Figure 92:
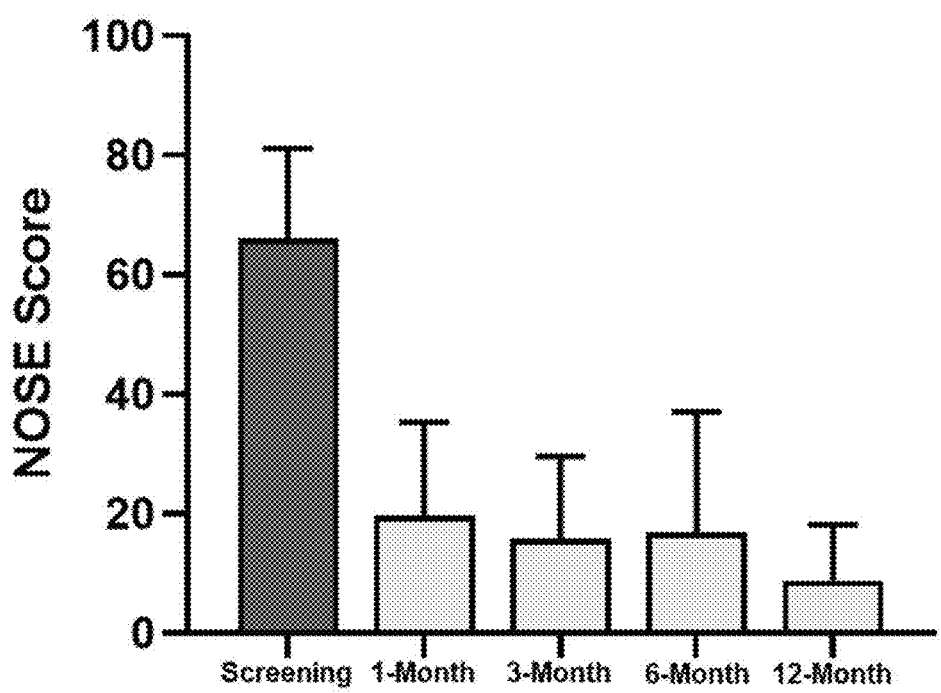
FIG. 92 is a bar graph providing NOSE scores of subjects with tension elements placed to treat nasal septal deviation. The NOSE scores were obtained at one-month, 3 months, 6 month, and 12 months after tension element placement.

Fourteen (14) subjects with cartilaginous nasal septal deviation were screened for treatment at two clinical sites using an elongate tension element made from polydioxanone (PDO) and including a distal Z-Flex anchor and a plurality of proximal anchors. Preliminary results after placement of the elongate tension element, which are shown in FIG. 92 and the table below, are provided as Nasal Obstruction Symptom Evaluation (NOSE) patient-reported outcome scores. NOSE scores may help assess how breathing symptoms affect a subject's quality of life. NOSE is a five question survey that uses a 20-point scale to capture breathing symptoms, with higher scores indicating more severe symptoms than lower scores. The questions related to symptoms of nasal congestion or stuffiness, nasal blockage or obstruction, trouble breathing through the nose, trouble sleeping, and ability to get air through the nose during exercise or exertion.

The table below shows the number of subjects completing their follow-up visit at one month (M1), three months (M3), six months (M6), and 12 months (M12) and the average NOSE scores of those subjects at screening and at M1, M3, M6, and M12. Referring to the table and FIG. 92, an improvement in obstructive symptoms and quality of life for those subjects is illustrated given that average NOSE scores decreased from about 66 to about 9 over the course of 12 months for the subjects. More specifically, the average NOSE score was 66 at the time of screening, about 20 at M1, about 16 at M3, about 17 at M6, and about 9 at M12.

| Visit | Subjects Completed | Average NOSE Score |
| --- | --- | --- |
| Screening | 14 | 66 |
| M1 | 14 | 20 |
| M3 | 13 | 16 |
| M6 | 8 | 17 |
| M12 | 4 | 9 |

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated.

The invention claimed is:

1. A method for manipulating one or more nasal tissues in a subject comprising:
   inserting a delivery device through an access site in a nasal tissue on a first side of a nasal septum and through the nasal septum to a second side of the nasal septum, the delivery device comprising a piercing tip and having an elongate tension element coupled thereto;
   deploying the elongate tension element from the delivery device to the second side of the nasal septum;
   passing a proximal end of the elongate tension element back through the access site in the nasal tissue to the second side of the nasal septum;
   tensioning the elongate tension element to a tensioned state; and
   securing the proximal end of the elongate tension element in its tensioned state to tissue on the second side of the nasal septum.

2. The method of claim 1, wherein the delivery device is a needle.

3. The method of claim 2, wherein the needle is removably attached to the elongate tension element.

4. The method of claim 1, wherein tensioning the elongate tension element is used to treat nasal septal deviation.

5. The method of claim 1, wherein tensioning the elongate tension element is used to manipulate a nasal turbinate.

6. The method of claim 1, wherein tensioning the elongate tension element is used to medialize a middle turbinate.

7. The method of claim 1, wherein deploying the elongate tension element further comprises placing the elongate tension element through a middle turbinate.

8. The method of claim 1, wherein the deploying the elongate tension element comprises placing the elongate tension element around a middle turbinate.

9. The method of claim 1, wherein the elongate tension element is used to treat nasal airway obstruction.

10. The method of claim 1, wherein the access site comprises a submucosal tunnel beneath a nasal septum.

11. The method of claim 1, further comprising securing a distal anchor of the elongate tension element into nasal cartilage on the second side of the nasal septum, the distal anchor comprising a pivot point and having an insertion configuration and a deployed configuration.

12. The method of claim 11, wherein securing the distal anchor comprises applying a force to the elongate tension element to swivel the distal anchor at the pivot point from the insertion configuration to the deployed configuration.

13. The method of claim 1, further comprising repeating the passage of the proximal end of the elongate tension element back through the access site.

14. The method of claim 1, wherein the elongate tension element in its tensioned state applies a force ranging from about 4.0 Newtons to about 10 Newtons to the one or more nasal tissues.

15. The method of claim 1, wherein the elongate tension element comprises a biodegradable polymer.

16. The method of claim 15, wherein the biodegradable polymer comprises PDO (Poly(dioxanone)).

17. The method of claim 15, wherein the biodegradable polymer is configured to biodegrade over a period of at least about six months.

18. The method of claim 1, wherein the elongate tension element comprises a distal anchor, the distal anchor comprising an anchor body and a pivot point, and one or more arms extending from the anchor body.

19. The method of claim 18, wherein a distal end of the one or more arms is beveled.

20. The method of claim 1, wherein the elongate tension element has a tensile strength ranging from about 100 MPa to about 800 MPa.

21. The method of claim 1, wherein the elongate tension element further comprises a plurality of proximal anchors.

22. The method of claim 1, wherein the elongate tension element further comprises a needle at a proximal end thereof.

23. The method of claim 1, wherein the delivery device comprises an anchor delivery element.

24. The method of claim 23, wherein the anchor delivery element is advanced with a deployed force that is greater than an applied force by a user.

25. The method of claim 24, wherein a ratio of the deployed force to the applied force ranges from about 2:1 to about 4:1.

26. The method of claim 23, wherein the anchor delivery element is advanced using an actuator comprising a linear gear and a fixed sector gear.

27. The method of claim 23, wherein the anchor delivery element is advanced using an actuator comprising a linear gear and an eccentric sector gear.

28. The method of claim 23, wherein the anchor delivery element comprises a cutting tip and an anchor support.

29. The method of claim 28, wherein the cutting tip is coupled to the anchor support by one or more rivets.

* * * * *